United States Patent [19]

Waldman et al.

[11] Patent Number: 6,120,995
[45] Date of Patent: Sep. 19, 2000

[54] COMPOSITIONS THAT SPECIFICALLY BIND TO COLORECTAL CANCER CELLS AND METHODS OF USING THE SAME

[75] Inventors: Scott A. Waldman, Ardmore; Joshua M. Pearlman, Philadelphia; Michael T. Barber, Paoli; Stephanie Schulz, West Chester; Scott J. Parkinson, Philadelphia, all of Pa.

[73] Assignee: Thomas Jefferson University, Philadelphia, Pa.

[21] Appl. No.: 08/908,643

[22] Filed: Aug. 7, 1997

[51] Int. Cl.[7] .......................... C12Q 1/68; G01N 33/574; C07H 21/04
[52] U.S. Cl. .............................. 435/6; 435/7.23; 435/810; 536/24.33
[58] Field of Search ................................ 536/23.5, 24.3, 536/24.31, 24.33; 435/6, 7.23, 810; 436/64

[56] References Cited

U.S. PATENT DOCUMENTS

| | | | |
|---|---|---|---|
| 4,022,878 | 5/1977 | Gross | 424/1.5 |
| 4,329,281 | 5/1982 | Christenson et al. | 260/112 B |
| 4,526,716 | 7/1985 | Stevens | 260/112.5 R |
| 4,584,268 | 4/1986 | Ceriani et al. | 436/504 |
| 4,601,896 | 7/1986 | Nugent | 424/36 |
| 4,683,195 | 7/1987 | Mullis et al. | 435/6 |
| 4,683,202 | 7/1987 | Mullis | 435/91 |
| 4,729,893 | 3/1988 | Letcher et al. | 424/98 |
| 4,736,866 | 4/1988 | Leder et al. | 800/1 |
| 4,849,227 | 7/1989 | Cho | 424/498 |
| 4,873,191 | 10/1989 | Wagner et al. | 435/172.3 |
| 4,945,050 | 7/1990 | Sanford et al. | 435/172.1 |
| 4,963,263 | 10/1990 | Kauvar | 210/635 |
| 4,965,188 | 10/1990 | Mullis et al. | 435/6 |
| 5,017,487 | 5/1991 | Stunnenberg et al. | 435/172.3 |
| 5,037,645 | 8/1991 | Strahilevitz | 424/85.8 |
| 5,075,216 | 12/1991 | Innis et al. | 435/6 |
| 5,112,606 | 5/1992 | Shiosaka et al. | 530/389.2 |
| 5,133,866 | 7/1992 | Kauvar | 210/635 |
| 5,143,854 | 9/1992 | Pirrung et al. | 436/518 |
| 5,160,723 | 11/1992 | Welt et al. | 424/1.1 |
| 5,217,869 | 6/1993 | Kauvar | 435/7.9 |
| 5,221,736 | 6/1993 | Coolidge et al. | 536/25.31 |
| 5,223,409 | 6/1993 | Ladner et al. | 435/69.7 |
| 5,237,051 | 8/1993 | Garbers et al. | 530/350 |
| 5,252,743 | 10/1993 | Barrett et al. | 548/303.7 |
| 5,270,170 | 12/1993 | Schatz et al. | 435/7.37 |
| 5,271,961 | 12/1993 | Mathiowitz et al. | 427/213.31 |
| 5,288,514 | 2/1994 | Ellman | 427/2 |
| 5,324,483 | 6/1994 | Cody et al. | 422/131 |
| 5,330,892 | 7/1994 | Vogelstein et al. | 435/6 |
| 5,338,665 | 8/1994 | Schatz et al. | 435/6 |
| 5,340,474 | 8/1994 | Kauvar | 210/198.2 |
| 5,350,741 | 9/1994 | Takada | 514/3 |
| 5,352,775 | 10/1994 | Albertsen et al. | 536/23.1 |
| 5,366,862 | 11/1994 | Venton et al. | 435/7.1 |
| 5,384,261 | 1/1995 | Winkler et al. | 436/518 |
| 5,395,750 | 3/1995 | Dillon et al. | 435/5 |
| 5,399,347 | 3/1995 | Trentham et al. | 424/184.1 |
| 5,405,783 | 4/1995 | Pirrung et al. | 436/518 |
| 5,412,087 | 5/1995 | McGall et al. | 536/24.3 |
| 5,420,328 | 5/1995 | Campbell | 558/110 |
| 5,424,186 | 6/1995 | Fodor et al. | 435/6 |
| 5,430,138 | 7/1995 | Urdea et al. | 536/26.8 |
| 5,437,977 | 8/1995 | Segev | 435/6 |
| 5,518,888 | 5/1996 | Waldman | 435/7.23 |
| 5,597,909 | 1/1997 | Urdea et al. | 536/24.3 |
| 5,601,990 | 2/1997 | Waldman | 435/7.23 |
| 5,731,159 | 3/1998 | Waldman | 435/7.23 |

OTHER PUBLICATIONS

Adams, R.D., "Anxiety, Depression, Asthenia, and Personality Disorders" in *Harrison's Principles of Internal Medicine*, McGraw–Hill Book Co., N.Y., 1983, p. 68.

Alexander et al., "Oncogene alterations in rat colon tumors induced by N–methyl–N–nitrosourea", *Am. J. Med. Sci.*, 1992, 303(1), 16–24.

Beck–Sickinger et al., "Neuropeptide Y: identification of the binding site", *Int. J. Peptide Protein Res.*, 1990, 36, 522–530.

Berd et al., "Induction of Cell–mediated Immunity to Autologous Melanoma Cells and Regression of Metastases after Treatment with a Melanoma Cell Vaccine Preceded by Cyclophosphamide", *Cancer Res.*, 1986, 46, 2572–2577.

Berd et al., "Immunization with Haptenized, Autologous Tumor Cells Induces Inflammation of Human Melanoma Metastases", *Cancer Res.*, 1991, 51, 2731–2734.

Blond–Elguindi et al., "Affinity Panning of a Library of Peptides Displayed on Bacteriophages Reveals the Binding Specificity of BiP", *Cell*, 1993, 75, 717–728.

Bold et al., "Experimental gene therapy of human colon cancer", *Surgery*, 1994, 116(2), 189–196.

Ciardiello et al., "Inhibition of CRIPTO expression and tumorigenicity in human colon cancer cells by antisense RNA and oligodeoxynucleotides", *Oncogene*, 1994, 9(1), 291–298.

Collins et al., "c–myc antisense oligonucleotides inhibit the colony–forming capacity of Colo 320 colonic carcinoma cells", *J. Clin. Invest.*, 1992, 89(5), 1523–1527.

(List continued on next page.)

*Primary Examiner*—Yvonne Eyler
*Attorney, Agent, or Firm*—Woodcock Washburn Kurtz Mackiewicz & Norris LLP

[57] ABSTRACT

A unique transcription product, CRCA-1, and alternative translation products generated thereform, are disclosed. The transcript and its translation products are markers for colorectal cells. Screening and diagnostic reagents, kits and methods for metastasized colorectal cancer are disclosed as are reagents, kits and methods for identifying adenocarcinomas as colorectal in origin. Compounds, compositions and methods of treating patients with metastasized colorectal cancer and for imaging metastasized colorectal tumors in vivo are disclosed. Compositions and methods for delivering active compounds such as gene therapeutics and antisense compounds to colorectal cells are disclosed. Vaccines compositions and methods of for treating and preventing metastasized colorectal cancer are disclosed.

11 Claims, 1 Drawing Sheet

OTHER PUBLICATIONS

Cooney et al., "Site–Specific Oligonucleotide Binding Represses Transcription of the Human c–myc Gene in Vitro", *Science,* 1988, 241, 456–459.

Coperhave et al., "The Digestive System", *Bailey's Textbook of Histology,* 16th Edition, Williams and Wilkens, Baltimore, MD, 1975, p. 404.

Cull et al., "Screening for receptor ligands using large libraries of peptides linked to the C terminus of the lac repressor", *Proc. Natl. Acad. Sci. USA,* 1992, 89, 1865–1869.

Francis et al., Peptide Vaccines Based on Enhanced Immunogenicity of Peptide Epitopes Presented with T–Cell Determinants or Hepatitis B Core Protein, *Methods in Enzymol.,* 1989, 178, 659–676.

Gallop et al., "Applications of Combinatorial Technologies to Drug Discovery. 1. Background and Peptide Combinatorial Libraries", *J. Med. Chem.,* 1994, 37(9), 1233–1251.

Gordon et al., "Applications of Combinatorial Technologies to Drug Discovery. 2. Combinatorial Organic Synthesis, Library Screening Strategies, and Future Directions", *J. Med.Chem.,* 1994, 37(10), 1385–1401.

Hammer et al., "Promiscuous and Allele–Specific Anchors in HLA–DR–Binding Peptides", *Cell,* 1993, 74, 197–203.

Haralambidis et al., "The Solid Phase Synthesis of Oligonucleotides Containing a 3'–Peptide Moiety", *Tetra. Letts.,* 1987, 28(43), 5199–5202.

Helen et al., "Specific regulation of gene expression by antisense, sense, and antigene nucleic acids", *Biochem. Biophys. Acta,* 1990, 1049, 99–125.

Kniazev et al., "Comprehensive Characteristics of Alterations of HER–2/ERBB–2, HER–1/ERBB–1, HRAS–1, and C–MYC Oncogenes, and of p53 and RBI Antioncogenes, and also of Deletions of Loci of Chromosome 17 in Colorectal Carcinomas", *Mol. Biol.,* 1992, 26(5), 1–15.

Kwok et al., "Calculation of radiation doses for nonuniformly distributed β and γ radionuclides in soft tissue", *Med. Phys.,* 1985, 12(4), 405–412.

MacLean et al., "Immunization of breast cancer patients using a synthetic sialyl–Tn glycoconjugate plus Detox adjuvant", *Cancer Immunol. Immunother.,* 1993, 36, 215–222.

Magerstadt, M., *Antibody Conjugates and Malignant Disease,* CRC Press, Boca Raton, USA, 1991, 110–152.

Melani et al., "Inhibition of proliferation by c–myb antisense oligodeoxynucleotides in colon adenocarcinoma cell lines that express c–myb", *Cancer Res.,* 1991, 51(11), 2897–2901.

Miller et al., "The Induction of Hapten–Specific T Cell Tolerance by Using Hapten–Modified Lymphoid Cells", *J. Immunol.,* 1976, 117(5:1), 1519–1526.

Nielsen et al., "Sequence–specific transcription arrest by peptide nucleic acid bound to the DNA template strand", *Gene,* 1994, 149, 139–145.

Osteresh et al., "Libraries from libraries": Chemical transformation of combinatorial libraries to extend the range and repertoire of chemical diversity, *Proc. Natl. Acad. Sci. USA,* 1994, 91, 11138–11142.

Ohlmeyer et al., "Complex synthetic chemical libraries indexed with molecular tags", *Proc. Natl. Acad. Sci USA,* 1993, 90, 10922–10926.

Ramsey et al., "Myb expression is higher in malignant human colonic carcinoma and premalignant adenomatous polyps than in normal mucosa", *Cell Growth & Different.,* 1992, 3(10), 723–730.

Rodriguez–Alfageme et al., "Suppression of deregulated c–MYC expression in human colon carcinoma cells by chromosome 5 transfer", *Proc. Natl. Acad. Sci. USA,* 1992, 89(4), 1482–1486.

Ruggeri et al., "Inhibition of platelet function with synthetic peptides designed to be high–affinity antagonists of fibrinogen binding to platelets", *Proc. Natl. Acad. Sci. USA,* 1986, 83, 5708–5712.

Sad et al., "Bypass of carrier–induced epitope–specific suppression using a T–helper epitope", *Immunology,* 1992, 76, 599–603.

de Sauvage et al., "Primary Structure and Functional Expression of the Human Receptor for *Escherichia coli* Heat–stable Enterotoxin", *J. Biol. Chem.,* 1991, 266(27), 17912–17918.

Sepetov et al., "Library of libraries: Approach to synthetic combinatorial library design and screening of "pharmacophore" motifs", *Proc. Natl. Acad. Sci. USA,* 1995, 92, 5426–5430.

Sizeland et al., "Antisense transforming growth factor alpha oligonucleotides inhibit autocrine stimulated proliferation of a colon carcinoma cell line", *Mol. Biol. Cell,* 1992, 3(11), 1235–1243.

Smith et al., "A ribonuclease S–peptide antagonist discovered with a bacteriophage display library", *Gene,* 1993, 128, 37–42.

Takekawa et al., "Chromosomal localization of the protein tyrosine phosphatase G1 gene and characterization of the aberrant transcripts in human colon cancer cells", *FEBS Letts.,* 1994, 339(3), 222–228.

Tanaka et al., "Suppression of tumorigenicity in human colon carcinoma cells by introduction of normal chromosome 1p36 region", *Oncogene,* 1993, 8(8), 2253–2258.

Toribara et al., "Screening for colorectal cancer", *New Eng. J. Med.,* 1995, 332(13), 861–867.

Ullrich et al., "Insulin–like growth factor I receptor primary structure: comparison with insulin receptor suggests structural determinants that define functional specificity", *EMBO J.,* 1986, 5(10), 2503–2512.

Waldman et al., "Immunoaffinity Purification of Soluble Guanylyl Cyclase", *Methods in Enzymol.,* 1991, 195, 391–396.

Wang et al., "Application of the Multipin Peptide Synthesis Technique for Peptide Receptor Binding Studies: Substance P as a Model System", *Bioorg. Med. Chem. Lett.,* 1993, 3(3), 447–450.

Wessels et al., "Radionuclide selection and model absorbed dose calculations for radiolabeled tumor associated antibodies", *Med. Phys.,* 1984, 11(5), 638–645.

Wide, "Solid Phase Antigen–Antibody Systems", *Radioimune Assay Method,* Kirkham (ed.), E. & S. Livingstone, Edinburgh, 1970, 405–413.

Wu et al., "Evidence for ed gene delivery to Hep G2 hepatoma cells in vitro", *Biochem.,* 1988, 27, 887–892.

Yokozaki et al., "An antisense oligodeoxynucleotide that depletes RI alpha subunit of cyclic AMP–dependent protein kinase induces growth inhibition in human cancer cells", *Cancer Res.,* 1993, 53(4), 868–872.

Zuckermann et al., "Discovery of Nanomolar Ligands for 7–Transmembrane G–Protein–Coupled Receptors from a Diverse N–(Substituted)glycine Peptoid Library", *J. Med. Chem.,* 1994, 37, 2678–2685.

Almenoff, et al., "Ligand–based Histochemical Localization and Capture of Cells Expressing Heat–Stable Enterotoxin Receptors", *Mol. Microbiol.,* 1993, 8, 865–873.

Chelly, J. et al., "Illegitimate transcription: Transcription of any gene in any cell type", *Proc. Natl. Acad. Sci. USA,* 1989, 86, 2617–2621.

Chelly, J. et al., "Illegitimate Transcription: Application to the Analysis of Truncated Transcripts of the Dystrophin Gene in Nonmuscle Cultured Cells from Duchenne and Becker Patients", *J. Clin. Invest.,* 1991, 88(4), 1161–1166.

Cohen, M., et al., "Receptors for *Escherichia coli* Heat Stable Enterotoxin in Human Intestine and in a Human Intestinal Cell Line (Caco–2)", *J. Cellular Physiol.,* 1993, 156, 138–144.

Cooper, D.N. et al., "Ectopic (Illegitimate) Transcription: New Possibilities for the Analysis and Diagnosis of Human Genetic Disease", *Ann. Med.,* 1994, 26(1), 9–14.

de Sauvage, F., et al., "Primary Structure and Functional Expression of the Human Receptor for *Escherichia coli* Heat–stable Enterotoxin", *J. Biol. Chem.,* 1991, 266, 17912–17918.

Drewett, J. et al., "The Family of Guanylyl Cyclase Receptors and Their Ligands", *Endocrine Reviews,* 1994, 15(2), 135–162.

Forte, L., et al., "Receptors and cGMP Signaling Mechanism for *E. Coli* Enterotoxin in Opossum Kidney", *Am. J. Physiol.,* 1988, 255 (5 Pt. 2), F1040–F1046.

Forte, L., et al., "*Escherichia coli* Enterotoxin Receptors: Localization in Opossum Kidney, Intestine, and Testis", *Am. J. Physiol.,* 1989, 257 (Pt. 2), F874–881.

Guarino, A., et al., "$T^{84}$ Cell Receptor Binding and Guanyl Cyclas Activation by *Escherichia coli* Heat–Stable Toxin", *Am. J. Physiol,* 253 (Gastrointest. Liver Physiol. 16): G775–780, 1987.

Guerrant, R., et al., "Activation of Intestinal Guanylate Cyclase by Heat–Stable Enterotoxin of *Escherichia coli:* Studies of tissue Specificity, Potential Receptors, and Intermediates", *J. Infect. Dis.,* 1980, 142(2), 220–228.

Hakki, et al., "Solubilization and Characterization of Functionally Coupled *Escherichia coli* Heat–Stable Toxin Receptors and Particulate Guanylate Cyclase Associated with the Cytoskeleton Compartment of Intestinal Membranes", *Int. J. Biochem.,* 1993, 25, 557–566.

Hardingham, J.E., et al., "Immunobead–PCR: A Technique for the Detection of Circulating Tumor Cells Using Immunomagnetic Beads and the Polymerase Chain Reaction", *Cancer Research,* 1993, 53, 3455–3458.

Hugues, et al., "Identification and Characterization of a New Family of High–Affinity Receptors for *Escherichia coli* Heat–Stable Enterotoxin in Rat Intestinal Membranes", *Biochemistry,* 1991, 30, 10738–10745.

Kaplan, J.C. et al., "Illegitimate transcription: its use in the study of inherited disease", *Human Mutation,* 1992, 1(5), 357–360 (Abstract only).

Negrier, C. et al., "Illegitimate transcription: its use for studying genetic abnormalities in lymphoblastoid cells from patients with Glanzmann thrombasthenia", *British J. Haematology,* 1998, 100(1), 33–39.

Thompson, M.R., "*Escherichia coli* Heat–Stable Enterotoxins and Their Receptors", *Pathol. Immunopathol. Res.,* 1987, 6, 103–116.

Zippelius, A. et al., "Limitations of Reverse–Transcriptase Polymerase Chain Reaction Analyses for Detection of Micrometastatic Epithelial Cancer Cells in Bone Marrow", *J. Clin. Oncology,* 1997, 15(7), 2701–2708.

FIGURE

```
TGGAGTGGGCTGAGGGACTCCACTAGAGGCTGTCCATCTGGATTCCCTGCCTCCCTAGGAGCCCAACAGAGCAAAGCAAG
TGGGCACAAGGAGTATGGTTCTAACGTGATTGGGGTCATGAAGACGTTGCTGTTGGACTTGGCTTTGTGGTCACTGCTCT
TCCAGCCCGGGTGGCTGTCCTTTAGTTCCCAGGTGAGTCAGAACTGCCACAATGGCAGCTATGAAATCAGCGTCCTGATG
ATGGGCAACTCAGCCTTTGCAGAGCCCCTGAAAACTTGGAAGATGCGGTGAATGAGGGCTGGAAATAGTGAGAGGACG
TCTGCAAATGCTGGCCTAAATGTGACTGTGAACGCTACTTTCATGTATTCGGATGGTCTGATTCATAACTCAGGCGACT
GCCGGAGTAGCACCTGTGAAGGCCTCGACCTACTCAGGAAAATTTCAAATGCACAACGGATGGGCTGTGTCCTCATAGGG
CCCTCATGTACATACTCCACCTTCCAGATGTACCTTGACACAGAATTGAGCTACCCCATGATCTCAGCTGGAAGTTTTGG
ATTGTCATGTGACTATAAAGAAACCTTAACCAGGCTGATGTCTCCAGCTAGAAAGTTGATGTACTTCTTGGTTAACTTTT
GGAAAAACCAACGATCTGCCCTTCAAAACTTATTCCTGGAGCACTTCGTATGTTTACAAGAATGGTACAGAAACTGAGGAC
TGTTTCTGGTACCTTAATGCTCTGGAGGCTAGCGTTTCCTATTTCTCCCACGAACTCGGCTTTAAGGTGGTGTTAAGACA
AGATAAGGAGTTTCAGGATATCTTAATGGACCACAACAGGAAAAGCAATGTGATTATTATGTGTGGTGGTCCAGAGTTCC
TCTACAAGCTGAAGGGTGACCGAGCAGTGGCTGAAGACATTGTCATTATTCTAGTGGATCTTTTCAATGACCAGTACTTG
GAGGACAATGTCACAGCCCCTGACTATATGAAAAATGTCCTTGTTCTGACGCTGTCTCCTGGGAATTCCCTTCTAAATAG
CTCTTTCTCCAGGAATCTATCACCAACAAAACGAGACTTTCGTCTTGCCTATTTGAATGGAATCCTCGTCTTTGGACATA
TGCTGAAGATATTTCTTGAAAATGGAGAAAATATTACCACCCCCAAATTTGCTCATGCCTTCAGGAATCTCACTTTTGAA
GGGTATGACGGTCCAGTGACCTTGGATGACTGGGGGGATGTTGACAGTACCATGGTGCTTCTGTATACCTCTGTGGACAC
CAAGAAATACAAGGTTCTTTTGACCTATGATACCCACGTAAATAAGACCTATCCTGTGGATATGAGCCCCACATTCACTT
GGAAGAACTCTAAACTTCCTAATGATATTACAGGCCGGGGCCCTCAGATCCTGATGATTGCAGTCTTCACCCTCACTGGA
GCTGTGGTGCTGCTCCTGCTCGTCGCTCTCCTGATGCTCAGAAAATATAGAAAAGATTATGAACTTCGTCAGAAAAAATG
GTCCCACATTCCTCCTGAAAATATCTTTCCTCTGGAGACCAATGAGACCAATCATGTTAGCCTCAAGATCGATGATGACA
AAAGACGAGATACAATCCAGAGACTACGACAGTGCAAATACGTCAAAAAGCGAGTGATTCTCAAAGATCTCAAGCACAAT
GATGGTAATTTCACTGAAAAACAGAAGATAGAATTGAACAAGTTGCTTCAGATTGACTATTACACCCTAACCAAGTTCTA
CGGGACAGTGAAACTGGATACCATGATCTTCGGGGTGATAGAATACTGTGAGAGAGGATCCCTCCGGGAAGTTTTAAATG
ACACAATTTCCTACCCTGATGGCACATTCATGGATTGGGAGTTTAAGATCTCTGTCTTGTATGACATTGCTAAGGGAATG
TCATATCTGCACTCCAGTAAGACAGAAGTCCATGGTCGTCTGAAATCTACCAACTGCGTAGTGGACAGTAGAATGGTGGT
GAAGATCACTGATTTTGGCTGCAATTCCATTTTGCCTCCAAAAAAGGACCTGTGGACAGCTCCAGAGCACCTCCGCCAAG
CCAACATCTCTCAGAAAGGAGATGTGTACAGCTATGGGATCATCGCACAGGAGATCATTCTGCGGAAAGAAACCTTCTAC
ACTTTGAGCTGTCGGGACCGGAATGAGAAGATTTTCAGAGTGGAAAATTCCAATGGAATGAAACCCTTCCGCCCAGATTT
ATTCTTGGAAACAGCAGAGGAAAAAGAGCTAGAAGTGTACCTACTTGTAAAAAACTGTTGGGAGGAAGATCCAGAAAAGA
GACCAGATTTCAAAAAAATTGAGACTACACTTGCCAAGATATTTGGACTTTTTCATGACCAAAAAAATGAAAGCTATATG
GATACCTTGATCCGACGTCTACAGCTATATTCTCGAAACCTGGAACATCTGGTAGAGGGAAAGGACACAGCTGTACAAGGC
AGAGAGGGACAGGGCTGACAGACTTAACTTTATGTTGCTTCCAAGGCTAGTGGTAAAGTCTCTGAAGGAGAAAGGCTTTG
TGGAGCCGGAACTATATGAGGAAGTTACAATCTACTTCAGTGACATTGTAGGTTTCACTACTATCTGCAAATACAGCACC
CCCATGGAAGTGGTGGACATGCTTAATGACATCTATAAGAGTTTTGACCACATTGTTGATCATCATGATGTCTACAAGGT
GGAAACCATCGGTGATGCGTACATGGTGGCTAGTGGTTTGCCTAAGAGAAATGGCAATCGGCATGCAATAGACATTGCCA
AGATGGCCTTGGAAATCCTCAGCTTCATGGGGACCTTTGAGCTGGAGCATCTTCCTGGCCTCCCAATATGGATTCGCATT
GGAGTTCACTCTGGTCCCTGTGCTGCTGGAGTTGTGGGAATCAAGATGCCTCGTTATTGTCTATTTGGAGATACGGTCAA
CACAGCCTCTAGGATGGAATCCACTGGCCTCCCTTTGAGAATTCACGTGAGTGGCTCCACCATAGCCATCCTGAAGAGAA
CTGAGTGCCAGTTCCTTTATGAAGTGAGAGGAGAAACATACTTAAAGGGAAGAGGAAATGAGACTACCTACTGGCTGACT
GGGATGAAGGACCAGAAATTCAACCTGCCAACCCCTCCTACTGTGGAGAATCAACAGCGTTTGCAAGCAGAATTTTCAGA
CATGATTGCCAACTCTTTACAGAAAAGACAGGCAGCAGGGATAAGAAGCCAAAAACCCAGACGGGTAGCCAGCTATAAAA
AAGGCACTCTGGAATACTTGCAGCTGAATACCACAGACAAGGAGAGCACCTATTTTTAAACCTAAATGAGGTATAAGGAC
TCACACAAATTAAAATACAGCTGCACTGAGGCCAGGCACCCTCAGGTGTCCTGAAAGCTTACTTTCCTGAGACCTCATGA
GGCAGAAATGTCTTAGGCTTGGCTGCCCTGTTTGGACCATGGACTTTCTTTGCATGAATCAGATGTGTTCTCAGTGAAAT
AACTACCTTCCACTCTGGAACCTTATTCCAGCAGTTGTTCCAGGGAGCTTCTACCTGGAAAAGAAAAGAATTTCATTTAT
TTTTTGTTTGTTTATTTTTATCGTTTTTGTTTACTGGCTTTCCTTCTGTATTCATAAGATTTTTTAAATTGTCATAATTA
TATTTTAAATACCCATCTTCATTAAAGTATATTTAACTCATAATTTTTGCAGAAAATATGCTATATATTAGGCAAGAATA
AAAGCTAAAGGTTTCCCAAAAAAAAAA
```

Gray Shaded Area -- This is the portion of the sequence that is deleted. One of the boxed G pairs is also deleted.

♯ Start Codon

^ The boxed G nucleotides are to indicate that a pair of G's are deleted. It is difficult to identify which pair is deleted since there are two G nucleotides at the beginning and end of the deleted region.

SEQUENCE LISTING (1) GENERAL INFORMATION:

(iii) NUMBER OF SEQUENCES: 85

(2) INFORMATION FOR SEQ ID NO:1:

(i) SEQUENCE CHARACTERISTICS:
      (A) LENGTH: 1636 bases
      (B) TYPE: nucleic acid
      (C) STRANDEDNESS: single
      (D) TOPOLOGY: linear (xi) SEQUENCE DESCRIPTION: SEQ ID NO:1:

```
GGGCACAAGG AGTATGGTTC TAACGTGATT GGGGTCATGA AGACGTTGCT GTTGGACTTG      60

GCTTTGTGGT CACTGCTCTT CCATCCCGGG TGGCTGTCCT TTAGTTCCCA GGCCTAAATG     120

TGACTGTGAA CGCTACTTTC ATGTATTCGG ATGGTCTGAT TCATAACTCA GGCGACTGCC     180

GGAGTAGCAC CTGTGAAGGC CTCGACCTAC TCAGGAAAAT TTCAAATGCA CAACGGATGG     240

GCTGTGTCCT CATAGGGCCC TCATGTACAT ACTCCACCTT CCAGATGTAC CTTGACACAG     300

AATTGAGCTA CCCCATGATC TCAGCTGGAA GTTTTGGATT GTCATGTGAC TATAAAGAAA     360

CCTTAACCAG GCTGATGTCT CCAGCTAGAA AGTTGATATA CTTCTTGGTT AACTTTTGGA     420

AAACCAACGA TCTGCCCTTC AAAACTTATT CCTGGAGCAC TTCGTATGTT TACAAGAATG     480

GTACAGAAAC TGAGGGACTG TTTCTGGTAC CTTAATGCTC TGGAGGCTAG CGTTTCCTAT     540

TTCTCCCACG AACTCGGCTT TAAGGTGGTG TTAAGACAAG ATAAGGAGTT TCAGGATATC     600

TTAATGGACC ACAACAGGAA AAGCAATGTG ATTATTATGT GTGGTGGTCC AGAGTTCCTC     660

TACAAGCTGA AGGGTGACCG AGCAGTGGCT GAAGACATTG TCATTATTCT AGTGGATCTT     720

TTCAATGACC AGTACTTGGA GGACAATGTC ACAGCCCCTG ACTATATGAA AAATGTCCTT     780

GTTCTGACGC TGTCTCCTGG GGAATTCCCT TCTAAATAGC TCTTTCTCCA GGAATCTATC     840

ACCAACAAAA CGAGACTTTG CTCTTGCCTA TTTGAATGGA ATCCTGCTCT TTGGACATAT     900

GCTGAAGATA TTTCTTGAAA ATGGAGAAAA TATTACCACC CCCAAATTTG CTCATGCTTT     960

CAGGAATCTC ACTTTTGAAG GGTATGACGG TCCAGTGACC TTGGGATGAC TGGGGGGATG    1020

TTGACAGTAC CATGGTGCTT CCGTTATACC CTCTGTGGAC ACCAAGAAAT ACAAGGTTCT    1080

TTGGACCTAT GATACCCACG TTAATAAGAA CTATCCTGTG GATATGAGCC CCACATTCAC    1140

TTGGAAGAAC TCTAAACTTC CTAATGATAT TACAGGCCGG GGCCCTCAGA TCCTGATGAT    1200

TGCAGTCTTC ACCCTCACTG GAGCTGTGGT GCTGCTCCTG CTCGTCGCTC TCCTGATGCT    1260

CAGAAAATAT AGAAAAGATT ATGAACTTCG TCAGAAAAAA TGGTCCCACA TTCCTCCTGA    1320

AAATATCTTT CCTCTGGAGA CCAATGAGAC CAATCATGTT AGCCTCAAGA TCGATGATGA    1380

CAAAAGACGA GATACAATCC AGAGACTACG ACAGTGCAAA TACGACAAAA AGCGAGTGAT    1440

TCTCAAAGAT CTCAAGCACA ATGATGGTAA TTTCACTGAA AAACAGAAGA TAGAATTGAA    1500

CAAGTTGCTT CAGAAAGACT ATTACAACCT GACCAAGTTC TACGGCACAG TGAAACTTGA    1560

TACCATGATC TTCGGGGTGA TAGAATACTG TGAGAGAGGA TCCCCTCCGG GAAGTTTTAA    1620

ATGACACAAT TTCCTA                                                   1636
```

(2) INFORMATION FOR SEQ ID NO:2:

(i) SEQUENCE CHARACTERISTICS:
        (A) LENGTH: 78 base pairs
        (B) TYPE: nucleic acid
        (C) STRANDEDNESS: double
        (D) TOPOLOGY: linear (xi) SEQUENCE DESCRIPTION: SEQ ID NO:2:

```
ATG AAG ACG TTG CTG TTG GAC TTG GCT TTG TGG TCA CTG CTC TTC          45
Met Lys Thr Leu Leu Leu Asp Leu Ala Leu Trp Ser Leu Leu Phe
 1               5                  10                  15

CAT CCC GGG TGG CTG TCC TTT AGT TCC CAG GCC                          78
His Pro Gly Trp Leu Ser Phe Ser Ser Gln Ala
                20                  25
```

(2) INFORMATION FOR SEQ ID NO:3:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO:3:

```
Met Lys Thr Leu Leu Leu Asp Leu Ala Leu Trp Ser Leu Leu Phe
 1               5                  10                  15

His Pro Gly Trp Leu Ser Phe Ser Ser Gln Ala
                20                  25
```

(2) INFORMATION FOR SEQ ID NO:4:

(i) SEQUENCE CHARACTERISTICS:
        (A) LENGTH: 372 base pairs
        (B) TYPE: nucleic acid
        (C) STRANDEDNESS: double
        (D) TOPOLOGY: linear (xi) SEQUENCE DESCRIPTION: SEQ ID NO:4:

```
ATG TAT TCG GAT GGT CTG ATT CAT AAC TCA GGC GAC TGC CGG AGT          45
Met Tyr Ser Asp Gly Leu Ile His Asn Ser Gly Asp Cys Arg Ser
 1               5                  10                  15

AGC ACC TGT GAA GGC CTC GAC CTA CTC AGG AAA ATT TCA AAT GCA          90
Ser Thr Cys Glu Gly Leu Asp Leu Leu Arg Lys Ile Ser Asn Ala
                20                  25                  30

CAA CGG ATG GGC TGT GTC CTC ATA GGG CCC TCA TGT ACA TAC TCC         135
Gln Arg Met Gly Cys Val Leu Ile Gly Pro Ser Cys Thr Tyr Ser
                35                  40                  45

ACC TTC CAG ATG TAC CTT GAC ACA GAA TTG AGC TAC CCC ATG ATC         180
Thr Phe Gln Met Tyr Leu Asp Thr Glu Leu Ser Tyr Pro Met Ile
                50                  55                  60

TCA GCT GGA AGT TTT GGA TTG TCA TGT GAC TAT AAA GAA ACC TTA         225
Ser Ala Gly Ser Phe Gly Leu Ser Cys Asp Tyr Lys Glu Thr Leu
                65                  70                  75

ACC AGG CTG ATG TCT CCA GCT AGA AAG TTG ATA TAC TTC TTG GTT         270
Thr Arg Leu Met Ser Pro Ala Arg Lys Leu Ile Tyr Phe Leu Val
                80                  85                  90

AAC TTT TGG AAA ACC AAC GAT CTG CCC TTC AAA ACT TAT TCC TGG         315
Asn Phe Trp Lys Thr Asn Asp Leu Pro Phe Lys Thr Tyr Ser Trp
                95                  100                 105

AGC ACT TCG TAT GTT TAC AAG AAT GGT ACA GAA ACT GAG GGA CTG         360
Ser Thr Ser Tyr Val Tyr Lys Asn Gly Thr Glu Thr Glu Gly Leu
```

```
                   110                 115                 120
TTT CTG GTA CCT                                                               372
Phe Leu Val Pro (2) INFORMATION FOR SEQ ID NO:5:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO:5:

Met Tyr Ser Asp Gly Leu Ile His Asn Ser Gly Asp Cys Arg Ser
  1               5                  10                  15

Ser Thr Cys Glu Gly Leu Asp Leu Leu Arg Lys Ile Ser Asn Ala
                 20                  25                  30

Gln Arg Met Gly Cys Val Leu Ile Gly Pro Ser Cys Thr Tyr Ser
                 35                  40                  45

Thr Phe Gln Met Tyr Leu Asp Thr Glu Leu Ser Tyr Pro Met Ile
                 50                  55                  60

Ser Ala Gly Ser Phe Gly Leu Ser Cys Asp Tyr Lys Glu Thr Leu
                 65                  70                  75

Thr Arg Leu Met Ser Pro Ala Arg Lys Leu Ile Tyr Phe Leu Val
                 80                  85                  90

Asn Phe Trp Lys Thr Asn Asp Leu Pro Phe Lys Thr Tyr Ser Trp
                 95                 100                 105

Ser Thr Ser Tyr Val Tyr Lys Asn Gly Thr Glu Thr Glu Gly Leu
                110                 115                 120

Phe Leu Val Pro (2) INFORMATION FOR SEQ ID NO:6:

(i) SEQUENCE CHARACTERISTICS:
        (A) LENGTH: 276 base pairs
        (B) TYPE: nucleic acid
        (C) STRANDEDNESS: double
        (D) TOPOLOGY: linear (xi) SEQUENCE DESCRIPTION: SEQ ID NO:6:

ATG GGC TGT GTC CTC ATA GGG CCC TCA TGT ACA TAC TCC ACC TTC       45
Met Gly Cys Val Leu Ile Gly Pro Ser Cys Thr Tyr Ser Thr Phe
  1               5                  10                  15

CAG ATG TAC CTT GAC ACA GAA TTG AGC TAC CCC ATG ATC TCA GCT       90
Gln Met Tyr Leu Asp Thr Glu Leu Ser Tyr Pro Met Ile Ser Ala
                 20                  25                  30

GGA AGT TTT GGA TTG TCA TGT GAC TAT AAA GAA ACC TTA ACC AGG      135
Gly Ser Phe Gly Leu Ser Cys Asp Tyr Lys Glu Thr Leu Thr Arg
                 35                  40                  45

CTG ATG TCT CCA GCT AGA AAG TTG ATA TAC TTC TTG GTT AAC TTT      180
Leu Met Ser Pro Ala Arg Lys Leu Ile Tyr Phe Leu Val Asn Phe
                 50                  55                  60

TGG AAA ACC AAC GAT CTG CCC TTC AAA ACT TAT TCC TGG AGC ACT      225
Trp Lys Thr Asn Asp Leu Pro Phe Lys Thr Tyr Ser Trp Ser Thr
                 65                  70                  75

TCG TAT GTT TAC AAG AAT GGT ACA GAA ACT GAG GGA CTG TTT CTG      270
Ser Tyr Val Tyr Lys Asn Gly Thr Glu Thr Glu Gly Leu Phe Leu
                 80                  85                  90

GTA CCT                                                          276
```

Val Pro (2) INFORMATION FOR SEQ ID NO:7:

(i) SEQUENCE CHARACTERISTICS:
        (A) LENGTH: 92 amino acids
        (B) TYPE: amino acid
        (D) TOPOLOGY: linear (ii) MOLECULE TYPE: protein (xi) SEQUENCE DESCRIPTION: SEQ ID NO:7:

```
Met Gly Cys Val Leu Ile Gly Pro Ser Cys Thr Tyr Ser Thr Phe
 1               5                  10                  15

Gln Met Tyr Leu Asp Thr Glu Leu Ser Tyr Pro Met Ile Ser Ala
            20                  25                  30

Gly Ser Phe Gly Leu Ser Cys Asp Tyr Lys Glu Thr Leu Thr Arg
            35                  40                  45

Leu Met Ser Pro Ala Arg Lys Leu Ile Tyr Phe Leu Val Asn Phe
            50                  55                  60

Trp Lys Thr Asn Asp Leu Pro Phe Lys Thr Tyr Ser Trp Ser Thr
            65                  70                  75

Ser Tyr Val Tyr Lys Asn Gly Thr Glu Thr Glu Gly Leu Phe Leu
            80                  85                  90

Val Pro
```

(2) INFORMATION FOR SEQ ID NO:8:

(i) SEQUENCE CHARACTERISTICS:
        (A) LENGTH: 228 base pairs
        (B) TYPE: nucleic acid
        (C) STRANDEDNESS: double
        (D) TOPOLOGY: linear (xi) SEQUENCE DESCRIPTION: SEQ ID NO:8:

```
ATG TAC CTT GAC ACA GAA TTG AGC TAC CCC ATG ATC TCA GCT GGA         45
Met Tyr Leu Asp Thr Glu Leu Ser Tyr Pro Met Ile Ser Ala Gly
 1               5                  10                  15

AGT TTT GGA TTG TCA TGT GAC TAT AAA GAA ACC TTA ACC AGG CTG         90
Ser Phe Gly Leu Ser Cys Asp Tyr Lys Glu Thr Leu Thr Arg Leu
            20                  25                  30

ATG TCT CCA GCT AGA AAG TTG ATA TAC TTC TTG GTT AAC TTT TGG        135
Met Ser Pro Ala Arg Lys Leu Ile Tyr Phe Leu Val Asn Phe Trp
            35                  40                  45

AAA ACC AAC GAT CTG CCC TTC AAA ACT TAT TCC TGG AGC ACT TCG        180
Lys Thr Asn Asp Leu Pro Phe Lys Thr Tyr Ser Trp Ser Thr Ser
            50                  55                  60

TAT GTT TAC AAG AAT GGT ACA GAA ACT GAG GGA CTG TTT CTG GTA        225
Tyr Val Tyr Lys Asn Gly Thr Glu Thr Glu Gly Leu Phe Leu Val
            65                  70                  75

CCT                                                                228
Pro
```

(2) INFORMATION FOR SEQ ID NO:9:

(i) SEQUENCE CHARACTERISTICS:
        (A) LENGTH: 76 amino acids
        (B) TYPE: amino acid
        (D) TOPOLOGY: linear (ii) MOLECULE TYPE: protein (xi) SEQUENCE DESCRIPTION: SEQ ID NO:9:

```
Met Tyr Leu Asp Thr Glu Leu Ser Tyr Pro Met Ile Ser Ala Gly
 1               5                  10                 15

Ser Phe Gly Leu Ser Cys Asp Tyr Lys Glu Thr Leu Thr Arg Leu
               20                  25                  30

Met Ser Pro Ala Arg Lys Leu Ile Tyr Phe Leu Val Asn Phe Trp
               35                  40                  45

Lys Thr Asn Asp Leu Pro Phe Lys Thr Tyr Ser Trp Ser Thr Ser
               50                  55                  60

Tyr Val Tyr Lys Asn Gly Thr Glu Thr Glu Gly Leu Phe Leu Val
               65                  70                  75

Pro
```

(2) INFORMATION FOR SEQ ID NO:10:

(i) SEQUENCE CHARACTERISTICS:
        (A) LENGTH: 198 base pairs
        (B) TYPE: nucleic acid
        (C) STRANDEDNESS: double
        (D) TOPOLOGY: linear (xi) SEQUENCE DESCRIPTION: SEQ ID NO:10:

```
ATG ATC TCA GCT GGA AGT TTT GGA TTG TCA TGT GAC TAT AAA GAA        45
Met Ile Ser Ala Gly Ser Phe Gly Leu Ser Cys Asp Tyr Lys Glu
 1               5                  10                  15

ACC TTA ACC AGG CTG ATG TCT CCA GCT AGA AAG TTG ATA TAC TTC        90
Thr Leu Thr Arg Leu Met Ser Pro Ala Arg Lys Leu Ile Tyr Phe
                20                  25                  30

TTG GTT AAC TTT TGG AAA ACC AAC GAT CTG CCC TTC AAA ACT TAT       135
Leu Val Asn Phe Trp Lys Thr Asn Asp Leu Pro Phe Lys Thr Tyr
                35                  40                  45

TCC TGG AGC ACT TCG TAT GTT TAC AAG AAT GGT ACA GAA ACT GAG       180
Ser Trp Ser Thr Ser Tyr Val Tyr Lys Asn Gly Thr Glu Thr Glu
                50                  55                  60

GGA CTG TTT CTG GTA CCT                                           198
Gly Leu Phe Leu Val Pro
                65
```

(2) INFORMATION FOR SEQ ID NO:11:

(i) SEQUENCE CHARACTERISTICS:
        (A) LENGTH: 66 amino acids
        (B) TYPE: amino acid
        (D) TOPOLOGY: linear (ii) MOLECULE TYPE: protein (xi) SEQUENCE DESCRIPTION: SEQ ID NO:11:

```
Met Ile Ser Ala Gly Ser Phe Gly Leu Ser Cys Asp Tyr Lys Glu
 1               5                  10                  15

Thr Leu Thr Arg Leu Met Ser Pro Ala Arg Lys Leu Ile Tyr Phe
                20                  25                  30

Leu Val Asn Phe Trp Lys Thr Asn Asp Leu Pro Phe Lys Thr Tyr
                35                  40                  45

Ser Trp Ser Thr Ser Tyr Val Tyr Lys Asn Gly Thr Glu Thr Glu
                50                  55                  60

Gly Leu Phe Leu Val Pro
                65
```

(2) INFORMATION FOR SEQ ID NO:12:

(i) SEQUENCE CHARACTERISTICS:
        (A) LENGTH: 138 base pairs
        (B) TYPE: nucleic acid
        (C) STRANDEDNESS: double
        (D) TOPOLOGY: linear (xi) SEQUENCE DESCRIPTION: SEQ ID NO:12:

```
ATG TCT CCA GCT AGA AAG TTG ATA TAC TTC TTG GTT AAC TTT TGG        45
Met Ser Pro Ala Arg Lys Leu Ile Tyr Phe Leu Val Asn Phe Trp
 1               5                  10                  15

AAA ACC AAC GAT CTG CCC TTC AAA ACT TAT TCC TGG AGC ACT TCG        90
Lys Thr Asn Asp Leu Pro Phe Lys Thr Tyr Ser Trp Ser Thr Ser
                20                  25                  30

TAT GTT TAC AAG AAT GGT ACA GAA ACT GAG GGA CTG TTT CTG GTA       135
Tyr Val Tyr Lys Asn Gly Thr Glu Thr Glu Gly Leu Phe Leu Val
                35                  40                  45

CCT                                                               138
Pro
```

(2) INFORMATION FOR SEQ ID NO:13:

(i) SEQUENCE CHARACTERISTICS:
        (A) LENGTH: 46 amino acids
        (B) TYPE: amino acid
        (D) TOPOLOGY: linear (ii) MOLECULE TYPE: protein (xi) SEQUENCE DESCRIPTION: SEQ ID NO:13:

```
Met Ser Pro Ala Arg Lys Leu Ile Tyr Phe Leu Val Asn Phe Trp
 1               5                  10                  15

Lys Thr Asn Asp Leu Pro Phe Lys Thr Tyr Ser Trp Ser Thr Ser
                20                  25                  30

Tyr Val Tyr Lys Asn Gly Thr Glu Thr Glu Gly Leu Phe Leu Val
                35                  40                  45

Pro
```

(2) INFORMATION FOR SEQ ID NO:14:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (xi) SEQUENCE DESCRIPTION: SEQ ID NO:14:

```
ATG CAC AAC GGA TGG GCT GTG TCC TCA                                27
Met His Asn Gly Trp Ala Val Ser Ser
 1               5
```

(2) INFORMATION FOR SEQ ID NO:15:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:15:

```
Met His Asn Gly Trp Ala Val Ser Ser
 1               5
```

(2) INFORMATION FOR SEQ ID NO:16:

(i) SEQUENCE CHARACTERISTICS:
       (A) LENGTH: 30 base pairs
       (B) TYPE: nucleic acid
       (C) STRANDEDNESS: double
       (D) TOPOLOGY: linear (xi) SEQUENCE DESCRIPTION: SEQ ID NO:16:

```
ATG TAC ATA CTC CAC CTT CCA GAT GTA CCT                          30
Met Tyr Ile Leu His Leu Pro Asp Val Pro
1               5                   10
```

(2) INFORMATION FOR SEQ ID NO:17:

(i) SEQUENCE CHARACTERISTICS:
       (A) LENGTH: 10 amino acids
       (B) TYPE: amino acid
       (D) TOPOLOGY: linear (ii) MOLECULE TYPE: protein (xi) SEQUENCE DESCRIPTION: SEQ ID NO:17:

```
Met Tyr Ile Leu His Leu Pro Asp Val Pro
1               5                   10
```

(2) INFORMATION FOR SEQ ID NO:18:

(i) SEQUENCE CHARACTERISTICS:
       (A) LENGTH: 351 base pairs
       (B) TYPE: nucleic acid
       (C) STRANDEDNESS: double
       (D) TOPOLOGY: linear (xi) SEQUENCE DESCRIPTION: SEQ ID NO:18:

```
ATG TTT ACA AGA ATG GTA CAG AAA CTG AGG GAC TGT TTC TGG TAC      45
Met Phe Thr Arg Met Val Gln Lys Leu Arg Asp Cys Phe Trp Tyr
1               5                   10                  15

CTT AAT GCT CTG GAG GCT AGC GTT TCC TAT TTC TCC CAC GAA CTC      90
Leu Asn Ala Leu Glu Ala Ser Val Ser Tyr Phe Ser His Glu Leu
                20                  25                  30

GGC TTT AAG GTG GTG TTA AGA CAA GAT AAG GAG TTT CAG GAT ATC     135
Gly Phe Lys Val Val Leu Arg Gln Asp Lys Glu Phe Gln Asp Ile
                35                  40                  45

TTA ATG GAC CAC AAC AGG AAA AGC AAT GTG ATT ATT ATG TGT GGT     180
Leu Met Asp His Asn Arg Lys Ser Asn Val Ile Ile Met Cys Gly
                50                  55                  60

GGT CCA GAG TTC CTC TAC AAG CTG AAG GGT GAC CGA GCA GTG GCT     225
Gly Pro Glu Phe Leu Tyr Lys Leu Lys Gly Asp Arg Ala Val Ala
                65                  70                  75

GAA GAC ATT GTC ATT ATT CTA GTG GAT CTT TTC AAT GAC CAG TAC     270
Glu Asp Ile Val Ile Ile Leu Val Asp Leu Phe Asn Asp Gln Tyr
                80                  85                  90

TTG GAG GAC AAT GTC ACA GCC CCT GAC TAT ATG AAA AAT GTC CTT     315
Leu Glu Asp Asn Val Thr Ala Pro Asp Tyr Met Lys Asn Val Leu
                95                  100                 105

GTT CTG ACG CTG TCT CCT GGG GAA TTC CCT TCT AAA                 351
Val Leu Thr Leu Ser Pro Gly Glu Phe Pro Ser Lys
                110                 115
```

(2) INFORMATION FOR SEQ ID NO:19:

(i) SEQUENCE CHARACTERISTICS:
       (A) LENGTH: 117 amino acids
       (B) TYPE: amino acid
       (D) TOPOLOGY: linear (ii) MOLECULE TYPE: protein (xi) SEQUENCE DESCRIPTION: SEQ ID NO:19:

```
Met Phe Thr Arg Met Val Gln Lys Leu Arg Asp Cys Phe Trp Tyr
 1               5                  10                  15

Leu Asn Ala Leu Glu Ala Ser Val Ser Tyr Phe Ser His Glu Leu
                20                  25                  30

Gly Phe Lys Val Val Leu Arg Gln Asp Lys Glu Phe Gln Asp Ile
                35                  40                  45

Leu Met Asp His Asn Arg Lys Ser Asn Val Ile Ile Met Cys Gly
                50                  55                  60

Gly Pro Glu Phe Leu Tyr Lys Leu Lys Gly Asp Arg Ala Val Ala
                65                  70                  75

Glu Asp Ile Val Ile Ile Leu Val Asp Leu Phe Asn Asp Gln Tyr
                80                  85                  90

Leu Glu Asp Asn Val Thr Ala Pro Asp Tyr Met Lys Asn Val Leu
                95                 100                 105

Val Leu Thr Leu Ser Pro Gly Glu Phe Pro Ser Lys
               110                 115
```

(2) INFORMATION FOR SEQ ID NO:20:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (xi) SEQUENCE DESCRIPTION: SEQ ID NO:20:

```
ATG GTA CAG AAA CTG AGG GAC TGT TTC TGG TAC CTT AAT GCT CTG        45
Met Val Gln Lys Leu Arg Asp Cys Phe Trp Tyr Leu Asn Ala Leu
 1               5                  10                  15

GAG GCT AGC GTT TCC TAT TTC TCC CAC GAA CTC GGC TTT AAG GTG        90
Glu Ala Ser Val Ser Tyr Phe Ser His Glu Leu Gly Phe Lys Val
                20                  25                  30

GTG TTA AGA CAA GAT AAG GAG TTT CAG GAT ATC TTA ATG GAC CAC       135
Val Leu Arg Gln Asp Lys Glu Phe Gln Asp Ile Leu Met Asp His
                35                  40                  45

AAC AGG AAA AGC AAT GTG ATT ATT ATG TGT GGT GGT CCA GAG TTC       180
Asn Arg Lys Ser Asn Val Ile Ile Met Cys Gly Gly Pro Glu Phe
                50                  55                  60

CTC TAC AAG CTG AAG GGT GAC CGA GCA GTG GCT GAA GAC ATT GTC       225
Leu Tyr Lys Leu Lys Gly Asp Arg Ala Val Ala Glu Asp Ile Val
                65                  70                  75

ATT ATT CTA GTG GAT CTT TTC AAT GAC CAG TAC TTG GAG GAC AAT       270
Ile Ile Leu Val Asp Leu Phe Asn Asp Gln Tyr Leu Glu Asp Asn
                80                  85                  90

GTC ACA GCC CCT GAC TAT ATG AAA AAT GTC CTT GTT CTG ACG CTG       315
Val Thr Ala Pro Asp Tyr Met Lys Asn Val Leu Val Leu Thr Leu
                95                 100                 105

TCT CCT GGG GAA TTC CCT TCT AAA                                   339
Ser Pro Gly Glu Phe Pro Ser Lys
               110
```

(2) INFORMATION FOR SEQ ID NO:21:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO:21:

Met Val Gln Lys Leu Arg Asp Cys Phe Trp Tyr Leu Asn Ala Leu
 1               5                  10                  15

Glu Ala Ser Val Ser Tyr Phe Ser His Glu Leu Gly Phe Lys Val
                20                  25                  30

Val Leu Arg Gln Asp Lys Glu Phe Gln Asp Ile Leu Met Asp His
                35                  40                  45

Asn Arg Lys Ser Asn Val Ile Ile Met Cys Gly Gly Pro Glu Phe
                50                  55                  60

Leu Tyr Lys Leu Lys Gly Asp Arg Ala Val Ala Glu Asp Ile Val
                65                  70                  75

Ile Ile Leu Val Asp Leu Phe Asn Asp Gln Tyr Leu Glu Asp Asn
                80                  85                  90

Val Thr Ala Pro Asp Tyr Met Lys Asn Val Leu Val Leu Thr Leu
                95                 100                 105

Ser Pro Gly Glu Phe Pro Ser Lys
               110

(2) INFORMATION FOR SEQ ID NO:22:

(i) SEQUENCE CHARACTERISTICS:
        (A) LENGTH: 213 base pairs
        (B) TYPE: nucleic acid
        (C) STRANDEDNESS: double
        (D) TOPOLOGY: linear (xi) SEQUENCE DESCRIPTION: SEQ ID NO:22:

ATG GAC CAC AAC AGG AAA AGC AAT GTG ATT ATT ATG TGT GGT GGT        45
Met Asp His Asn Arg Lys Ser Asn Val Ile Ile Met Cys Gly Gly
 1               5                  10                  15

CCA GAG TTC CTC TAC AAG CTG AAG GGT GAC CGA GCA GTG GCT GAA        90
Pro Glu Phe Leu Tyr Lys Leu Lys Gly Asp Arg Ala Val Ala Glu
                20                  25                  30

GAC ATT GTC ATT ATT CTA GTG GAT CTT TTC AAT GAC CAG TAC TTG       135
Asp Ile Val Ile Ile Leu Val Asp Leu Phe Asn Asp Gln Tyr Leu
                35                  40                  45

GAG GAC AAT GTC ACA GCC CCT GAC TAT ATG AAA AAT GTC CTT GTT       180
Glu Asp Asn Val Thr Ala Pro Asp Tyr Met Lys Asn Val Leu Val
                50                  55                  60

CTG ACG CTG TCT CCT GGG GAA TTC CCT TCT AAA                       213
Leu Thr Leu Ser Pro Gly Glu Phe Pro Ser Lys
                65                  70

(2) INFORMATION FOR SEQ ID NO:23:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO:23:

Met Asp His Asn Arg Lys Ser Asn Val Ile Ile Met Cys Gly Gly
 1               5                  10                  15

Pro Glu Phe Leu Tyr Lys Leu Lys Gly Asp Arg Ala Val Ala Glu
                20                  25                  30

Asp Ile Val Ile Ile Leu Val Asp Leu Phe Asn Asp Gln Tyr Leu
                35                  40                  45

```
Glu Asp Asn Val Thr Ala Pro Asp Tyr Met Lys Asn Val Leu Val
            50                  55                  60

Leu Thr Leu Ser Pro Gly Glu Phe Pro Ser Lys
            65                  70
```

(2) INFORMATION FOR SEQ ID NO:24:

(i) SEQUENCE CHARACTERISTICS:
        (A) LENGTH: 180 base pairs
        (B) TYPE: nucleic acid
        (C) STRANDEDNESS: double
        (D) TOPOLOGY: linear (xi) SEQUENCE DESCRIPTION: SEQ ID NO:24:

```
ATG TGT GGT GGT CCA GAG TTC CTC TAC AAG CTG AAG GGT GAC CGA        45
Met Cys Gly Gly Pro Glu Phe Leu Tyr Lys Leu Lys Gly Asp Arg
 1               5                  10                  15

GCA GTG GCT GAA GAC ATT GTC ATT ATT CTA GTG GAT CTT TTC AAT        90
Ala Val Ala Glu Asp Ile Val Ile Ile Leu Val Asp Leu Phe Asn
            20                  25                  30

GAC CAG TAC TTG GAG GAC AAT GTC ACA GCC CCT GAC TAT ATG AAA       135
Asp Gln Tyr Leu Glu Asp Asn Val Thr Ala Pro Asp Tyr Met Lys
            35                  40                  45

AAT GTC CTT GTT CTG ACG CTG TCT CCT GGG GAA TTC CCT TCT AAA       180
Asn Val Leu Val Leu Thr Leu Ser Pro Gly Glu Phe Pro Ser Lys
            50                  55                  60
```

(2) INFORMATION FOR SEQ ID NO:25:

(i) SEQUENCE CHARACTERISTICS:
        (A) LENGTH: 60 amino acids
        (B) TYPE: amino acid
        (D) TOPOLOGY: linear (ii) MOLECULE TYPE: protein (xi) SEQUENCE DESCRIPTION: SEQ ID NO:25:

```
Met Cys Gly Gly Pro Glu Phe Leu Tyr Lys Leu Lys Gly Asp Arg
 1               5                  10                  15

Ala Val Ala Glu Asp Ile Val Ile Ile Leu Val Asp Leu Phe Asn
            20                  25                  30

Asp Gln Tyr Leu Glu Asp Asn Val Thr Ala Pro Asp Tyr Met Lys
            35                  40                  45

Asn Val Leu Val Leu Thr Leu Ser Pro Gly Glu Phe Pro Ser Lys
            50                  55                  60
```

(2) INFORMATION FOR SEQ ID NO:26:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (xi) SEQUENCE DESCRIPTION: SEQ ID NO:26:

```
ATG AAA AAT GTC CTT GTT CTG ACG CTG TCT CCT GGG GAA TTC CCT        45
Met Lys Asn Val Leu Val Leu Thr Leu Ser Pro Gly Glu Phe Pro
 1               5                  10                  15

TCT AAA                                                            51
Ser Lys
```

(2) INFORMATION FOR SEQ ID NO:27:

(i) SEQUENCE CHARACTERISTICS:

```
       (A) LENGTH: 17 amino acids
       (B) TYPE: amino acid
       (D) TOPOLOGY: linear (ii) MOLECULE TYPE: protein (xi) SEQUENCE DESCRIPTION: SEQ ID NO:27:

Met Lys Asn Val Leu Val Leu Thr Leu Ser Pro Gly Glu Phe Pro
 1               5                  10                  15

Ser Lys (2) INFORMATION FOR SEQ ID NO:28:

(i) SEQUENCE CHARACTERISTICS:
       (A) LENGTH: 57 base pairs
       (B) TYPE: nucleic acid
       (C) STRANDEDNESS: double
       (D) TOPOLOGY: linear (xi) SEQUENCE DESCRIPTION: SEQ ID NO:28:

ATG CTC TGG AGG CTA GCG TTT CCT ATT TCT CCC ACG AAC TCG GCT         45
Met Leu Trp Arg Leu Ala Phe Pro Ile Ser Pro Thr Asn Ser Ala
 1               5                  10                  15

TTA AGG TGG TGT                                                     57
Leu Arg Trp Cys (2) INFORMATION FOR SEQ ID NO:29:

(i) SEQUENCE CHARACTERISTICS:
       (A) LENGTH: 19 amino acids
       (B) TYPE: amino acid
       (D) TOPOLOGY: linear (ii) MOLECULE TYPE: protein (xi) SEQUENCE DESCRIPTION: SEQ ID NO:29:

Met Leu Trp Arg Leu Ala Phe Pro Ile Ser Pro Thr Asn Ser Ala
 1               5                  10                  15

Leu Arg Trp Cys (2) INFORMATION FOR SEQ ID NO:30:

(i) SEQUENCE CHARACTERISTICS:
       (A) LENGTH: 42 base pairs
       (B) TYPE: nucleic acid
       (C) STRANDEDNESS: double
       (D) TOPOLOGY: linear (xi) SEQUENCE DESCRIPTION: SEQ ID NO:30:

ATG ACC AGT ACT TGG AGG ACA ATG TCA CAG CCC CTG ACT ATA             42
Met Thr Ser Thr Trp Arg Thr Met Ser Gln Pro Leu Thr Ile
 1               5                  10

(2) INFORMATION FOR SEQ ID NO:31:

(i) SEQUENCE CHARACTERISTICS:
       (A) LENGTH: 14 amino acids
       (B) TYPE: amino acid
       (D) TOPOLOGY: linear (ii) MOLECULE TYPE: protein (xi) SEQUENCE DESCRIPTION: SEQ ID NO:31:

Met Thr Ser Thr Trp Arg Thr Met Ser Gln Pro Leu Thr Ile
 1               5                  10
```

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (xi) SEQUENCE DESCRIPTION: SEQ ID NO:32:

```
ATG TCA CAG CCC CTG ACT ATA                                         21
Met Ser Gln Pro Leu Thr Ile
 1               5
```

(2) INFORMATION FOR SEQ ID NO:33:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:33:

```
Met Ser Gln Pro Leu Thr Ile
 1               5
```

(2) INFORMATION FOR SEQ ID NO:34:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (xi) SEQUENCE DESCRIPTION: SEQ ID NO:34:

```
ATG GAA TCC TGC TCT TTG GAC ATA TGC                                 27
Met Glu Ser Cys Ser Leu Asp Ile Cys
 1               5
```

(2) INFORMATION FOR SEQ ID NO:35:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:35:

```
Met Glu Ser Cys Ser Leu Asp Ile Cys
 1               5
```

(2) INFORMATION FOR SEQ ID NO:36:

(i) SEQUENCE CHARACTERISTICS:
        (A) LENGTH: 108 base pairs
        (B) TYPE: nucleic acid
        (C) STRANDEDNESS: double
        (D) TOPOLOGY: linear (xi) SEQUENCE DESCRIPTION: SEQ ID NO:36:

```
ATG CTG AAG ATA TTT CTT GAA AAT GGA GAA AAT ATT ACC ACC CCC         45
Met Leu Lys Ile Phe Leu Glu Asn Gly Glu Asn Ile Thr Thr Pro
 1               5                   10                  15

AAA TTT GCT CAT GCT TTC AGG AAT CTC ACT TTT GAA GGG TAT GAC         90
Lys Phe Ala His Ala Phe Arg Asn Leu Thr Phe Glu Gly Tyr Asp
                20                  25                  30

GGT CCA GTG ACC TTG GGA                                            108
```

```
Gly Pro Val Thr Leu Gly
            35

(2) INFORMATION FOR SEQ ID NO:37:

(i) SEQUENCE CHARACTERISTICS:
        (A) LENGTH: 36 amino acids
        (B) TYPE: amino acid
        (D) TOPOLOGY: linear (ii) MOLECULE TYPE: protein (xi) SEQUENCE DESCRIPTION: SEQ ID NO:37:

Met Leu Lys Ile Phe Leu Glu Asn Gly Glu Asn Ile Thr Thr Pro
 1               5                  10                  15

Lys Phe Ala His Ala Phe Arg Asn Leu Thr Phe Glu Gly Tyr Asp
                20                  25                  30

Gly Pro Val Thr Leu Gly
            35

(2) INFORMATION FOR SEQ ID NO:38:

(i) SEQUENCE CHARACTERISTICS:
        (A) LENGTH: 75 base pairs
        (B) TYPE: nucleic acid
        (C) STRANDEDNESS: double
        (D) TOPOLOGY: linear (xi) SEQUENCE DESCRIPTION: SEQ ID NO:38:

ATG GAG AAA ATA TTA CCA CCC CCA AAT TTG CTC ATG CTT TCA GGA        45
Met Glu Lys Ile Leu Pro Pro Pro Asn Leu Leu Met Leu Ser Gly
 1               5                  10                  15

ATC TCA CTT TTG AAG GGT ATG ACG GTC CAG                           75
Ile Ser Leu Leu Lys Gly Met Thr Val Gln
                20                  25

(2) INFORMATION FOR SEQ ID NO:39:

(i) SEQUENCE CHARACTERISTICS:
        (A) LENGTH: 25 amino acids
        (B) TYPE: amino acid
        (D) TOPOLOGY: linear (ii) MOLECULE TYPE: protein (xi) SEQUENCE DESCRIPTION: SEQ ID NO:39:

Met Glu Lys Ile Leu Pro Pro Pro Asn Leu Leu Met Leu Ser Gly
 1               5                  10                  15

Ile Ser Leu Leu Lys Gly Met Thr Val Gln
                20                  25

(2) INFORMATION FOR SEQ ID NO:40:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (xi) SEQUENCE DESCRIPTION: SEQ ID NO:40:

ATG CTT TCA GGA ATC TCA CTT TTG AAG GGT ATG ACG GTC CAG            42
Met Leu Ser Gly Ile Ser Leu Leu Lys Gly Met Thr Val Gln
 1               5                  10

(2) INFORMATION FOR SEQ ID NO:41:
```

(i) SEQUENCE CHARACTERISTICS:
    (A) LENGTH: 14 amino acids
    (B) TYPE: amino acid
    (D) TOPOLOGY: linear (ii) MOLECULE TYPE: protein (xi) SEQUENCE DESCRIPTION: SEQ ID NO:41:

```
Met Leu Ser Gly Ile Ser Leu Leu Lys Gly Met Thr Val Gln
 1               5                  10
```

(2) INFORMATION FOR SEQ ID NO:42:

(i) SEQUENCE CHARACTERISTICS:
        (A) LENGTH: 84 base pairs
        (B) TYPE: nucleic acid
        (C) STRANDEDNESS: double
        (D) TOPOLOGY: linear (xi) SEQUENCE DESCRIPTION: SEQ ID NO:42:

```
ATG ACT GGG GGG ATG TTG ACA GTA CCA TGG TGC TTC CGT TAT ACC        45
Met Thr Gly Gly Met Leu Thr Val Pro Trp Cys Phe Arg Tyr Thr
 1               5                  10                  15

CTC TGT GGA CAC CAA GAA ATA CAA GGT TCT TTG GAC CTA                84
Leu Cys Gly His Gln Glu Ile Gln Gly Ser Leu Asp Leu
                 20                  25
```

(2) INFORMATION FOR SEQ ID NO:43:

(i) SEQUENCE CHARACTERISTICS:
        (A) LENGTH: 28 amino acids
        (B) TYPE: amino acid
        (D) TOPOLOGY: linear (ii) MOLECULE TYPE: protein (xi) SEQUENCE DESCRIPTION: SEQ ID NO:43:

```
Met Thr Gly Gly Met Leu Thr Val Pro Trp Cys Phe Arg Tyr Thr
 1               5                  10                  15

Leu Cys Gly His Gln Glu Ile Gln Gly Ser Leu Asp Leu
                 20                  25
```

(2) INFORMATION FOR SEQ ID NO:44:

(i) SEQUENCE CHARACTERISTICS:
        (A) LENGTH: 72 base pairs
        (B) TYPE: nucleic acid
        (C) STRANDEDNESS: double
        (D) TOPOLOGY: linear (xi) SEQUENCE DESCRIPTION: SEQ ID NO:44:

```
ATG TTG ACA GTA CCA TGG TGC TTC CGT TAT ACC CTC TGT GGA CAC        45
Met Leu Thr Val Pro Trp Cys Phe Arg Tyr Thr Leu Cys Gly His
 1               5                  10                  15

CAA GAA ATA CAA GGT TCT TTG GAC CTA                                72
Gln Glu Ile Gln Gly Ser Leu Asp Leu
                 20
```

(2) INFORMATION FOR SEQ ID NO:45:

(i) SEQUENCE CHARACTERISTICS:
        (A) LENGTH: 24 amino acids
        (B) TYPE: amino acid
        (D) TOPOLOGY: linear (ii) MOLECULE TYPE: protein (xi) SEQUENCE DESCRIPTION: SEQ ID NO:45:

```
Met Leu Thr Val Pro Trp Cys Phe Arg Tyr Thr Leu Cys Gly His
1               5                  10                 15

Gln Glu Ile Gln Gly Ser Leu Asp Leu
                20
```

(2) INFORMATION FOR SEQ ID NO:46:

(i) SEQUENCE CHARACTERISTICS:
        (A) LENGTH: 93 base pairs
        (B) TYPE: nucleic acid
        (C) STRANDEDNESS: double
        (D) TOPOLOGY: linear (xi) SEQUENCE DESCRIPTION: SEQ ID NO:46:

```
ATG GTG CTT CCG TTA TAC CCT CTG TGG ACA CCA AGA AAT ACA AGG      45
Met Val Leu Pro Leu Tyr Pro Leu Trp Thr Pro Arg Asn Thr Arg
1               5                  10                 15

TTC TTT GGA CCT ATG ATA CCC ACG TTA ATA AGA ACT ATC CTG TGG      90
Phe Phe Gly Pro Met Ile Pro Thr Leu Ile Arg Thr Ile Leu Trp
                20                 25                 30

ATA                                                              93
Ile
```

(2) INFORMATION FOR SEQ ID NO:47:

(i) SEQUENCE CHARACTERISTICS:
        (A) LENGTH: 31 amino acids
        (B) TYPE: amino acid
        (D) TOPOLOGY: linear (ii) MOLECULE TYPE: protein (xi) SEQUENCE DESCRIPTION: SEQ ID NO:47:

```
Met Val Leu Pro Leu Tyr Pro Leu Trp Thr Pro Arg Asn Thr Arg
1               5                  10                 15

Phe Phe Gly Pro Met Ile Pro Thr Leu Ile Arg Thr Ile Leu Trp
                20                 25                 30

Ile
```

(2) INFORMATION FOR SEQ ID NO:48:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (xi) SEQUENCE DESCRIPTION: SEQ ID NO:48:

```
ATG ATA CCC ACG TTA ATA AGA ACT ATC CTG TGG ATA                  36
Met Ile Pro Thr Leu Ile Arg Thr Ile Leu Trp Ile
1               5                  10
```

(2) INFORMATION FOR SEQ ID NO:49:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:49:

```
Met Ile Pro Thr Leu Ile Arg Thr Ile Leu Trp Ile
1               5                  10
```

(2) INFORMATION FOR SEQ ID NO:50:

(i) SEQUENCE CHARACTERISTICS:
        (A) LENGTH: 498 base pairs
        (B) TYPE: nucleic acid
        (C) STRANDEDNESS: double
        (D) TOPOLOGY: linear (xi) SEQUENCE DESCRIPTION: SEQ ID NO:50:

```
ATG AGC CCC ACA TTC ACT TGG AAG AAC TCT AAA CTT CCT AAT GAT         45
Met Ser Pro Thr Phe Thr Trp Lys Asn Ser Lys Leu Pro Asn Asp
 1               5                  10                  15

ATT ACA GGC CGG GGC CCT CAG ATC CTG ATG ATT GCA GTC TTC ACC         90
Ile Thr Gly Arg Gly Pro Gln Ile Leu Met Ile Ala Val Phe Thr
                20                  25                  30

CTC ACT GGA GCT GTG GTG CTG CTC CTG CTC GTC GCT CTC CTG ATG        135
Leu Thr Gly Ala Val Val Leu Leu Leu Leu Val Ala Leu Leu Met
            35                  40                  45

CTC AGA AAA TAT AGA AAA GAT TAT GAA CTT CGT CAG AAA AAA TGG        180
Leu Arg Lys Tyr Arg Lys Asp Tyr Glu Leu Arg Gln Lys Lys Trp
        50                  55                  60

TCC CAC ATT CCT CCT GAA AAT ATC TTT CCT CTG GAG ACC AAT GAG        225
Ser His Ile Pro Pro Glu Asn Ile Phe Pro Leu Glu Thr Asn Glu
    65                  70                  75

ACC AAT CAT GTT AGC CTC AAG ATC GAT GAT GAC AAA AGA CGA GAT        270
Thr Asn His Val Ser Leu Lys Ile Asp Asp Asp Lys Arg Arg Asp
80                  85                  90

ACA ATC CAG AGA CTA CGA CAG TGC AAA TAC GAC AAA AAG CGA GTG        315
Thr Ile Gln Arg Leu Arg Gln Cys Lys Tyr Asp Lys Lys Arg Val
                95                 100                 105

ATT CTC AAA GAT CTC AAG CAC AAT GAT GGT AAT TTC ACT GAA AAA        360
Ile Leu Lys Asp Leu Lys His Asn Asp Gly Asn Phe Thr Glu Lys
            110                 115                 120

CAG AAG ATA GAA TTG AAC AAG TTG CTT CAG AAA GAC TAT TAC AAC        405
Gln Lys Ile Glu Leu Asn Lys Leu Leu Gln Lys Asp Tyr Tyr Asn
        125                 130                 135

CTG ACC AAG TTC TAC GGC ACA GTG AAA CTT GAT ACC ATG ATC TTC        450
Leu Thr Lys Phe Tyr Gly Thr Val Lys Leu Asp Thr Met Ile Phe
    140                 145                 150

GGG GTG ATA GAA TAC TGT GAG AGA GGA TCC CCT CCG GGA AGT TTT        495
Gly Val Ile Glu Tyr Cys Glu Arg Gly Ser Pro Pro Gly Ser Phe
155                 160                 165

AAA                                                                 498
Lys
```

(2) INFORMATION FOR SEQ ID NO:51:

(i) SEQUENCE CHARACTERISTICS:
        (A) LENGTH: 166 amino acids
        (B) TYPE: amino acid
        (D) TOPOLOGY: linear (ii) MOLECULE TYPE: protein (xi) SEQUENCE DESCRIPTION: SEQ ID NO:51:

```
Met Ser Pro Thr Phe Thr Trp Lys Asn Ser Lys Leu Pro Asn Asp
 1               5                  10                  15

Ile Thr Gly Arg Gly Pro Gln Ile Leu Met Ile Ala Val Phe Thr
                20                  25                  30

Leu Thr Gly Ala Val Val Leu Leu Leu Leu Val Ala Leu Leu Met
            35                  40                  45
```

```
Leu Arg Lys Tyr Arg Lys Asp Tyr Glu Leu Arg Gln Lys Lys Trp
            50                   55                   60

Ser His Ile Pro Pro Glu Asn Ile Phe Pro Leu Glu Thr Asn Glu
            65                   70                   75

Thr Asn His Val Ser Leu Lys Ile Asp Asp Lys Arg Arg Asp
            80                   85                   90

Thr Ile Gln Arg Leu Arg Gln Cys Lys Tyr Asp Lys Lys Arg Val
            95                  100                  105

Ile Leu Lys Asp Leu Lys His Asn Asp Gly Asn Phe Thr Glu Lys
           110                  115                  120

Gln Lys Ile Glu Leu Asn Lys Leu Leu Gln Lys Asp Tyr Tyr Asn
           125                  130                  135

Leu Thr Lys Phe Tyr Gly Thr Val Lys Leu Asp Thr Met Ile Phe
           140                  145                  150

Gly Val Ile Glu Tyr Cys Glu Arg Gly Ser Pro Pro Gly Ser Phe
           155                  160                  165

Lys (2) INFORMATION FOR SEQ ID NO:52:

(i) SEQUENCE CHARACTERISTICS:
        (A) LENGTH: 426 base pairs
        (B) TYPE: nucleic acid
        (C) STRANDEDNESS: double
        (D) TOPOLOGY: linear (xi) SEQUENCE DESCRIPTION: SEQ ID NO:52:

ATG ATT GCA GTC TTC ACC CTC ACT GGA GCT GTG GTG CTG CTC CTG         45
Met Ile Ala Val Phe Thr Leu Thr Gly Ala Val Val Leu Leu Leu
 1               5                  10                  15

CTC GTC GCT CTC CTG ATG CTC AGA AAA TAT AGA AAA GAT TAT GAA         90
Leu Val Ala Leu Leu Met Leu Arg Lys Tyr Arg Lys Asp Tyr Glu
            20                   25                   30

CTT CGT CAG AAA AAA TGG TCC CAC ATT CCT CCT GAA AAT ATC TTT        135
Leu Arg Gln Lys Lys Trp Ser His Ile Pro Pro Glu Asn Ile Phe
            35                   40                   45

CCT CTG GAG ACC AAT GAG ACC AAT CAT GTT AGC CTC AAG ATC GAT        180
Pro Leu Glu Thr Asn Glu Thr Asn His Val Ser Leu Lys Ile Asp
            50                   55                   60

GAT GAC AAA AGA CGA GAT ACA ATC CAG AGA CTA CGA CAG TGC AAA        225
Asp Asp Lys Arg Arg Asp Thr Ile Gln Arg Leu Arg Gln Cys Lys
            65                   70                   75

TAC GAC AAA AAG CGA GTG ATT CTC AAA GAT CTC AAG CAC AAT GAT        270
Tyr Asp Lys Lys Arg Val Ile Leu Lys Asp Leu Lys His Asn Asp
            80                   85                   90

GGT AAT TTC ACT GAA AAA CAG AAG ATA GAA TTG AAC AAG TTG CTT        315
Gly Asn Phe Thr Glu Lys Gln Lys Ile Glu Leu Asn Lys Leu Leu
            95                  100                  105

CAG AAA GAC TAT TAC AAC CTG ACC AAG TTC TAC GGC ACA GTG AAA        360
Gln Lys Asp Tyr Tyr Asn Leu Thr Lys Phe Tyr Gly Thr Val Lys
           110                  115                  120

CTT GAT ACC ATG ATC TTC GGG GTG ATA GAA TAC TGT GAG AGA GGA        405
Leu Asp Thr Met Ile Phe Gly Val Ile Glu Tyr Cys Glu Arg Gly
           125                  130                  135

TCC CCT CCG GGA AGT TTT AAA                                        426
Ser Pro Pro Gly Ser Phe Lys
           140

(2) INFORMATION FOR SEQ ID NO:53:
```

(i) SEQUENCE CHARACTERISTICS:
    (A) LENGTH: 142 amino acids
    (B) TYPE: amino acid
    (D) TOPOLOGY: linear (ii) MOLECULE TYPE: protein (xi) SEQUENCE DESCRIPTION: SEQ ID NO:53:

```
Met Ile Ala Val Phe Thr Leu Thr Gly Ala Val Val Leu Leu Leu
 1               5                  10                  15

Leu Val Ala Leu Leu Met Leu Arg Lys Tyr Arg Lys Asp Tyr Glu
                20                  25                  30

Leu Arg Gln Lys Lys Trp Ser His Ile Pro Pro Glu Asn Ile Phe
                35                  40                  45

Pro Leu Glu Thr Asn Glu Thr Asn His Val Ser Leu Lys Ile Asp
                50                  55                  60

Asp Asp Lys Arg Arg Asp Thr Ile Gln Arg Leu Arg Gln Cys Lys
                65                  70                  75

Tyr Asp Lys Lys Arg Val Ile Leu Lys Asp Leu Lys His Asn Asp
                80                  85                  90

Gly Asn Phe Thr Glu Lys Gln Lys Ile Glu Leu Asn Lys Leu Leu
                95                 100                 105

Gln Lys Asp Tyr Tyr Asn Leu Thr Lys Phe Tyr Gly Thr Val Lys
               110                 115                 120

Leu Asp Thr Met Ile Phe Gly Val Ile Glu Tyr Cys Glu Arg Gly
               125                 130                 135

Ser Pro Pro Gly Ser Phe Lys
               140
```

(2) INFORMATION FOR SEQ ID NO:54:

(i) SEQUENCE CHARACTERISTICS:
        (A) LENGTH: 366 base pairs
        (B) TYPE: nucleic acid
        (C) STRANDEDNESS: double
        (D) TOPOLOGY: linear (xi) SEQUENCE DESCRIPTION: SEQ ID NO:54:

```
ATG CTC AGA AAA TAT AGA AAA GAT TAT GAA CTT CGT CAG AAA AAA      45
Met Leu Arg Lys Tyr Arg Lys Asp Tyr Glu Leu Arg Gln Lys Lys
 1               5                  10                  15

TGG TCC CAC ATT CCT CCT GAA AAT ATC TTT CCT CTG GAG ACC AAT      90
Trp Ser His Ile Pro Pro Glu Asn Ile Phe Pro Leu Glu Thr Asn
                20                  25                  30

GAG ACC AAT CAT GTT AGC CTC AAG ATC GAT GAT GAC AAA AGA CGA     135
Glu Thr Asn His Val Ser Leu Lys Ile Asp Asp Asp Lys Arg Arg
                35                  40                  45

GAT ACA ATC CAG AGA CTA CGA CAG TGC AAA TAC GAC AAA AAG CGA     180
Asp Thr Ile Gln Arg Leu Arg Gln Cys Lys Tyr Asp Lys Lys Arg
                50                  55                  60

GTG ATT CTC AAA GAT CTC AAG CAC AAT GAT GGT AAT TTC ACT GAA     225
Val Ile Leu Lys Asp Leu Lys His Asn Asp Gly Asn Phe Thr Glu
                65                  70                  75

AAA CAG AAG ATA GAA TTG AAC AAG TTG CTT CAG AAA GAC TAT TAC     270
Lys Gln Lys Ile Glu Leu Asn Lys Leu Leu Gln Lys Asp Tyr Tyr
                80                  85                  90

AAC CTG ACC AAG TTC TAC GGC ACA GTG AAA CTT GAT ACC ATG ATC     315
Asn Leu Thr Lys Phe Tyr Gly Thr Val Lys Leu Asp Thr Met Ile
                95                 100                 105
```

```
TTC GGG GTG ATA GAA TAC TGT GAG AGA GGA TCC CCT CCG GGA AGT         360
Phe Gly Val Ile Glu Tyr Cys Glu Arg Gly Ser Pro Pro Gly Ser
            110                 115                 120

TTT AAA                                                              366
Phe Lys (2) INFORMATION FOR SEQ ID NO:55:

(i) SEQUENCE CHARACTERISTICS:
        (A) LENGTH: 122 amino acids
        (B) TYPE: amino acid
        (D) TOPOLOGY: linear (ii) MOLECULE TYPE: protein (xi) SEQUENCE DESCRIPTION: SEQ ID NO:55:

Met Leu Arg Lys Tyr Arg Lys Asp Tyr Glu Leu Arg Gln Lys Lys
 1               5                  10                  15

Trp Ser His Ile Pro Pro Glu Asn Ile Phe Pro Leu Glu Thr Asn
                20                  25                  30

Glu Thr Asn His Val Ser Leu Lys Ile Asp Asp Lys Arg Arg
                35                  40                  45

Asp Thr Ile Gln Arg Leu Arg Gln Cys Lys Tyr Asp Lys Lys Arg
                50                  55                  60

Val Ile Leu Lys Asp Leu Lys His Asn Asp Gly Asn Phe Thr Glu
                65                  70                  75

Lys Gln Lys Ile Glu Leu Asn Lys Leu Leu Gln Lys Asp Tyr Tyr
                80                  85                  90

Asn Leu Thr Lys Phe Tyr Gly Thr Val Lys Leu Asp Thr Met Ile
                95                  100                 105

Phe Gly Val Ile Glu Tyr Cys Glu Arg Gly Ser Pro Pro Gly Ser
                110                 115                 120

Phe Lys (2) INFORMATION FOR SEQ ID NO:56:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (xi) SEQUENCE DESCRIPTION: SEQ ID NO:56:

ATG ATC TTC GGG GTG ATA GAA TAC TGT GAG AGA GGA TCC CCT CCG          45
Met Ile Phe Gly Val Ile Glu Tyr Cys Glu Arg Gly Ser Pro Pro
 1               5                  10                  15

GGA AGT TTT AAA                                                      57
Gly Ser Phe Lys (2) INFORMATION FOR SEQ ID NO:57:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO:57:

Met Ile Phe Gly Val Ile Glu Tyr Cys Glu Arg Gly Ser Pro Pro
 1               5                  10                  15

Gly Ser Phe Lys
```

(2) INFORMATION FOR SEQ ID NO:58:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (xi) SEQUENCE DESCRIPTION: SEQ ID NO:58:

```
ATG ATA TTA CAG GCC GGG GCC CTC AGA TCC                          30
Met Ile Leu Gln Ala Gly Ala Leu Arg Ser
 1               5                  10
```

(2) INFORMATION FOR SEQ ID NO:59:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:59:

```
Met Ile Leu Gln Ala Gly Ala Leu Arg Ser
 1               5                  10
```

(2) INFORMATION FOR SEQ ID NO:60:

(i) SEQUENCE CHARACTERISTICS:
        (A) LENGTH: 156 base pairs
        (B) TYPE: nucleic acid
        (C) STRANDEDNESS: double
        (D) TOPOLOGY: linear (xi) SEQUENCE DESCRIPTION: SEQ ID NO:60:

```
ATG AAC TTC GTC AGA AAA AAT GGT CCC ACA TTC CTC CTG AAA ATA      45
Met Asn Phe Val Arg Lys Asn Gly Pro Thr Phe Leu Leu Lys Ile
 1               5                  10                  15

TCT TTC CTC TGG AGA CCA ATG AGA CCA ATC ATG TTA GCC TCA AGA      90
Ser Phe Leu Trp Arg Pro Met Arg Pro Ile Met Leu Ala Ser Arg
                20                  25                  30

TCG ATG ATG ACA AAA GAC GAG ATA CAA TCC AGA GAC TAC GAC AGT      135
Ser Met Met Thr Lys Asp Glu Ile Gln Ser Arg Asp Tyr Asp Ser
                35                  40                  45

GCA AAT ACG ACA AAA AGC GAG                                      156
Ala Asn Thr Thr Lys Ser Glu
                50
```

(2) INFORMATION FOR SEQ ID NO:61:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO:61:

```
Met Asn Phe Val Arg Lys Asn Gly Pro Thr Phe Leu Leu Lys Ile
 1               5                  10                  15

Ser Phe Leu Trp Arg Pro Met Arg Pro Ile Met Leu Ala Ser Arg
                20                  25                  30

Ser Met Met Thr Lys Asp Glu Ile Gln Ser Arg Asp Tyr Asp Ser
                35                  40                  45
```

```
Ala Asn Thr Thr Lys Ser Glu
            50

(2) INFORMATION FOR SEQ ID NO:62:

(i) SEQUENCE CHARACTERISTICS:
        (A) LENGTH: 93 base pairs
        (B) TYPE: nucleic acid
        (C) STRANDEDNESS: double
        (D) TOPOLOGY: linear (xi) SEQUENCE DESCRIPTION: SEQ ID NO:62:

ATG AGA CCA ATC ATG TTA GCC TCA AGA TCG ATG ATG ACA AAA GAC        45
Met Arg Pro Ile Met Leu Ala Ser Arg Ser Met Met Thr Lys Asp
 1               5                  10                  15

GAG ATA CAA TCC AGA GAC TAC GAC AGT GCA AAT ACG ACA AAA AGC        90
Glu Ile Gln Ser Arg Asp Tyr Asp Ser Ala Asn Thr Thr Lys Ser
                20                  25                  30

GAG                                                                93
Glu (2) INFORMATION FOR SEQ ID NO:63:

(i) SEQUENCE CHARACTERISTICS:
        (A) LENGTH: 31 amino acids
        (B) TYPE: amino acid
        (D) TOPOLOGY: linear (ii) MOLECULE TYPE: protein (xi) SEQUENCE DESCRIPTION: SEQ ID NO:63:

Met Arg Pro Ile Met Leu Ala Ser Arg Ser Met Met Thr Lys Asp
 1               5                  10                  15

Glu Ile Gln Ser Arg Asp Tyr Asp Ser Ala Asn Thr Thr Lys Ser
                20                  25                  30

Glu (2) INFORMATION FOR SEQ ID NO:64:

(i) SEQUENCE CHARACTERISTICS:
        (A) LENGTH: 81 base pairs
        (B) TYPE: nucleic acid
        (C) STRANDEDNESS: double
        (D) TOPOLOGY: linear (xi) SEQUENCE DESCRIPTION: SEQ ID NO:64:

ATG TTA GCC TCA AGA TCG ATG ATG ACA AAA GAC GAG ATA CAA TCC        45
Met Leu Ala Ser Arg Ser Met Met Thr Lys Asp Glu Ile Gln Ser
 1               5                  10                  15

AGA GAC TAC GAC AGT GCA AAT ACG ACA AAA AGC GAG                    81
Arg Asp Tyr Asp Ser Ala Asn Thr Thr Lys Ser Glu
                20                  25

(2) INFORMATION FOR SEQ ID NO:65:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO:65:

Met Leu Ala Ser Arg Ser Met Met Thr Lys Asp Glu Ile Gln Ser
 1               5                  10                  15
```

```
Arg Asp Tyr Asp Ser Ala Asn Thr Thr Lys Ser Glu
            20                  25
```

(2) INFORMATION FOR SEQ ID NO:66:

(i) SEQUENCE CHARACTERISTICS:
        (A) LENGTH: 63 base pairs
        (B) TYPE: nucleic acid
        (C) STRANDEDNESS: double
        (D) TOPOLOGY: linear (xi) SEQUENCE DESCRIPTION: SEQ ID NO:66:

```
ATG ATG ACA AAA GAC GAG ATA CAA TCC AGA GAC TAC GAC AGT GCA         45
Met Met Thr Lys Asp Glu Ile Gln Ser Arg Asp Tyr Asp Ser Ala
 1           5                  10                  15

AAT ACG ACA AAA AGC GAG                                             63
Asn Thr Thr Lys Ser Glu
            20
```

(2) INFORMATION FOR SEQ ID NO:67:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:67:

```
Met Met Thr Lys Asp Glu Ile Gln Ser Arg Asp Tyr Asp Ser Ala
 1           5                  10                  15

Asn Thr Thr Lys Ser Glu
            20
```

(2) INFORMATION FOR SEQ ID NO:68:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (xi) SEQUENCE DESCRIPTION: SEQ ID NO:68:

```
ATG ACA AAA GAC GAG ATA CAA TCC AGA GAC TAC GAC AGT GCA AAT         45
Met Thr Lys Asp Glu Ile Gln Ser Arg Asp Tyr Asp Ser Ala Asn
 1           5                  10                  15

ACG ACA AAA AGC GAG                                                 60
Thr Thr Lys Ser Glu
            20
```

(2) INFORMATION FOR SEQ ID NO:69:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:69:

```
Met Thr Lys Asp Glu Ile Gln Ser Arg Asp Tyr Asp Ser Ala Asn
 1           5                  10                  15

Thr Thr Lys Ser Glu
            20
```

(2) INFORMATION FOR SEQ ID NO:70:

```
     (i) SEQUENCE CHARACTERISTICS:
         (A) LENGTH: 18 base pairs
         (B) TYPE: nucleic acid
         (C) STRANDEDNESS: double
         (D) TOPOLOGY: linear (xi) SEQUENCE DESCRIPTION: SEQ ID NO:70:

ATG GTC CCA CAT TCC TCC                                          18
Met Val Pro His Ser Ser
 1               5

(2) INFORMATION FOR SEQ ID NO:71:

(i) SEQUENCE CHARACTERISTICS:
         (A) LENGTH: 6 amino acids
         (B) TYPE: amino acid
         (D) TOPOLOGY: linear (ii) MOLECULE TYPE: protein (xi) SEQUENCE DESCRIPTION: SEQ ID NO:71:

Met Val Pro His Ser Ser
 1               5

(2) INFORMATION FOR SEQ ID NO:72:

(i) SEQUENCE CHARACTERISTICS:
         (A) LENGTH: 30 base pairs
         (B) TYPE: nucleic acid
         (C) STRANDEDNESS: double
         (D) TOPOLOGY: linear (xi) SEQUENCE DESCRIPTION: SEQ ID NO:72:

ATG ATG GTA ATT TCA CTG AAA AAC AGA AGA                          30
Met Met Val Ile Ser Leu Lys Asn Arg Arg
 1               5                  10

(2) INFORMATION FOR SEQ ID NO:73:

(i) SEQUENCE CHARACTERISTICS:
         (A) LENGTH: 10 amino acids
         (B) TYPE: amino acid
         (D) TOPOLOGY: linear (ii) MOLECULE TYPE: protein (xi) SEQUENCE DESCRIPTION: SEQ ID NO:73:

Met Met Val Ile Ser Leu Lys Asn Arg Arg
 1               5                  10

(2) INFORMATION FOR SEQ ID NO:74:

(i) SEQUENCE CHARACTERISTICS:
         (A) LENGTH: 27 base pairs
         (B) TYPE: nucleic acid
         (C) STRANDEDNESS: double
         (D) TOPOLOGY: linear (xi) SEQUENCE DESCRIPTION: SEQ ID NO:74:

ATG GTA ATT TCA CTG AAA AAC AGA AGA                              27
Met Val Ile Ser Leu Lys Asn Arg Arg
 1               5

(2) INFORMATION FOR SEQ ID NO:75:

(i) SEQUENCE CHARACTERISTICS:
         (A) LENGTH: 9 amino acids
         (B) TYPE: amino acid
```

(D) TOPOLOGY: linear (ii) MOLECULE TYPE: protein (xi) SEQUENCE DESCRIPTION: SEQ ID NO:75:

Met Val Ile Ser Leu Lys Asn Arg Arg
  1               5

(2) INFORMATION FOR SEQ ID NO:76:

(i) SEQUENCE CHARACTERISTICS:
            (A) LENGTH: 42 base pairs
            (B) TYPE: nucleic acid
            (C) STRANDEDNESS: double
            (D) TOPOLOGY: linear (xi) SEQUENCE DESCRIPTION: SEQ ID NO:76:

ATG GCG GCC GGG AGC ATG CGA CGT CGG CCC ATT CGC CCT ATA            42
Met Ala Ala Gly Ser Met Arg Arg Arg Pro Ile Arg Pro Ile
  1               5                  10

(2) INFORMATION FOR SEQ ID NO:77:

(i) SEQUENCE CHARACTERISTICS:
            (A) LENGTH: 14 amino acids
            (B) TYPE: amino acid
            (D) TOPOLOGY: linear (ii) MOLECULE TYPE: protein (xi) SEQUENCE DESCRIPTION: SEQ ID NO:77:

Met Ala Ala Gly Ser Met Arg Arg Arg Pro Ile Arg Pro Ile
  1               5                  10

(2) INFORMATION FOR SEQ ID NO:78:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (xi) SEQUENCE DESCRIPTION: SEQ ID NO:78:

ATG CGA CGT CGG CCC ATT CGC CCT ATA                                27
Met Arg Arg Arg Pro Ile Arg Pro Ile
  1               5

(2) INFORMATION FOR SEQ ID NO:79:

(i) SEQUENCE CHARACTERISTICS:
            (A) LENGTH: 9 amino acids
            (B) TYPE: amino acid
            (D) TOPOLOGY: linear (ii) MOLECULE TYPE: protein (xi) SEQUENCE DESCRIPTION: SEQ ID NO:79:

Met Arg Arg Arg Pro Ile Arg Pro Ile
  1               5

(2) INFORMATION FOR SEQ ID NO:80:

(i) SEQUENCE CHARACTERISTICS:
            (A) LENGTH: 15 base pairs
            (B) TYPE: nucleic acid
            (C) STRANDEDNESS: double
            (D) TOPOLOGY: linear (xi) SEQUENCE DESCRIPTION: SEQ ID NO:80:

```
ATG ACA CAA TTT CCT                                                    15
Met Thr Gln Phe Pro
 1               5

(2) INFORMATION FOR SEQ ID NO:81:

(i) SEQUENCE CHARACTERISTICS:
        (A) LENGTH: 5 amino acids
        (B) TYPE: amino acid
        (C) STRANDEDNESS: double
        (D) TOPOLOGY: linear (xi) SEQUENCE DESCRIPTION: SEQ ID NO:81:

Met Thr Gln Phe Pro
 1               5

(2) INFORMATION FOR SEQ ID NO:82:

(i) SEQUENCE CHARACTERISTICS:
        (A) LENGTH:3783
        (B) TYPE: nucleic acid
        (C) STRANDEDNESS: both
        (D) TOPOLOGY: unknown (xi) SEQUENCE DESCRIPTION: SEQ ID NO:82:

TGGAGTGGGC TGAGGGACTC CACTAGAGGC TGTCCATCTG GATTCCCTGC CTCCCTAGGA     60

GCCCAACAGA GCAAAGCAAG TGGGCACAAG GAGTATGGTT CTAACGTGAT TGGGGTCATG    120

AAGACGTTGC TGTTGGACTT GGCTTTGTGG TCACTGCTCT TCCAGCCCGG GTGGCTGTCC    180

TTTAGTTCCC AGGTGAGTCA GAACTGCCAC AATGGCAGCT ATGAAATCAG CGTCCTGATG    240

ATGGGCAACT CAGCCTTTGC AGAGCCCCTG AAAAACTTGG AAGATGCGGT GAATGAGGGG    300

CTGGAAATAG TGAGAGGACG TCTGCAAAAT GCTGGCCTAA ATGTGACTGT GAACGCTTCA    360

TGTATTCGGA TGGTCTGATT CATAACTCAG GCGACTGCCG GAGTAGCACC TGTGAAGGCC    420

TCGACCTACT CAGGAAAATT TCAAATGCAC AACGGATGGG CTGTGTCCTC ATAGGGCCCT    480

CATGTACATA CTCCACCTTC CAGATGTACC TTGACACAGA ATTGAGCTAC CCCATGATCT    540

CAGCTGGAAG TTTTGGATTG TCATGTGACT ATAAAGAAAC CTTAACCAGG CTGATGTCTC    600

CAGCTAGAAA GTTGATGTAC TTCTTGGTTA ACTTTTGGAA AACCAACGAT CTGCCCTTCA    660

AAACTTATTC CTGGAGCACT TCGTATGTTT ACAAGAATGG TACAGAAACT GAGGACTGTT    720

TCTGGTACCT TAATGCTCTG GAGGCTAGCG TTTCCTATTT CTCCCACGAA CTCGGCTTTA    780

AGGTGGTGTT AAGACAAGAT AAGGAGTTTC AGGATATCTT AATGGACCAC AACAGGAAAA    840

GCAATGTGAT TATTATGTGT GGTGGTCCAG AGTTCCTCTA CAAGCTGAAG GGTGACCGAG    900

CAGTGGCTGA AGACATTGTC ATTATTCTAG TGGATCTTTT CAATGACCAG TACTTGGAGG    960

ACAATGTCAC AGCCCCTGAC TATATGAAAA ATGTCCTTGT TCTGACGCTG TCTCCTGGGA   1020

ATTCCCTTCT AAATAGCTCT TTCTCCAGGA ATCTATCACC AACAAAACGA GACTTTCGTC   1080

TTGCCTATTT GAATGAATC CTCGTCTTTG GACATATGCT GAAGATATTT CTTGAAAATG    1140

GAGAAAATAT TACCACCCCC AAATTTGCTC ATGCCTTCAG GAATCTCACT TTTGAAGGGT   1200

ATGACGGTCC AGTGACCTTG GATGACTGGG GGGATGTTGA CAGTACCATG GTGCTTCTGT   1260

ATACCTCTGT GGACACCAAG AAATACAAGG TTCTTTTGAC CTATGATACC CACGTAAATA   1320

AGACCTATCC TGTGGATATG AGCCCCACAT TCACTTGGAA GAACTCTAAA CTTCCTAATG   1380

ATATTACAGG CCGGGGCCCT CAGATCCTGA TGATTGCAGT CTTCACCCTC ACTGGAGCTG   1440

TGGTGCTGCT CCTGCTCGTC GCTCTCCTGA TGCTCAGAAA ATATAGAAAA GATTATGAAC   1500
```

```
TTCGTCAGAA AAAATGGTCC CACATTCCTC CTGAAAATAT CTTTCCTCTG GAGACCAATG    1560

AGACCAATCA TGTTAGCCTC AAGATCGATG ATGACAAAAG ACGAGATACA ATCCAGAGAC    1620

TACGACAGTG CAAATACGTC AAAAAGCGAG TGATTCTCAA AGATCTCAAG CACAATGATG    1680

GTAATTTCAC TGAAAAACAG AAGATAGAAT TGAACAAGTT GCTTCAGATT GACTATTACA    1740

CCCTAACCAA GTTCTACGGG ACAGTGAAAC TGGATACCAT GATCTTCGGG GTGATAGAAT    1800

ACTGTGAGAG AGGATCCCTC CGGGAAGTTT TAAATGACAC AATTTCCTAC CCTGATGGCA    1860

CATTCATGGA TTGGGAGTTT AAGATCTCTG TCTTGTATGA CATTGCTAAG GGAATGTCAT    1920

ATCTGCACTC CAGTAAGACA GAAGTCCATG GTCGTCTGAA ATCTACCAAC TGCGTAGTGG    1980

ACAGTAGAAT GGTGGTGAAG ATCACTGATT TTGGCTGCAA TTCCATTTTG CCTCCAAAAA    2040

AGGACCTGTG GACAGCTCCA GAGCACCTCC GCCAAGCCAA CATCTCTCAG AAAGGAGATG    2100

TGTACAGCTA TGGGATCATC GCACAGGAGA TCATTCTGCG GAAAGAAACC TTCTACACTT    2160

TGAGCTGTCG GGACCGGAAT GAGAAGATTT TCAGAGTGGA AAATTCCAAT GGAATGAAAC    2220

CCTTCCGCCC AGATTTATTC TTGGAAACAG CAGAGGAAAA AGAGCTAGAA GTGTACCTAC    2280

TTGTAAAAAA CTGTTGGGAG GAAGATCCAG AAAAGAGACC AGATTTCAAA AAAATTGAGA    2340

CTACACTTGC CAAGATATTT GGACTTTTTC ATGACCAAAA AAATGAAAGC TATATGGATA    2400

CCTTGATCCG ACGTCTACAG CTATATTCTC GAAACCTGGA ACATCTGGTA GAGGAAAGGA    2460

CACAGCTGTA CAAGGCAGAG AGGGACAGGG CTGACAGACT TAACTTTATG TTGCTTCCAA    2520

GGCTAGTGGT AAAGTCTCTG AAGGAGAAAG GCTTTGTGGA GCCGGAACTA TATGAGGAAG    2580

TTACAATCTA CTTCAGTGAC ATTGTAGGTT TCACTACTAT CTGCAAATAC AGCACCCCCA    2640

TGGAAGTGGT GGACATGCTT AATGACATCT ATAAGAGTTT TGACCACATT GTTGATCATC    2700

ATGATGTCTA CAAGGTGGAA ACCATCGGTG ATGCGTACAT GGTGGCTAGT GGTTTGCCTA    2760

AGAGAAATGG CAATCGGCAT GCAATAGACA TTGCCAAGAT GGCCTTGGAA ATCCTCAGCT    2820

TCATGGGGAC CTTTGAGCTG GAGCATCTTC CTGGCCTCCC AATATGGATT CGCATTGGAG    2880

TTCACTCTGG TCCCTGTGCT GCTGGAGTTG TGGGAATCAA GATGCCTCGT TATTGTCTAT    2940

TTGGAGATAC GGTCAACACA GCCTCTAGGA TGGAATCCAC TGGCCTCCCT TTGAGAATTC    3000

ACGTGAGTGG CTCCACCATA GCCATCCTGA AGAGAACTGA GTGCCAGTTC CTTTATGAAG    3060

TGAGAGGAGA AACATACTTA AAGGGAAGAG GAAATGAGAC TACCTACTGG CTGACTGGGA    3120

TGAAGGACCA GAAATTCAAC CTGCCAACCC CTCCTACTGT GGAGAATCAA CAGCGTTTGC    3180

AAGCAGAATT TTCAGACATG ATTGCCAACT CTTTACAGAA AAGACAGGCA GCAGGGATAA    3240

GAAGCCAAAA ACCCAGACGG GTAGCCAGCT ATAAAAAAGG CACTCTGGAA TACTTGCAGC    3300

TGAATACCAC AGACAAGGAG AGCACCTATT TTTAAACCTA AATGAGGTAT AAGGACTCAC    3360

ACAAATTAAA ATACAGCTGC ACTGAGGCCA GGCACCCTCA GGTGTCCTGA AAGCTTACTT    3420

TCCTGAGACC TCATGAGGCA GAAATGTCTT AGGCTTGGCT GCCCTGTTTG GACCATGGAC    3480

TTTCTTTGCA TGAATCAGAT GTGTTCTCAG TGAAATAACT ACCTTCCACT CTGGAACCTT    3540

ATTCCAGCAG TTGTTCCAGG GAGCTTCTAC CTGGAAAAGA AAAGAATTTC ATTTATTTTT    3600

TGTTTGTTTA TTTTTATCGT TTTTGTTTAC TGGCTTTCCT TCTGTATTCA TAAGATTTTT    3660

TAAATTGTCA TAATTATATT TTAAATACCC ATCTTCATTA AAGTATATTT AACTCATAAT    3720

TTTTGCAGAA AATATGCTAT ATATTAGGCA AGAATAAAAG CTAAAGGTTT CCCAAAAAAA    3780

AAA                                                                 3783
```

(2) INFORMATION FOR SEQ ID NO:83:

(i) SEQUENCE CHARACTERISTICS:
        (A) LENGTH:3641
        (B) TYPE: nucleic acid
        (C) STRANDEDNESS: both
        (D) TOPOLOGY: unknown (xi) SEQUENCE DESCRIPTION: SEQ ID NO:83:

```
TGGAGTGGGC TGAGGGACTC CACTAGAGGC TGTCCATCTG GATTCCCTGC CTCCCTAGGA    60

GCCCAACAGA GCAAAGCAAG TGGGCACAAG GAGTATGGTT CTAACGTGAT TGGGGTCATG   120

AAGACGTTGC TGTTGGACTT GGCTTTGTGG TCACTGCTCT TCCAGCCCGG GTGGCTGTCC   180

TTTAGTTCCC AGGCCTAAAT GTGACTGTGA ACGCTTCATG TATTCGGATG GTCTGATTCA   240

TAACTCAGGC GACTGCCGGA GTAGCACCTG TGAAGGCCTC GACCTACTCA GGAAAATTTC   300

AAATGCACAA CGGATGGGCT GTGTCCTCAT AGGGCCCTCA TGTACATACT CCACCTTCCA   360

GATGTACCTT GACACAGAAT TGAGCTACCC CATGATCTCA GCTGGAAGTT TTGGATTGTC   420

ATGTGACTAT AAAGAAACCT TAACCAGGCT GATGTCTCCA GCTAGAAAGT TGATGTACTT   480

CTTGGTTAAC TTTTGGAAAA CCAACGATCT GCCCTTCAAA ACTTATTCCT GGAGCACTTC   540

GTATGTTTAC AAGAATGGTA CAGAAACTGA GGACTGTTTC TGGTACCTTA ATGCTCTGGA   600

GGCTAGCGTT TCCTATTTCT CCCACGAACT CGGCTTTAAG GTGGTGTTAA GACAAGATAA   660

GGAGTTTCAG GATATCTTAA TGGACCACAA CAGGAAAAGC AATGTGATTA TTATGTGTGG   720

TGGTCCAGAG TTCCTCTACA AGCTGAAGGG TGACCGAGCA GTGGCTGAAG ACATTGTCAT   780

TATTCTAGTG GATCTTTTCA ATGACCAGTA CTTGGAGGAC AATGTCACAG CCCCTGACTA   840

TATGAAAAAT GTCCTTGTTC TGACGCTGTC TCCTGGGAAT TCCCTTCTAA ATAGCTCTTT   900

CTCCAGGAAT CTATCACCAA CAAAACGAGA CTTTCGTCTT GCCTATTTGA ATGGAATCCT   960

CGTCTTTGGA CATATGCTGA AGATATTTCT TGAAAATGGA GAAAATATTA CCACCCCCAA  1020

ATTTGCTCAT GCCTTCAGGA ATCTCACTTT TGAAGGGTAT GACGGTCCAG TGACCTTGGA  1080

TGACTGGGGG GATGTTGACA GTACCATGGT GCTTCTGTAT ACCTCTGTGG ACACCAAGAA  1140

ATACAAGGTT CTTTTGACCT ATGATACCCA CGTAAATAAG ACCTATCCTG TGGATATGAG  1200

CCCCACATTC ACTTGGAAGA ACTCTAAACT TCCTAATGAT ATTACAGGCC GGGGCCCTCA  1260

GATCCTGATG ATTGCAGTCT TCACCCTCAC TGGAGCTGTG GTGCTGCTCC TGCTCGTCGC  1320

TCTCCTGATG CTCAGAAAAT ATAGAAAAGA TTATGAACTT CGTCAGAAAA AATGGTCCCA  1380

CATTCCTCCT GAAAATATCT TTCCTCTGGA GACCAATGAG ACCAATCATG TTAGCCTCAA  1440

GATCGATGAT GACAAAAGAC GAGATACAAT CCAGAGACTA CGACAGTGCA ATACGTCAA   1500

AAAGCGAGTG ATTCTCAAAG ATCTCAAGCA CAATGATGGT AATTTCACTG AAAAACAGAA  1560

GATAGAATTG AACAAGTTGC TTCAGATTGA CTATTACACC CTAACCAAGT TCTACGGGAC  1620

AGTGAAACTG GATACCATGA TCTTCGGGGT GATAGAATAC TGTGAGAGAG ATCCCTCCG   1680

GGAAGTTTTA AATGACACAA TTTCCTACCC TGATGGCACA TTCATGGATT GGGAGTTTAA  1740

GATCTCTGTC TTGTATGACA TTGCTAAGGG AATGTCATAT CTGCACTCCA GTAAGACAGA  1800

AGTCCATGGT CGTCTGAAAT CTACCAACTG CGTAGTGGAC AGTAGAATGG TGGTGAAGAT  1860

CACTGATTTT GGCTGCAATT CCATTTTGCC TCCAAAAAAG GACCTGTGGA CAGCTCCAGA  1920

GCACCTCCGC CAAGCCAACA TCTCTCAGAA AGGAGATGTG TACAGCTATG GGATCATCGC  1980

ACAGGAGATC ATTCTGCGGA AAGAAACCTT CTACACTTTG AGCTGTCGGG ACCGGAATGA  2040
```

-continued

```
GAAGATTTTC AGAGTGGAAA ATTCCAATGG AATGAAACCC TTCCGCCCAG ATTTATTCTT    2100

GGAAACAGCA GAGGAAAAAG AGCTAGAAGT GTACCTACTT GTAAAAAACT GTTGGGAGGA    2160

AGATCCAGAA AAGAGACCAG ATTTCAAAAA AATTGAGACT ACACTTGCCA AGATATTTGG    2220

ACTTTTTCAT GACCAAAAAA ATGAAAGCTA TATGGATACC TTGATCCGAC GTCTACAGCT    2280

ATATTCTCGA AACCTGGAAC ATCTGGTAGA GGAAAGGACA CAGCTGTACA AGGCAGAGAG    2340

GGACAGGGCT GACAGACTTA ACTTTATGTT GCTTCCAAGG CTAGTGGTAA AGTCTCTGAA    2400

GGAGAAAGGC TTTGTGGAGC CGGAACTATA TGAGGAAGTT ACAATCTACT TCAGTGACAT    2460

TGTAGGTTTC ACTACTATCT GCAAATACAG CACCCCCATG GAAGTGGTGG ACATGCTTAA    2520

TGACATCTAT AAGAGTTTTG ACCACATTGT TGATCATCAT GATGTCTACA AGGTGGAAAC    2580

CATCGGTGAT GCGTACATGG TGGCTAGTGG TTTGCCTAAG AGAAATGGCA ATCGGCATGC    2640

AATAGACATT GCCAAGATGG CCTTGGAAAT CCTCAGCTTC ATGGGGACCT TTGAGCTGGA    2700

GCATCTTCCT GGCCTCCCAA TATGGATTCG CATTGGAGTT CACTCTGGTC CCTGTGCTGC    2760

TGGAGTTGTG GGAATCAAGA TGCCTCGTTA TTGTCTATTT GGAGATACGG TCAACACAGC    2820

CTCTAGGATG GAATCCACTG GCCTCCCTTT GAGAATTCAC GTGAGTGGCT CCACCATAGC    2880

CATCCTGAAG AGAACTGAGT GCCAGTTCCT TTATGAAGTG AGAGGAGAAA CATACTTAAA    2940

GGGAAGAGGA AATGAGACTA CCTACTGGCT GACTGGGATG AAGGACCAGA AATTCAACCT    3000

GCCAACCCCT CCTACTGTGG AGAATCAACA GCGTTTGCAA GCAGAATTTT CAGACATGAT    3060

TGCCAACTCT TTACAGAAAA GACAGGCAGC AGGGATAAGA AGCCAAAAAC CCAGACGGGT    3120

AGCCAGCTAT AAAAAAGGCA CTCTGGAATA CTTGCAGCTG AATACCACAG ACAAGGAGAG    3180

CACCTATTTT TAAACCTAAA TGAGGTATAA GGACTCACAC AAATTAAAAT ACAGCTGCAC    3240

TGAGGCCAGG CACCCTCAGG TGTCCTGAAA GCTTACTTTC CTGAGACCTC ATGAGGCAGA    3300

AATGTCTTAG GCTTGGCTGC CCTGTTTGGA CCATGGACTT TCTTTGCATG AATCAGATGT    3360

GTTCTCAGTG AAATAACTAC CTTCCACTCT GGAACCTTAT TCCAGCAGTT GTTCCAGGGA    3420

GCTTCTACCT GGAAAAGAAA AGAATTTCAT TTATTTTTTG TTTGTTTATT TTTATCGTTT    3480

TTGTTTACTG GCTTTCCTTC TGTATTCATA AGATTTTTTA AATTGTCATA ATTATATTTT    3540

AAATACCCAT CTTCATTAAA GTATATTTAA CTCATAATTT TTGCAGAAAA TATGCTATAT    3600

ATTAGGCAAG AATAAAAGCT AAAGGTTTCC CAAAAAAAAA A    3641
```

(2) INFORMATION FOR SEQ ID NO:84:

(i) SEQUENCE CHARACTERISTICS:
        (A) LENGTH:3745
        (B) TYPE: nucleic acid
        (C) STRANDEDNESS: both
        (D) TOPOLOGY: unknown (xi) SEQUENCE DESCRIPTION: SEQ ID NO:84:

```
CGCAAAGCAA GTGGGCACAA GGAGTATGGT TCTAACGTGA TTGGGGTCAT GAAGACGTTG      60

CTGTTGGACT TGGCTTTGTG GTCACTGCTC TTCCAGCCCG GGTGGCTGTC CTTTAGTTCC     120

CAGGTGAGTC AGAACTGCCA CAATGGCAGC TATGAAATCA GCGTCCTGAT GATGGGCAAC     180

TCAGCCTTTG CAGAGCCCCT GAAAAACTTG GAAGATGCGG TGAATGAGGG GCTGGAAATA     240

GTGAGAGGAC GTCTGCAAAA TGCTGGCCTA AATGTGACTG TGAACGCTAC TTTCATGTAT     300

TCGGATGGTC TGATTCATAA CTCAGGCGAC TGCCGGAGTA GCACCTGTGA AGGCCTCGAC     360

CTACTCAGGA AAATTTCAAA TGCACAACGG ATGGGCTGTG TCCTCATAGG GCCCTCATGT     420
```

```
ACATACTCCA CCTTCCAGAT GTACCTTGAC ACAGAATTGA GCTACCCCAT GATCTCAGCT    480

GGAAGTTTTG GATTGTCATG TGACTATAAA GAAACCTTAA CCAGGCTGAT GTCTCCAGCT    540

AGAAAGTTGA TGTACTTCTT GGTTAACTTT TGGAAAACCA ACGATCTGCC CTTCAAAACT    600

TATTCCTGGA GCACTTCGTA TGTTTACAAG AATGGTACAG AAACTGAGGA CTGTTTCTGG    660

TACCTTAATG CTCTGGAGGC TAGCGTTTCC TATTTCTCCC ACGAACTCGG CTTTAAGGTG    720

GTGTTAAGAC AAGATAAGGA GTTTCAGGAT ATCTTAATGG ACCACAACAG GAAAAGCAAT    780

GTGATTATTA TGTGTGGTGG TCCAGAGTTC CTCTACAAGC TGAAGGGTGA CCGAGCAGTG    840

GCTGAAGACA TTGTCATTAT TCTAGTGGAT CTTTTCAATG ACCAGTACTT GGAGGACAAT    900

GTCACAGCCC CTGACTATAT GAAAAATGTC CTTGTTCTGA CGCTGTCTCC TGGGAATTCC    960

CTTCTAAATA GCTCTTTCTC CAGGAATCTA TCACCAACAA AACGAGACTT TGCTCTTGCC   1020

TATTTGAATG GAATCCTGCT CTTTGGACAT ATGCTGAAGA TATTTCTTGA AAATGGAGAA   1080

AATATTACCA CCCCCAAATT TGCTCATGCT TTCAGGAATC TCACTTTTGA AGGGTATGAC   1140

GGTCCAGTGA CCTTGGATGA CTGGGGGGAT GTTGACAGTA CCATGGTGCT TCTGTATACC   1200

TCTGTGGACA CCAAGAAATA CAAGGTTCTT TTGACCTATG ATACCCACGT AAATAAGACC   1260

TATCCTGTGG ATATGAGCCC CACATTCACT TGGAAGAACT CTAAACTTCC TAATGATATT   1320

ACAGGCCGGG GCCCTCAGAT CCTGATGATT GCAGTCTTCA CCCTCACTGG AGCTGTGGTG   1380

CTGCTCCTGC TCGTCGCTCT CCTGATGCTC AGAAAATATA GAAAAGATTA TGAACTTCGT   1440

CAGAAAAAAT GGTCCCACAT TCCTCCTGAA AATATCTTTC CTCTGGAGAC CAATGAGACC   1500

AATCATGTTA GCCTCAAGAT CGATGATGAC AAAAGACGAG ATACAATCCA GAGACTACGA   1560

CAGTGCAAAT ACGACAAAAA GCGAGTGATT CTCAAAGATC TCAAGCACAA TGATGGTAAT   1620

TTCACTGAAA AACAGAAGAT AGAATTGAAC AAGTTGCTTC AGATTGACTA TTACAACCTG   1680

ACCAAGTTCT ACGGCACAGT GAAACTTGAT ACCATGATCT TCGGGGTGAT AGAATACTGT   1740

GAGAGAGGAT CCCTCCGGGA AGTTTTAAAT GACACAATTT CCTACCCTGA TGGCACATTC   1800

ATGGATTGGG AGTTTAAGAT CTCTGTCTTG TATGACATTG CTAAGGGAAT GTCATATCTG   1860

CACTCCAGTA AGACAGAAGT CCATGGTCGT CTGAAATCTA CCAACTGCGT AGTGGACAGT   1920

AGAATGGTGG TGAAGATCAC TGATTTTGGC TGCAATTCCA TTTTACCTCC AAAAAAGGAC   1980

CTGTGGACAG CTCCAGAGCA CCTCCGCCAA GCCAACATCT CTCAGAAAGG AGATGTGTAC   2040

AGCTATGGGA TCATCGCACA GGAGATCATT CTGCGGAAAA AAACCTTCTA CACTTTGAGC   2100

TGTCGGGACC GGAATGAGAA GATTTTCAGA GTGGAAAATT CCAATGGAAT GAAACCCTTC   2160

CGCCCAGATT TATTCTTGGA AACAGCAGAG GAAAAAGAGC TAGAAGTGTA CCTACTTGTA   2220

AAAAACTGTT GGGAGGAAGA TCCAGAAAAG AGACCAGATT TCAAAAAAAT TGAGACTACA   2280

CTTGCCAAGA TATTTGGACT TTTTCATGAC CAAAAAAATG AAAGCTATAT GGATACCTTG   2340

ATCCGACGTC TACAGCTATA TTCTCGAAAC CTGGAACATC TGGTAGAGGA AAGGACACAG   2400

CTGTACAAGG CAGAGAGGGA CAGGGCTGAC AGACTTAACT TTATGTTGCT TCCAAGGCTA   2460

GTGGTAAAGT CTCTGAAGGA GAAAGGCTTT GTGGAGCCGG AACTATATGA GGAAGTTACA   2520

ATCTACTTCA GTGACATTGT AGGTTTCACT ACTATCTGCA AATACAGCAC CCCCATGGAA   2580

GTGGTGGACA TGCTTAATGA CATCTATAAG AGTTTTGACC ACATTGTTGA TCATCATGAT   2640

GTCTACAAGG TGGAAACCAT CGGTGATGCG TACATGGTGG CTAGTGGTTT GCCTAAGAGA   2700

AATGGCAATC GGCATGCAAT AGACATTGCC AAGATGGCCT TGGAAATCCT CAGCTTCATG   2760

GGGACCTTTG AGCTGGAGCA TCTTCCTGGC CTCCCAATAT GGATTCGCAT TGGAGTTCAC   2820
```

```
TCTGGTCCCT GTGCTGCTGG AGTTGTGGGA ATCAAGATGC CTCGTTATTG TCTATTTGGA      2880

GATACGGTCA ACACAGCCTC TAGGATGGAA TCCACTGGCC TCCCTTTGAG AATTCACGTG      2940

AGTGGCTCCA CCATAGCCAT CCTGAAGAGA ACTGAGTGCC AGTTCCTTTA TGAAGTGAGA      3000

GGAGAAACAT ACTTAAAGGG AAGAGGAAAT GAGACTACCT ACTGGCTGAC TGGGATGAAG      3060

GACCAGAAAT TCAACCTGCC AACCCCTCCT ACTGTGGAGA ATCAACAGCG TTTGCAAGCA      3120

GAATTTTCAG ACATGATTGC CAACTCTTTA CAGAAAAGAC AGGCAGCAGG GATAAGAAGC      3180

CAAAAACCCA GACGGGTAGC CAGCTATAAA AAAGGCACTC TGGAATACTT GCAGCTGAAT      3240

ACCACAGACA AGGAGAGCAC CTATTTTTAA ACCTAAATGA GGTATAAGGA CTCACACAAA      3300

TTAAAATACA GCTGCACTGA GGCAGCGACC TCAAGTGTCC TGAAAGCTTA CATTTTCCTG      3360

AGACCTCAAT GAAGCAGAAA TGTACTTAGG CTTGGCTGCC CTGTCTGGAA CATGGACTTT      3420

CTTGCATGAA TCAGATGTGT GTTCTCAGTG AAATAACTAC CTTCCACTCT GGAACCTTAT      3480

TCCAGCAGTT GTTCCAGGGA GCTTCTACCT GGAAAAGAAA AGAAATGAAT AGACTATCTA      3540

GAACTTGAGA AGATTTTATT CTTATTTCAT TTATTTTTTG TTTGTTTATT TTTATCGTTT      3600

TTGTTTACTG GCTTTCCTTC TGTATTCATA AGATTTTTTA AATTGTCATA ATTATATTTT      3660

AAATACCCAT CTTCATTAAA GTATATTTAA CTCATAATTT TTGCAGAAAA TATGCTATAT      3720

ATTAGGCAAG AATAAAAGCT AAAGG                                           3745

(2) INFORMATION FOR SEQ ID NO:85:

(i) SEQUENCE CHARACTERISTICS:
            (A) LENGTH:3603
            (B) TYPE: nucleic acid
            (C) STRANDEDNESS: both
            (D) TOPOLOGY: unknown (xi) SEQUENCE DESCRIPTION: SEQ ID NO:85:

CGCAAAGCAA GTGGGCACAA GGAGTATGGT TCTAACGTGA TTGGGGTCAT GAAGACGTTG        60

CTGTTGGACT TGGCTTTGTG GTCACTGCTC TTCCAGCCCG GGTGGCTGTC CTTTAGTTC        120

CAGGCCTAAA TGTGACTGTG AACGCTACTT TCATGTATTC GGATGGTCTG ATTCATAAC        180

CAGGCGACTG CCGGAGTAGC ACCTGTGAAG GCCTCGACCT ACTCAGGAAA ATTTCAAAT        240

CACAACGGAT GGGCTGTGTC CTCATAGGGC CCTCATGTAC ATACTCCACC TTCCAGATG        300

ACCTTGACAC AGAATTGAGC TACCCCATGA TCTCAGCTGG AAGTTTTGGA TTGTCATGT        360

ACTATAAAGA AACCTTAACC AGGCTGATGT CTCCAGCTAG AAAGTTGATG TACTTCTTG        420

TTAACTTTTG GAAAACCAAC GATCTGCCCT TCAAAACTTA TTCCTGGAGC ACTTCGTAT        480

TTTACAAGAA TGGTACAGAA ACTGAGGACT GTTTCTGGTA CCTTAATGCT CTGGAGGCT        540

GCGTTTCCTA TTTCTCCCAC GAACTCGGCT TTAAGGTGGT GTTAAGACAA GATAAGGAG        600

TTCAGGATAT CTTAATGGAC CACAACAGGA AAAGCAATGT GATTATTATG TGTGGTGGT        660

CAGAGTTCCT CTACAAGCTG AAGGGTGACC GAGCAGTGGC TGAAGACATT GTCATTATT        720

TAGTGGATCT TTTCAATGAC CAGTACTTGG AGGACAATGT CACAGCCCCT GACTATATG        780

AAAATGTCCT TGTTCTGACG CTGTCTCCTG GGAATTCCCT TCTAAATAGC TCTTTCTCC        840

GGAATCTATC ACCAACAAAA CGAGACTTTG CTCTTGCCTA TTTGAATGGA ATCCTGCTC        900

TTGGACATAT GCTGAAGATA TTTCTTGAAA ATGGAGAAAA TATTACCACC CCCAAATTT        960

CTCATGCTTT CAGGAATCTC ACTTTTGAAG GGTATGACGG TCCAGTGACC TTGGATGA        1020

GGGGGGATGT TGACAGTACC ATGGTGCTTC TGTATACCTC TGTGGACACC AAGAAATA      1080
```

```
AGGTTCTTTT GACCTATGAT ACCCACGTAA ATAAGACCTA TCCTGTGGAT ATGAGCCC    1140

CATTCACTTG GAAGAACTCT AAACTTCCTA ATGATATTAC AGGCCGGGGC CCTCAGAT    1200

TGATGATTGC AGTCTTCACC CTCACTGGAG CTGTGGTGCT GCTCCTGCTC GTCGCTCT    1260

TGATGCTCAG AAAATATAGA AAAGATTATG AACTTCGTCA GAAAAAATGG TCCCACAT    1320

CTCCTGAAAA TATCTTTCCT CTGGAGACCA ATGAGACCAA TCATGTTAGC CTCAAGAT    1380

ATGATGACAA AAGACGAGAT ACAATCCAGA GACTACGACA GTGCAAATAC GACAAAAA    1440

GAGTGATTCT CAAAGATCTC AAGCACAATG ATGGTAATTT CACTGAAAAA CAGAAGAT    1500

AATTGAACAA GTTGCTTCAG ATTGACTATT ACAACCTGAC CAAGTTCTAC GGCACAGT    1560

AACTTGATAC CATGATCTTC GGGGTGATAG AATACTGTGA GAGAGGATCC CTCCGGGA    1620

TTTTAAATGA CACAATTTCC TACCCTGATG GCACATTCAT GGATTGGGAG TTTAAGAT    1680

CTGTCTTGTA TGACATTGCT AAGGGAATGT CATATCTGCA CTCCAGTAAG ACAGAAGT    1740

ATGGTCGTCT GAAATCTACC AACTGCGTAG TGGACAGTAG AATGGTGGTG AAGATCAC    1800

ATTTTGGCTG CAATTCCATT TTACCTCCAA AAAAGGACCT GTGGACAGCT CCAGAGCA    1860

TCCGCCAAGC CAACATCTCT CAGAAAGGAG ATGTGTACAG CTATGGGATC ATCGCACA    1920

AGATCATTCT GCGGAAAGAA ACCTTCTACA CTTTGAGCTG TCGGGACCGG AATGAGAA    1980

TTTTCAGAGT GGAAAATTCC AATGGAATGA AACCCTTCCG CCCAGATTTA TTCTTGGA    2040

CAGCAGAGGA AAAAGAGCTA GAAGTGTACC TACTTGTAAA AAACTGTTGG GAGGAAGA    2100

CAGAAAAGAG ACCAGATTTC AAAAAAATTG AGACTACACT TGCCAAGATA TTTGGACT    2160

TTCATGACCA AAAAAATGAA AGCTATATGG ATACCTTGAT CCGACGTCTA CAGCTATA    2220

CTCGAAACCT GGAACATCTG GTAGAGGAAA GGACACAGCT GTACAAGGCA GAGAGGGA    2280

GGGCTGACAG ACTTAACTTT ATGTTGCTTC CAAGGCTAGT GGTAAAGTCT CTGAAGGA    2340

AAGGCTTTGT GGAGCCGGAA CTATATGAGG AAGTTACAAT CTACTTCAGT GACATTGT    2400

GTTTCACTAC TATCTGCAAA TACAGCACCC CCATGGAAGT GGTGGACATG CTTAATGA    2460

TCTATAAGAG TTTTGACCAC ATTGTTGATC ATCATGATGT CTACAAGGTG GAAACCAT    2520

GTGATGCGTA CATGGTGGCT AGTGGTTTGC CTAAGAGAAA TGGCAATCGG CATGCAAT    2580

ACATTGCCAA GATGGCCTTG GAAATCCTCA GCTTCATGGG GACCTTTGAG CTGGAGCA    2640

TTCCTGGCCT CCCAATATGG ATTCGCATTG GAGTTCACTC TGGTCCCTGT GCTGCTGG    2700

TTGTGGGAAT CAAGATGCCT CGTTATTGTC TATTTGGAGA TACGGTCAAC ACAGCCTC    2760

GGATGGAATC CACTGGCCTC CCTTTGAGAA TTCACGTGAG TGGCTCCACC ATAGCCAT    2820

TGAAGAGAAC TGAGTGCCAG TTCCTTTATG AAGTGAGAGG AGAAACATAC TTAAAGGG    2880

GAGGAAATGA GACTACCTAC TGGCTGACTG GGATGAAGGA CCAGAAATTC AACCTGCC    2940

CCCCTCCTAC TGTGGAGAAT CAACAGCGTT TGCAAGCAGA ATTTTCAGAC ATGATTGC    3000

ACTCTTTACA GAAAGACAG GCAGCAGGGA TAAGAAGCCA AAAACCCAGA CGGGTAGC    3060

GCTATAAAAA AGGCACTCTG GAATACTTGC AGCTGAATAC CACAGACAAG GAGAGCAC    3120

ATTTTTAAAC CTAAATGAGG TATAAGGACT CACACAAATT AAAATACAGC TGCACTGA    3180

CAGCGACCTC AAGTGTCCTG AAAGCTTACA TTTTCCTGAG ACCTCAATGA AGCAGAAA    3240

TACTTAGGCT TGGCTGCCCT GTCTGGAACA TGGACTTTCT TGCATGAATC AGATGTGT    3300

TCTCAGTGAA ATAACTACCT TCCACTCTGG AACCTTATTC CAGCAGTTGT TCCAGGGA    3360

TTCTACCTGG AAAAGAAAAG AAATGAATAG ACTATCTAGA ACTTGAGAAG ATTTTATT    3420
```

-continued

```
TATTTCATTT ATTTTTTGTT TGTTTATTTT TATCGTTTTT GTTTACTGGC TTTCCTTC      3480

TATTCATAAG ATTTTTTAAA TTGTCATAAT TATATTTTAA ATACCCATCT TCATTAAA      3540

ATATTTAACT CATAATTTTT GCAGAAAATA TGCTATATAT TAGGCAAGAA TAAAAGCT      3600

AGG                                                                  3603
```

COMPOSITIONS THAT SPECIFICALLY BIND TO COLORECTAL CANCER CELLS AND METHODS OF USING THE SAME

FIELD OF THE INVENTION

The present invention relates to in vitro diagnostic methods for detecting colorectal cancer cells, to kits and reagent for performing such methods. The present invention relates to compounds and methods for in vivo imaging and treatment of colorectal tumors. The present invention relates to methods and compositions for making and using targeted gene therapy, antisense and drug compositions. The present invention relates to prophylactic and therapeutic anti-colorectal cancer vaccines and compositions and methods of making and using the same.

BACKGROUND OF THE INVENTION

Colorectal cancer is the third most common neoplasm worldwide. The mortality rate of newly diagnosed large bowel cancer approaches 50% and there has been little improvement over the past 40 years. Most of this mortality reflects local, regional and distant metastases.

Surgery is the mainstay of treatment for colorectal cancer but recurrence is frequent. Colorectal cancer has proven resistant to chemotherapy, although limited success has been achieved using a combination of 5-fluorouracil and levamisole. Surgery has had the largest impact on survival and, in some patients with limited disease, achieves a cure. However, surgery removes bulk tumor, leaving behind microscopic residual disease which ultimately results in recrudescence.

Early detection of primary, metastatic, and recurrent disease can significantly impact the prognosis of individuals suffering from colorectal cancer. Large bowel cancer diagnosed at an early stage has a significantly better outcome than that diagnosed at more advanced stages. Similarly, diagnosis of metastatic or recurrent disease earlier potentially carries with it a better prognosis.

Although current radiotherapeutic agents, chemotherapeutic agents and biological toxins are potent cytotoxins, they do not discriminate between normal and malignant cells, producing adverse effects and dose-limiting toxicities. Over the past decade, a novel approach has been employed to more specifically target agents to tumor cells, involving the conjugation of an active agent to molecules which binds preferentially to antigens that exist predominantly on tumor cells. These conjugates can be administered systemically and specifically bind to the targeted tumor cells. Theoretically, targeting permits uptake by cells of cytotoxic agents at concentrations which do not produce serious toxicities in normal tissues. Also, selective binding to targeted tumor cells facilitates detection of occult tumor and is therefore useful in designing imaging agents. Molecular targeting predominantly has employed monoclonal antibodies generated to antigens selectively expressed on tumor cells.

Immunoscintigraphy using monoclonal antibodies directed at tumor-specific markers has been employed to diagnose colorectal cancer. Monoclonal antibodies against carcinoembryonic antigen (CEA) labelled with $^{99}$Technetium identified 94% of patients with recurrent tumors. Similarly, $^{111}$Indium-labelled anti-CEA monoclonal antibodies successfully diagnosed 85% of patients with recurrent colorectal carcinoma who were not diagnosed by conventional techniques. $^{125}$Iodine-labelled antibodies have been effective in localizing more than 80% of the pathologically-confirmed recurrences by intraoperative gamma probe scanning.

Monoclonal antibodies have also been employed to target specific therapeutic agents in colorectal cancer. Preclinical studies demonstrated that anti-CEA antibodies labelled with $^{90}$Yttrium inhibited human colon carcinoma xenografts in nude mice. Antibodies generated to colorectal cancer cells and coupled to mitomycin C or neocarzinostatin demonstrated an anti-tumor effect on human colon cancer xenografts in nude mice and 3 patients with colon cancer. Similar results in animals were obtained with monoclonal antibodies conjugated to ricin toxin A chain.

Due to the sensitivity, specificity, and adverse-effect profile of monoclonal antibodies, the results obtained using monoclonal antibody-based therapeutics have shown them to be less than ideal targeting tools. Although monoclonal antibodies have been generated to antigens selectively expressed on tumors, no truly cancer-specific antibody has been identified. Most antigens expressed on neoplastic cells appear to be quantitatively increased in these compared to normal cells but the antigens are nonetheless often present in normal cells. Thus, antibodies to such determinants can react with non-neoplastic tissues, resulting in significant toxicities. Also, antibodies are relatively large molecules and consequently, often evoke an immune response in patients. These immune responses can result in significant toxicities in patients upon re-exposure to the targeting agents and can prevent targeting by the monoclonal due to immune complex formation with degradation and excretion. Finally, binding of antibodies to tumor cells may be low and targeted agents may be delivered to cells in quantities insufficient to achieve detection or cytotoxicity.

There remains a need for reagents, kits and methods for screening, diagnosing and monitoring individuals with colorectal cancer, particulalry metastasized colorectal cancer. There is a need for reagents, kits and methods for identifying and confirming that a cancer of unknown origin is colorectal cancer and for analyzing colon tissue and colorectal cancer samples to identify and confirm colorectal cancer and to determine the level of migration of such cancer cells. There remains a need for compositions which can specifically target metastasized colorectal cancer cells. There is a need for imaging agents which can specifically bind to metastasized colorectal cancer cells. There is a need for improved methods of imaging metastasized colorectal cancer cells. There is a need for therapeutic agents which can specifically bind to metastasized colorectal cancer cells. There is a need for improved methods of treating individuals who are suspected of suffering from colorectal cancer cells, especially individuals who are suspected of suffering from metastasis of colorectal cancer cells. There is a need for vaccine composition to treat and prevent metastasized colorectal cancer. There is a need for therapeutic agents which can specifically deliver gene therapeutics, antisense compounds and other drugs to colorectal cells.

SUMMARY OF THE INVENTION

The invention relates to isolated nucleic acid molecules that comprise a CRCA-1 transcript.

The invention relates to isolated nucleic acid molecules that comprise nucleic acid sequences that encode a substantially pure CRCA-1 translation product or a functional fragment thereof. The invention relates to isolated nucleic acid molecules that comprise nucleic acid sequences that encode a substantially pure proteins that have amino acid sequences shown in SEQ ID NOS:2–81.

The invention relates to isolated nucleic acid molecules that comprise nucleic acid sequences shown in SEQ ID NO:1 or a functional fragment thereof.

The invention relates to pharmaceutical compositions that comprise nucleic acid molecule that comprise a CRCA-1 transcript.

The invention relates to pharmaceutical compositions that comprise nucleic acid molecule that comprise nucleic acid sequence shown in SEQ ID NO:1 or a functional fragment thereof in combination with a pharmaceutically acceptable carrier.

The invention relates to a recombinant expression vector comprising the nucleic acid molecule that has a nucleotide sequence that comprises SEQ ID NO:1 or a functional fragment thereof.

The invention relates to a host cell comprising a recombinant expression vector comprising the nucleic acid molecule that has a nucleotide sequence that comprises SEQ ID NO:1 or a functional fragment thereof.

The invention relates to an oligonucleotide molecule comprising a nucleotide sequence complimentary to a nucleotide sequence of SEQ ID NO:1 or a functional fragment thereof.

The invention relates to isolated antibodies that bind to an epitope on a CRCA-1 translation product.

The invention relates to a substantially pure CRCA-1 translation product or a functional fragment thereof.

The invention relates to a substantially pure proteins that have amino acid sequences shown in SEQ ID NO:2-81.

The invention relates to pharmaceutical compositions comprising a substantially pure CRCA-1 translation product or a functional fragment thereof.

The invention relates to pharmaceutical compositions comprising a substantially pure protein having amino acid sequences shown in SEQ ID NO:2-81 in combination with a pharmaceutically acceptable carrier.

The invention relates to isolated antibodies that bind to an epitope on a protien having the amino acid sequence of SEQ ID NO:2-81.

The present invention relates to in vitro methods of determining whether or not an individual has metastasized colorectal cancer cells. The present invention relates to in vitro methods of examining samples of non-colorectal tissue and body fluids from an individual to determine whether or not a colorectal cancer specific transcript or a translation product thereof, CRCA-1, which is specific to colorectal cells including colorectal tumor cells, is being expressed by cells outside of the colorectal tract. The presence of a CRCA-1 translation product or of the CRCA-1 transcript outside the intestinal tract is indicative of expression of CRCA-1 and is evidence that the individual is suffering from metastasized colorectal cancer.

The present invention relates to in vitro methods of determining whether or not tumor cells are colorectal in origin. The present invention relates to in vitro methods of diagnosing whether or not an individual suffering from cancer is suffering from colorectal cancer. The present invention relates to in vitro methods of examining samples of tumors from an individual to determine whether or not CRCA-1, which is specific to colorectal cells including colorectal tumor cells, is being expressed by the tumor cells. The presence of a CRCA-1 translation product or of the CRCA-1 transcript is indicative of expression of CRCA-1 is evidence that the individual is suffering from colorectal cancer.

The present invention relates to in vitro kits for practicing the methods of the invention and to reagents and compositions useful as components in such in vitro kits of the invention.

The present invention relates to conjugated compounds which comprises a CRCA-1 translation product binding moiety and a radiostable active moiety.

The present invention relates to a pharmaceutical composition comprising a pharmaceutically acceptable carrier or diluent, and a conjugated compound which comprises a a CRCA-1 translation product binding moiety and a radiostable active moiety.

The present invention relates to a method of treating an individual suspected of suffering from metastasized colorectal cancer comprising the steps of administering to said individual a pharmaceutical composition comprising a pharmaceutically acceptable carrier or diluent, and a therapeutically effective amount of a conjugated compound which comprises a CRCA-1 translation product binding moiety and a radiostable active moiety.

The present invention relates to a pharmaceutical composition comprising a pharmaceutically acceptable carrier or diluent, and a conjugated compound which comprises a a CRCA-1 translation product binding moiety and a radioactive active moiety.

The present invention relates to a pharmaceutical composition comprising a pharmaceutically acceptable carrier or diluent, and conjugated compound that comprises a CRCA-1 translation product binding moiety and a radioactive active moiety wherein the conjugated compound is present in an amount effective for therapeutic or diagnostic use in humans suffering from colorectal cancer.

The present invention relates to a method of radioimaging metastasized colorectal cancer cells comprising the steps of first administering to an individual suspected of having metastasized colorectal cancer cells, a pharmaceutical composition that comprises a pharmaceutically acceptable carrier or diluent, and conjugated compound that comprises a CRCA-1 translation product binding moiety and a radioactive active moiety wherein the conjugated compound is present in an amount effective for diagnostic use in humans suffering from colorectal cancer and then detecting the localization and accumulation of radioactivity in the individual's body.

The present invention relates to a method of treating an individual suspected of suffering from metastasized colorectal cancer comprising the steps of administering to said individual a pharmaceutical composition comprising a pharmaceutically acceptable carrier or diluent, and a therapeutically effective amount of a conjugated compound which comprises a CRCA-1 translation product binding moiety and a radioactive active moiety.

The present invention relates to conjugated compounds which comprises a CRCA-1 translation product binding moiety and a active moiety which comprises an antisense molecule.

The present invention relates to a pharmaceutical composition comprising a pharmaceutically acceptable carrier or diluent, and a conjugated compound which comprises a CRCA-1 translation product binding moiety and an active moiety which comprises an antisense molecule.

The present invention relates to a method of treating an individual suspected of suffering from colorectal cancer comprising the steps of administering to a such an individual, a pharmaceutical composition comprising a pharmaceutically acceptable carrier or diluent and a therapeutically effective amount of a conjugated compound which comprises a CRCA-1 translation product binding moiety and an active moiety which comprises an antisense molecule.

The present invention relates to a method of preventing colorectal cancer in an individual comprising the steps of administering to said individual a pharmaceutical composition comprising a pharmaceutically acceptable carrier or diluent and a prophylactically effective amount of a conjugated compound which comprises a CRCA-1 translation product binding moiety and an active moiety which comprises an antisense molecule.

The present invention relates to unconjugated compositions comprises a liposome that includes CRCA-1 translation product ligands on its surface and an active component encapsualted therein.

The present invention relates to a pharmaceutical composition comprising a pharmaceutically acceptable carrier or diluent, and an unconjugated compositions comprises a liposome that includes CRCA-1 translation product ligands on its surface and an active component encapsualted therein.

The present invention relates to a method of treating an individual suspected of suffering from a disease, condition or disorder of the colon or of prevcenting such a disease, disorder or condition in an indiidual who is at risk of developing the same, comprising the steps of administering to the colon a such an individual, a pharmaceutical composition comprising a pharmaceutically acceptable carrier or diluent, and an unconjugated compositions that comprises a liposome that includes CRCA-1 translation product ligands on its surface and an active component encapsualted therein.

The present invention relates to a method of delivering an active agent to colon cells of an individual, including metastasized colorectal cancer cells comprising the steps of administering to such an individual, a pharmaceutical composition comprising a pharmaceutically acceptable carrier or diluent, and an unconjugated compositions that comprises a liposome that includes CRCA-1 translation product ligands on its surface and an active component encapsualted therein.

The present invention relates to compositions that comprise CRCA-1 translation product ligands in combination with an active component.

The present invention relates to a pharmaceutical composition comprising a pharmaceutically acceptable carrier or diluent and a composition that comprise CRCA-1 translation product ligands in combination with an active component.

The present invention relates to a method of treating an individual suspected of suffering from a disease, condition or disorder of the colon or of prevcenting such a disease, disorder or condition in an individual who is at risk of developing the same, comprising the steps of administering to the colon a such an individual, a pharmaceutically acceptable carrier or diluent and a composition that comprise CRCA-1 translation product ligands in combination with an active component.

The present invention relates to a method of delivering an active agent to colon cells of an individual, including metastasized colorectal cancer cells comprising the steps of administering to such an individual, a pharmaceutical composition comprising a pharmaceutically acceptable carrier or diluent and a composition that comprise CRCA-1 translation product ligands in combination with an active component.

The present invention relates to an isolated protein comprising at least one epitope of a CRCA-1 translation product. In some embodiments, the isolated protein comprises a CRCA-1 translation product. In some embodiments, the isolated protein consists of a CRCA-1 translation product.

The present invention relates to vaccines which comprise such proteins and a pharmaceutically acceptable carrier or diluent.

The present invention relates to a haptenized protein comprising at least one epitope of a CRCA-1 translation product. In some embodiments, the haptenized protein comprises a CRCA-1 translation product. In some embodiments, the haptenized protein consists of a CRCA-1 translation product.

The present invention relates to vaccines which comprise such haptenized proteins and a pharmaceutically acceptable carrier or diluent.

The present invention relates to nucleic acid molecules that encode a protein comprising at least one epitope of a CRCA-1 translation product. In some embodiments, the nucleic acid molecule encodes a protein that protein comprises a CRCA-1 translation product. In some embodiments, the nucleic acid molecule encodes a protein that consists of a CRCA-1 translation product. In some embodiments, the nucleic acid molecule encodes the CRCA-1 transcript. In some embodiments, the nucleic acid molecule is a plasmid.

The present invention relates to vaccines which comprise such nucleic acid molecules and a pharmaceutically acceptable carrier or diluent.

The present invention relates to vectors that comprise nucleic acid molecules that encode a protein comprising at least one epitope of a CRCA-1 translation product. In some embodiments, the vector comprises a nucleic acid molecule that encodes a protein that protein comprises a CRCA-1 translation product. In some embodiments, the vector comprises a nucleic acid molecule that encodes a protein that consists of a CRCA-1 translation product. In some embodiments, the vector comprises a nucleic acid molecule that is the CRCA-1 transcript. In some embodiments, the vector is a virus or a bacterial cell. In some embodiments, the vector is a recombinant vaccinia virus.

The present invention relates to vaccines which comprise such vectors and a pharmaceutically acceptable carrier or diluent.

The present invention relates to killed or inactivated cells or particles that comprise a protein comprising at least one epitope of a CRCA-1 translation product. In some embodiments, the killed or inactivated cells or particles vector comprise the transmembrane domain of the human ST receptor protein. In some embodiments, the killed or inactivated cells or particles comprise a CRCA-1 translation product. In some embodiments, the killed or inactivated cells or particles consist of a CRCA-1 translation product. In some embodiments, the killed or inactivated cells or particles vector is a killed or inactivated colorectal tumor cells.

The present invention relates to vaccines which comprise such killed or inactivated cells or particles and a pharmaceutically acceptable carrier or diluent.

The present invention relates to haptenized killed or inactivated cells or particles that comprise a protein comprising at least one epitope of a CRCA-1 translation product. In some embodiments, the haptenized killed or inactivated cells or particles comprise a CRCA-1 translation product. In some embodiments, the haptenized killed or inactivated cells or particles consist of a CRCA-1 translation product. In some embodiments, the haptenized killed or inactivated cells or particles vector is a killed or inactivated colorectal tumor cells.

The present invention relates to vaccines which comprise such haptenized killed or inactivated cells or particles and a pharmaceutically acceptable carrier or diluent.

The present invention relates to methods of treating individuals suffering from metastasized colorectal cancer. The method of the present invention provides administering to such an individual a therapeutically effective amount of a vaccine of the invention. The invention relates to the use of such vaccines as immunotherapeutics.

The present invention relates to methods of treating individuals susceptible metastasized colorectal cancer. The method of the present invention provides administering to such an individual an amount of a vaccine of the invention effective to prevent or combat metastasized colorectal cancer. The present invention relates to the use of the vaccines of the invention prophylactically.

BRIEF DESCRIPTION OF THE FIGURE

FIG. 1 shows the nucleotide sequence of the human ST receptor mRNA, GeneBank Accession #S57551, which is incorporarted herein by reference. The gray shaded area is the sequence deleted in CRCA-1 transcript including one of the two boxed "GG" sequences or one G from each box. The start codon, ATG, which is nucleotides 118-119-120 of the sequence is the intiation codon for ST receptor protein expression. The CRCA-1 transcript SEQ ID NO:83 or SEQ ID NO:85 is missing a 142 nucleotide sequence spanning nucleotides 192-333, 193-334 or 194-335. Thus unique sequences of the CRCA-1 transcript not found ST receptor mRNA include nucleotides 191-192-193-336, 191-192-335-336 or 191-334-335-336 as set forth in FIG. 1 or using corresponding numbers from sequences set forth in the sequence listing. These 4 nucleotide sequences are all identical, A-G-G-C, and correspond to nucleotides 110-111-112-113 of SEQ ID NO:1.

DETAILED DESCRIPTION OF THE INVENTION

Definitions

As used herein, the terms "ST" and "native ST" are used interchangeably and are meant to refer to heat-stable toxin (ST) which is a peptide produced by E. coli, as well as other organisms. STs are naturally occurring peptides which 1) are naturally produced by organisms, 2) bind to the ST receptor and 3) activate the signal cascade that mediates ST-induced diarrhea.

As used herein, the terms "ST receptor", "guanylyl cyclase C receptor" and "GCC receptor" are meant to refer to the receptors found on colorectal cells, including local and metastasized colorectal cancer cells, which bind to ST. In normal individuals, ST receptors are found exclusively in cells of intestine, in particular in cells in the duodenum, small intestine (jejunum and ileum), the large intestine, colon (cecum, ascending colon, transverse colon, descending colon and sigmoid colon) and rectum.

As used herein, the terms "colorectal cancer-associated transcript" and "CRCA-1 transcript" are meant to refer to an alternative form of the mRNA for the ST receptor produced by transcription of the human ST receptor gene. The CRCA-1 transcript possesses an alternative sequence from that of the ST receptor encoding-mRNA. CRCA-1 transcript preferably has a nucleotide sequence set forth in SEQ ID NO:1. CRCA-1 transcript is found in colorectal cells, including local and metastasized colorectal cancer cells. In normal individuals, CRCA-1 transcript have been found exclusively in cells of intestine, in particular in cells in the duodenum, small intestine (jejunum and ileum), the large intestine, colon (cecum, ascending colon, transverse colon, descending colon and sigmoid colon) and rectum.

As used herein, the term "functional fragment" as used in the term "functional fragment of a CRCA-1 transcript product" is meant to fragments of CRCA-1 transcript which are functional with respect to nucleic acid molecules with full length sequences. For example, a functional fragment may be useful as an oligonucleotide or nucleic acid probe, a primer, an antisense oligonucleotide or nucleic acid molecule or a coding sequence. Functional fragments of the CRCA-1 transcript are unique compared to other known nucleic acid molecules, in particular functional fragments of the CRCA-1 transcript are unique compared to nucleic acid sequence of the ST receptor MRNA. The nucleotide sequence encoding human ST receptor protein is disclosed in FIG. 1 (SEQ ID NO:82), SEQ ID NO:84, and F. J. Sauvage et al. 1991 *J. Biol. Chem.* 266:17912–17918 which are incorporated herein by reference. The deleted sequence which results in the generation for the CRCA-1 transcript is disclosed in FIG. 1 (SEQ ID NO:83) and SEQ ID NO:85. Thus, the functional fragments of the CRCA-1 include specific sequences not found on the ST recpetor mRNA. Such unique sequences include the sequences on either side of the deletion thus forming a unique sequence relative to the ST receptor MRNA sequence. Accordingly, a functional fragment will include nucleotides 110–113 of SEQ ID NO:1. It is preferred that the unique sequence additionally include 5–10 or more sequences 5' to nucleotide 110 and 5–10 or more sequences 3' to nucleotide 113. oligonucleotides and other fragments of the CRCA-1 transcript which have sequences of function fragments include nucleitides 110–113 of SEQ ID NO:1 and ma additionally include sequences 5' and 3' to the unique four nucleotide sequences formed by the deletion. For example, a PCR primer having 8-28 nucleotides including a unique sequence for CRCA-1, i.e. a functional fragment having 8 nucleotides may include nucleotide sequence 106-113 or 110-117 or an 8 nucleotide seuquence generated from the intermediate sequences, i.e. 107-114, 108-115 or 109-116, or a functional fragment having 28 nucleotides may include nucleotide sequence 86-113 or 110-137 or a 28 nucleotide sequence generated from the intermediate sequences. Similarly, other functional fragments of CRCA-1 transcript would include 110-113 of SEQ ID NO:1 as part of a fragment of SEQ ID NO:1. With respect to CRCA-1 specific primers, sets of such primers may include one unique fragment of CRCA-1 transcript and one primer which is not specific for a unique CRCA-1 sequence provided that such a pair of primers can be used to amplify a CRCA-1 specific sequence.

As used herein, the terms "colorectal cancer-associated translation products" and "CRCA-1 translation products" are meant to refer to translation products set forth in SEQ ID NOS:2–81. CRCA-1 translation products are found in colorectal cells, including local and metastasized colorectal cancer cells. In normal individuals, CRCA-1 translation products have been found exclusively in cells of intestine, in particular in cells in the duodenum, small intestine (jejunum and ileum), the large intestine, colon (cecum, ascending colon, transverse colon, descending colon and sigmoid colon) and rectum.

As used herein, the term "functional fragment" as used in the term "functional fragment of a CRCA-1 translation product" is meant to fragments of CRCA-1 translation products which function in the same manner as proteinaceous compounds with full length sequences. For example, an immunogenically functional fragment of a CRCA-1 comprises an epitope recognized by an anti-CRCA-1 translation product antibody. A ligand-binding functional fragment of a CRCA-1 comprises a sequence which forms a structure that can bind to a ligand which recognizes and binds to a CRCA-1 translation product.

As used herein, the term "epitope recognized by an anti-CRCA-1 translation product antibody" refers those epitopes recognized by an anti-CRCA-1 translation product antibody which does not recognize epitopes of non-CRCA-1 translation products, i.e. does not cross react with non-CRCA-1 proteins.

As used herein, the term "antibody" is meant to refer to complete, intact antibodies, and Fab fragments and F(ab) 2 fragments thereof. Complete, intact antibodies include monoclonal antibodies such as murine monoclonal antibodies, chimeric antibodies and humanized antibodies.

As used herein, the term "CRCA-1 translation product ligand" is meant to refer to compounds which specifically bind to a CRCA-1 translation product. Antibodies that bind to a CRCA-1 translation product are CRCA-1 translation product ligands. An CRCA-1 translation product ligand may be a protein, peptide or a non-peptide.

As used herein, the term "active agent" is meant to refer to compounds that are therapeutic agents or imaging agents.

As used herein, the term "radiostable" is meant to refer to compounds which do not undergo radioactive decay; i.e. compounds which are not radioactive.

As used herein, the term "therapeutic agent" is meant to refer to chemotherapeutics, toxins, radiotherapeutics, targeting agents or radiosensitizing agents.

As used herein, the term "chemotherapeutic" is meant to refer to compounds that, when contacted with and/or incorporated into a cell, produce an effect on the cell including causing the death of the cell, inhibiting cell division or inducing differentiation.

As used herein, the term "toxin" is meant to refer to compounds that, when contacted with and/or incorporated into a cell, produce the death of the cell.

As used herein, the term "radiotherapeutic" is meant to refer to radionuclides which when contacted with and/or incorporated into a cell, produce the death of the cell.

As used herein, the term "targeting agent" is meant to refer compounds which can be bound by and or react with other compounds. Targeting agents may be used to deliver chemotherapeutics, toxins, enzymes, radiotherapeutics, antibodies or imaging agents to cells that have targeting agents associated with them and/or to convert or otherwise transform or enhance co-administered active agents. A targeting agent may include a moiety that constitutes a first agent that is localized to the cell which when contacted with a second agent either is converted to a third agent which has a desired activity or causes the conversion of the second agent into an agent with a desired activity. The result is the localized agent facilitates exposure of an agent with a desired activity to the metastasized cell.

As used herein, the term "radiosensitizing agent" is meant to refer to agents which increase the susceptibility of cells to the damaging effects of ionizing radiation. A radiosensitizing agent permits lower doses of radiation to be administered and still provide a therapeutically effective dose.

As used herein, the term "imaging agent" is meant to refer to compounds which can be detected.

As used herein, the term "CRCA-1 translation product binding moiety" is meant to refer to the portion of a conjugated compound that constitutes an CRCA-1 translation product ligand.

As used herein, the term "active moiety" is meant to refer to the portion of a conjugated compound that constitutes an active agent.

As used herein, the terms "conjugated compound" and "conjugated composition" are used interchangeably and meant to refer to a compound which comprises an CRCA-1 translation product binding moiety and an active moiety and which is capable of binding to the CRCA-1 translation product. Conjugated compounds according to the present invention comprise a portion which constitutes an CRCA-1 translation product ligand and a portion which constitutes an active agent. Thus, conjugated compounds according to the present invention are capable of specifically binding to the CRCA-1 translation product and include a portion which is a therapeutic agent or imaging agent. Conjugated compositions may comprise crosslinkers and/or molecules that serve as spacers between the moieties.

As used herein, the terms "crosslinker", "crosslinking agent", "conjugating agent", "coupling agent", "condensation reagent" and "bifunctional crosslinker" are used interchangeably and are meant to refer to molecular groups which are used to attach the CRCA-1 translation product ligand and the active agent to thus form the conjugated compound.

As used herein, the term "colorectal cancer" is meant to include the well-accepted medical definition that defines colorectal cancer as a medical condition characterized by cancer of cells of the intestinal tract below the small intestine (i.e. the large intestine (colon), including the cecum, ascending colon, transverse colon, descending colon, and sigmoid colon, and rectum). Additionally, as used herein, the term "colorectal cancer" is meant to further include medical conditions which are characterized by cancer of cells of the duodenum and small intestine (jejunum and ileum). The definition of colorectal cancer used herein is more expansive than the common medical definition but is provided as such since the cells of the duodenum and small intestine also contain CRCA-1 translation products and are therefore amenable to the methods of the present invention using the compounds of the present invention.

As used herein, the term "metastasis" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body. The present invention relates to methods of delivering active agents to metastasized colorectal cancer cells.

As used herein, the term "metastasized colorectal cancer cells" is meant to refer to colorectal cancer cells which have metastasized; colorectal cancer cells localized in a part of the body other than the duodenum, small intestine (jejunum and ileum), large intestine (colon), including the cecum, ascending colon, transverse colon, descending colon, and sigmoid colon, and rectum.

As used herein, the term "non-colorectal samples and extra-intestinal sample" are used interchangeably and meant to refer to a sample of tissue or body fluid from a source other than colorectal tissue. In some preferred embodiments, the non-colorectal sample is a sample of tissue such as lymph nodes. In some preferred embodiments, the non-colorectal sample is a sample of extra-intestinal tissue which is an adenocarcinoma of unconfirmed origin. In some preferred embodiments, the non-colorectal sample is a blood sample.

As used herein, "an individual suffering from an adenocarcinoma of unconfirmed origin" is meant to refer to an individual who has a tumor in which the origin has not been definitively identified.

As used herein, "an individual is suspected of being susceptible to metastasized colorectal cancer" is meant to refer to an individual who is at a particular risk of developing metastasized colorectal cancer. Examples of individuals at a particular risk of developing metastasized colorectal cancer are those whose family medical history indicates above average incidence of colorectal cancer among family members and/or those who have already developed colorectal cancer and have been effectively treated who therefore face a risk of relapse and recurrence.

As used herein, the term "antisense composition" and "antisense molecules" are used interchangeably and are meant to refer to compounds that regulate transcription or translation by hybridizing to DNA or RNA and inhibiting and/or preventing transcription or translation from taking place. Antisense molecules include nucleic acid molecules and derivatives and analogs thereof. Antisense molecules hybridize to DNA or RNA in the same manner as complementary nucleotide sequences do regardless of whether or not the antisense molecule is a nucleic acid molecule or a derivative or analog. Antisense molecules inhibit or prevent transcription or translation of genes whose expression is linked to colorectal cancer.

As used herein, the term "CRCA-1 immunogen" is meant to refer to one or more CRCA-1 translation products or a fragment thereof or a protein that comprises the same or a haptenized product thereof, cells and particles which display at least one CRCA-1 epitope, and haptenized cells and haptenized particles which display at least one CRCA-1 epitope.

As used herein, the term "recombinant expression vector" is meant to refer to a plasmid, phage, viral particle or other vector which, when introduced into an appropriate host, contains the necessary genetic elements to direct expression of the coding sequence that encodes the protein. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences.

ST Receptors and CRCA-1

Carcinomas derived from intestinal mucosa continue to express ST receptors on their cell surfaces. The expression of ST receptors by metastatic tumors enables this protein and its mRNA to be a specific biomarker for the presence of metastatic colorectal cancer cells in extra-intestinal tissues and blood. Indeed, this characteristic permits the detection of ST receptor mRNA by RT-PCR analysis to be a diagnostic test to stage patients with colorectal cancer and follow patients after surgery for evidence of recurrent disease in their blood. Further, the ST receptor may be targeted with a ligand conjugated to an active agent in order to deliver the active agent to metastasized colotrectal tumor cells in vivo.

U.S. Pat. No. 5,518,888 issued May 21, 1996 to Waldman, PCT application PCT/US94/12232 filed Oct. 26, 1994, U.S. application Ser. No. 08/467,920 filed Jun. 6, 1995, and U.S. application Ser. No. 08/583,447 filed Jan. 5, 1996, which are each incorporated herein by reference, disclose that metastized colorectal tumors can be targetted for delivery of active compounds by targetting ST receptors. The presence of ST receptors on cells outside of the intestinal tract as a marker for colorectal cancer allows for the screening, identification and treatment of individuals with metastasized colorectal tumors. ST receptors may also be used to target delivery of gene therapeutics and antisense compounds to colorectal cells.

U.S. Pat. No. 5,601,990 issued Feb. 11, 1997 to Waldman, PCT application PCT/US94/12232 filed Oct. 26, 1994, and PCT application PCT/US97/07467 fileed May 2, 1997, which are each incorporated herein by reference, disclose that detection of evidence of expression of ST receptors in samples of tissue and body fluid from outside the intestinal tract indicate metastized colorectal cancer.

PCT application PCT/US97/07565 filed May 2, 1997, which is incorporated herein by reference, disclose that immunogens with epitopes that can be targetted by antibodies that react with ST receptors can be used in vaccines compositions useful as prophylactic and therapeutic antimetastatic colorectal cancer compositions.

Recently, studies have identified an alternative form of the mRNA for the ST receptor, isolated from human colon carcinoma cells. This mRNA has a substantial deletion of nucleic acids in the first exon in the coding region of the ST receptor. This deletion results in a frameshift of the coding region such that it no longer encodes the amino acid sequence of the ST receptor. However, this alternative splice variant mRNA appears to exhibit a selective pattern of expression that parallels that of the ST receptor. This newly-identified mRNA has been detected only in normal intestinal mucosal cells, human colorectal tumors, but not in extra-intestinal tissues. Furthermore, the expression of this newly-identified mRNA can be detected by RT-PCR analysis separately from ST receptor mRNA. Thus, the present invention provides the use of this colorectal cancer-associated transcript (CRCA-1) as a specific molecular diagnostic marker for the diagnosis, staging, and post-operative surveillance of patients with colorectal cancer.

The newly-identified CRCA-1 appears to be a highly specific marker for the diagnosis, staging, and post-operative surveillance of patients with colorectal cancer. Detection of the expression of CRCA-1 employing molecular techniques, including, but not limited to, RT-PCR, can be employed to diagnose and stage patients, follow the development of recurrence after surgery, and, potentially, screen normal people for the development of colorectal cancer. Detection of the expression of CRCA-1 employing molecular techniques, including, but not limited to, RT-PCR, can be employed to diagnose and stage patients, follow the development of recurrence after surgery, and, potentially, screen normal people for the development of colorectal cancer.

The nucleotide sequence of the CRCA-1 transcription product is set forth as SEQ ID NQ:1. Cells of colorectal origin may be distinguised from cells of other origin based by detecting the presence or absence of the CRCA-1 transcription product.

It has further been discovered that one or more translation products may be produced from translation of the CRCA-1 transcription product. The transcription product contains a number of initiation codons from which translation can begin, generating a number of translation products. Amino acid sequences of CRCA-1 translation products are set forth as SEQ ID NOS:2–81. Cells of colorectal origin may be distinguised from cells of other origin by detecting the presence or absence of one or more of the CRCA-1 translation products.

ST receptors are unique in that they are only localized in the apical brush border membranes of the cells lining the intestinal tract. Indeed, they are not found in any other cell type in placental mammals. In addition, ST receptors are almost exclusively localized to the apical membranes, with little being found in the basolateral membranes on the sides of intestinal cells. Like ST receptors, the expression of CRCA-1 is similarly localized.

Mucosal cells lining the intestine are joined together by tight junctions which form a barrier against the passage of intestinal contents into the blood stream and components of the blood stream into the intestinal lumen. Therefore, the apical location of cells expressing ST receptors and CRCA-1 isolates results in the isolation of such cells from the circulatory system so that they may be considered to exist separate from the rest of the body; essentially the "outside" of the body. Therefore, the rest of the body is considered "outside" the intestinal tract. Compositions administered "outside" the intestinal tract are maintained apart and segregated from the only cells which normally express ST receptors. Conversely, tissue samples taken from tissue outside of the intestinal tract do not normally contain cells which express ST receptors and CRCA-1.

In individuals suffering from colorectal cancer, the cancer cells are often derived from cells that produce and display the ST receptor and these cancer cells continue to produce and display the ST receptor on their cell surfaces. It has been observed that CRCA-1 is expressed by colorectal cancer cells.

When such cancer cells metastasize, the metastasized cancer cells continue to produce and display the ST receptor. The expression of CRCA-1 by metastatic tumor cells provides a detectable target for in vitro screening, diagnosis, monitoring and staging as well as a target for in vivo delivery of conjugated compositions that comprise active agents for the imaging and treatment.

The present invention relates to isolated CRCA-1 translation products. The present invention relates to isolated CRCA-1 transcript. The present invention relates to isolated antibodies specific for such products and to hybridomas which produce such antibodies. Isolated translation products or functional fragments thereof are useful to genrate antibodes according to the invention. Some aspects of the invention nucleic acid molecules that encode the translation products. Nucleic acid molecules are useful to produce proteins which are be used to generate antibodies.

In vitro Diagnostics

According to some embodiments of the invention, compositions, kits and in vitro methods are provided for screening, diagnosiing and analyzing patients and patient samples to detect evidence of CRCA-1 expression by cells outside of the intestinal tract wherein the expression of CRCA-1 is indicative of metastasis of colorectal cancer. Furthermore, the present invention relates to methods, compositions and kits useful in the in vitro screening, diagnosis and analysis of patient and patient samples to detect evidence of CRCA-1 expression by tumor cells outside of the intestinal tract wherein the presence of cells that express CRCA-1 indicates and/or confirms that a tumor is of colorectal cancer origin. In an additional aspect of the invention, compositions, kits and methods are provided which are useful to visualize colorectal cells. Such compositions, kits and methods of analyzing tissue samples from the colon tissue to evaluate the extent of metastasis or invasion of colorectal tumor cells into the lamina propria.

In vitro screening and diagnostic compositions, methods and kits can be used in the monitoring of individuals who are in high risk groups for colorectal cancer such as those who have been diagnosed with localized disease and/or metastasized disease and/or those who are genetically linked to the disease. In vitro screening and diagnostic compositions, methods and kits can be used in the monitoring of individuals who are undergoing and/or have been treated for localized colorectal cancer to determine if the cancer has metastasized. In vitro screening and diagnostic compositions, methods and kits can be used in the monitoring of individuals who are undergoing and/or have been treated for metastasized colorectal cancer to determine if the metastasized cancer has been eliminated. In vitro screening and diagnostic compositions, methods and kits can be used in the monitoring of individuals who are otherwise susceptible, i.e. individuals who have been identified as genetically predisposed such as by genetic screening and/or family histories. Advancements in the understanding of genetics and developments in technology as well as epidemiology allow for the determination of probability and risk assessment an individual has for developing colorectal cancer. Using family health histories and/or genetic screening, it is possible to estimate the probability that a particular individual has for developing certain types of cancer including colorectal cancer. Those individuals that have been identified as being predisposed to developing a particular form of cancer can be monitored or screened to detect evidence of metastasized colorectal cancer. Upon discovery of such evidence, early treatment can be undertaken to combat the disease. Accordingly, individuals who are at risk for developing metastasized colorectal cancer may be identified and samples may be isolated form such individuals. The invention is particularly useful for monitoring individuals who have been identified as having family medical histories which include relatives who have suffered from colorectal cancer. Likewise, the invention is particularly useful to monitor individuals who have been diagnosed as having colorectal cancer and, particularly those who have been treated and had tumors removed and/or are otherwise experiencing remission including those who have been treated for metastasized colorectal cancer.

In vitro screening and diagnostic compositions, methods and kits can be used in the analysis of tumors. Expression of CRCA-1 is a marker for cell type and allows for the identification of the origin of adenocarcinoma of unconfirmed origin as colorectal tumors as well as allowing for an initial diagnosis of colorectal cancer to be confirmed. Tumors believed to be colorectal in origin can be confirmed as such using the compositions, methods and kits of the invention. The invention can be used to confirm the diagnosis of colorectal cancer by confirming that tumors are of colorectal origin. Similarly, tumors of unknown origin can be analyzed and identified as being colorectal in origin using the compositions, methods and kits of the invention. The invention can be used to identify colorectal tumors in samples of tumors removed from individuals suffering from adenocarcinomas of unconfirmed origin.

In vitro screening and diagnostic compositions, kits and methods of the invention can be used to analyze tissue samples from the colon tissue to evaluate the extent of metastasis or invasion of colorectal tumor cells into the lamina propria. The lamina propria represents the barrier between the colorectal tract and the rest of the body; see *Bailey's Textbook of Histology*, 16th edition, Coperhaven et al. 1975 Williams and Wilkens, Baltimore MD at page 404 which is incorporated herein by reference. By identifying the presence of CRCA-1 transcript or translation products in cells of the lamina propria, the extent of invasion/infiltration of colorectal tumor cells into non-colorectal tissue can be evaluated and confirmed.

According to the invention, compounds are provided which bind to CRCA-1 transcript or translation products. Normal tissue in the body does not have CRCA-1 transcript or translation products except cells of the intestinal tract. Metastasized colorectal cells may be identified by detecting in non-colorectal samples CRCA-1 transcript or translation products. The expression of CRCA-1 is a marker for cell type and allows for the identification of colorectal metastasis in extra-intestinal samples. CRCA-1 transcript or translation products may be used to visualize colorectal derived cells from other cells of the lumen in order to evaluate the level of invasion of colorectal tumor cells into the basement membrane.

In some embodiments of the invention, non-colorectal tissue and fluid samples or tumor samples may be screened to identify the presence or absence of CRCA-1 translation products. Techniques such as ELISA assays and Western blots may be performed to determine whether one or more CRCA-1 translation products are present in a sample.

In some embodiments of the invention, non-colorectal tissue and fluid samples or tumor samples may be screened to identify whether one or more CRCA-1 translation products are being expressed in cells outside of the colorectal tract by detecting the presence or absence of CRCA-1 transcript. The presence of CRCA-1 transcript or cDNA generated therefrom can be determined using techniques such as PCR amplification, branched oligonucleotide technology, Northern Blots (mRNA), Southern Blots (cDNA), or oligonucleotide hybridization.

In some embodiments of the invention, cells of non-colorectal tissue samples or tumor samples may be examined to identify the presence or absence of one or more CRCA-1 translation products. Techniques such as immunohistochemistry blots may be performed on tissue sections to determine whether one or more CRCA-1 translation products are present in a sample.

In some embodiments of the invention, cells of non-colorectal tissue samples or tumor samples may be examined to determine whether one or more CRCA-1 translation products is being expressed in cells outside of the colorectal tract by detecting the presence or absence of the CRCA-1 transcript. The presence of the CRCA-1 transcript or cDNA generated therefrom in cells from tissue sections can be determined using techniques such as in situ hybridization.

The presence of one or more CRCA-1 translation products in non-colorectal tissue and fluid samples or on cells from non-colorectal tissue samples indicates colorectal tumor metastasis. The presence of one or more CRCA-1 translation products in a tumor sample or on tumor cells indicates that the tumor is colorectal in origin. The presence of the CRCA-1 transcript in non-colorectal tissue and fluid samples or in cells from non-colorectal tissue samples indicates colorectal tumor metastasis. The presence of the CRCA-1 transcript in tumor samples and tumor cells indicates that the tumor is colorectal in origin.

Some aspects of the present invention relate to methods and kits for evaluating the metastatic migration of tumor cells in the lamina propria, indicating the level of invasion of colorectal tumor cells into the basement membrane. In some embodiments of the invention, tissue samples which include sections of the lamina propria may be isolated from individuals undergoing or recovery from surgery to remove colorectal tumors. The tissue is analyzed to determine the extent of invasion into the basement membrane of the lamina propria by neoplastic colorectal cells. Identification of the presence or absence of the one or more CRCA-1 translation products confirms evaluation of the migration of tumor cells into the basement membrane indicating metastasis. Techniques such as immunohistochemistry assays may be performed to determine whether one or more CRCA-1 translation products are present in cells in the tissue sample which are indicative of metastatic migration. Alternatively, in some embodiments of the invention, tissue samples that include the lamina propria are analyzed to identify whether one or more CRCA-1 translation products are being expressed in cells in the tissue sample which indicate metastatic migration by detecting the presence or absence of the CRCA-1 transcript. The presence of the CRCA-1 transcript or cDNA generated therefrom can be determined using techniques such as in situ hybridization.

Samples from tumors may be identified as colorectal in origin by identification of expression of one or more CRCA-1 translation products using the methods of the invention. Samples of tumors removed from individuals suffering from adenocarcinomas of unconfirmed origin can be tested to determine whether or not they possess one or more CRCA-1 translation products or the CRCA-1 transcript. If the sample is removed from the intestinal tract, a section of frozen cells can be examined to determine if the tumor cells express one or more CRCA-1 translation products. If the sample is removed from the extra-intestinal tissue, a section of frozen cells can be examined to determine if the tumor cells express one or more CRCA-1 translation products or the sample can be homogenized and tested since the non-cancer cells will not possess one or more CRCA-1 translation products and therefore not present background.

Samples may be obtained from resected tissue or biopsy material including needle biopsy. Tissue section preparation for surgical pathology may be frozen and prepared using standard techniques. Immunohistochemistry and in situ hybridization binding assays on tissue sections are performed in fixed cells. Extra-intestinal samples may be homogenized by standard techniques such as sonication, mechanical disruption or chemical lysis such as detergent lysis. It is also contemplated that tumor samples in body such as blood, urine, lymph fluid, cerebral spinal fluid, amniotic fluid, vaginal fluid, semen and stool samples may also be screened to determine if such tumors are colorectal in origin.

Non-colorectal tissue samples may be obtained from any tissue except those of the colorectal tract, i.e. the intestinal tract below the small intestine (i.e. the large intestine (colon), including the cecum, ascending colon, transverse colon, descending colon, and sigmoid colon, and rectum) and additionally the duodenum and small intestine (jejunum and ileum). The cells of all tissue except those of the colorectal tract do not express one or more CRCA-1 translation products. Thus if one or more CRCA-1 translation products or the CRCA-1 transcript are detected in non-colorectal samples, the presence of metastatic colorectal cancer cells is indicated. In some preferred embodiments, the tissue samples are lymph nodes.

Tissue samples may be obtained by standard surgical techniques including use of biopsy needles. One skilled in the art would readily appreciate the variety of test samples that may be examined for one or more CRCA-1 translation products and recognize methods of obtaining tissue samples.

Tissue samples may be homogenized or otherwise prepared for screening for the presence of one or more CRCA-1 translation products by well known techniques such as sonication, mechanical disruption, chemical lysis such as detergent lysis or combinations thereof.

Examples of body fluid samples include blood, urine, lymph fluid, cerebral spinal fluid, amniotic fluid, vaginal fluid and semen. In some preferred embodiments, blood is used as a sample of body fluid. Cells may be isolated from fluid sample such as centrifugation. One skilled in the art would readily appreciate the variety of test samples that may be examined for one or more CRCA-1 translation products.

Test samples may be obtained by such methods as withdrawing fluid with a syringe or by a swab. One skilled in the art would readily recognize other methods of obtaining test samples.

In an assay using a blood sample, the blood plasma may be separated from the blood cells. The blood plasma may be screened for one or more CRCA-1 translation products including truncated proteins which are released into the blood when one or more CRCA-1 translation products are cleaved from or sloughed off from metastasized colorectal tumor cells. In some embodiments, blood cell fractions are screened for the presence of metastasized colorectal tumor cells. In some embodiments, lymphocytes present in the blood cell fraction are screened by lysing the cells and detecting the presence of one or more CRCA-1 translation products or the CRCA-1 transcript which may be present as a result of the presence of any metastasized colorectal tumor cells that may have been engulfed by the blood cell.

For aspects of the invention related to analysis of lumen tissue, the invention is useful to evaluate the level of metastatic migration of colorectal tumor cells using lumen samples taken from surgery patients at and near the site of the tumor. Some aspects of the invention provide methods of analyzing tissue samples which are fixed sections routinely prepared by surgical pathologists to characterize and evaluate cells. In some embodiments, the cells are from lamina propria and are analyzed to determine and evaluate the extent of metastasis of colorectal tumor cells. The lamina propria represents the barrier between the colorectal tract and the rest of the body. By identifying the presence of the CRCA-1 transcript or one or more CRCA-1 translation products in cells of the lamina propria, the extent of invasion/infiltration of colorectal tumor cells into non-colorectal tissue can be evaluated. In some embodiments, the cells are removed in a biopsy or as an adenocarcinoma of unknown origin and are analyzed to determine and evaluate the whether they are colorectal tumor cells. In some embodiments, the cells are from a tumor suspected of being colorectal in origin and the method and compositions and kits of the invention are used to confirm the identity of the origin of the tumor cells.

Samples of the lamina propria are removed during colorectal tumor removal surgery such as by resection or colonoscopy. The sample including basement membrane cells is frozen. If immunohistochemistry or in situ hybridization is to be performed, the frozen section is stained and then the assay is run. Those having ordinary skill in the art can readily isolate samples which include portions of the lamina propria and fix and stain them using standard techniques. By adding the visualization provided with a CRCA-1 detection technique, the section can be more comprehensively analyzed and the level of invasion of neoplastic colorectal cells into the lamina propria can be determined. The present invention may be used to analyze and evaluate the extent of progression of localized colorectal tumors, that is primary or non-metastatic colorectal tumors if these have penetrated the basement membrane underlying the mucosa into the submucosa.

Immunoassay methods may be used to identify individuals suffering from colorectal cancer metastasis by detecting presence of one or more CRCA-1 translation products in sample of non-colorectal tissue or body fluid using antibodies which were produced in response to exposure to such CRCA-1 translation product. Moreover, immunoassay methods may be used to identify individuals suffering from colorectal cancer by detecting presence of one or more CRCA-1 translation products in sample of tumor using antibodies which were produced in response to exposure to such CRCA-1 translation product.

The antibodies are preferably monoclonal antibodies. The antibodies are preferably raised against one or more CRCA-1 translation products made in human cells. Immunoassays are well known and there design may be routinely undertaken by those having ordinary skill in the art. Those having ordinary skill in the art can produce monoclonal antibodies which specifically bind to one of the several CRCA-1 translation products and are useful in methods and kits of the invention using standard techniques and readily available starting materials. The techniques for producing monoclonal antibodies are outlined in Harlow, E. and D. Lane, (1988) *ANTIBODIES: A Laboratory Manual*, Cold Spring Harbor Laboratory, Cold Spring Harbor N.Y., which is incorporated herein by reference, provide detailed guidance for the production of hybridomas and monoclonal antibodies which specifically bind to target proteins. It is within the scope of the present invention to include FAbs and F(Ab)2s which specifically bind to one or more CRCA-1 translation products in place of antibodies.

Briefly, a CRCA-1 translation product is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the CRCA-1 translation product, the hybridoma which produces them is cultured to produce a continuous supply of anti-CRCA-1 translation product specific antibodies.

The present invention relates to antibodies which are produced in response to exposure to a CRCA-1 translation product. The antibodies are preferably monoclonal antibodies. The antibodies are preferably raised against CRCA-1 translation product made in human cells.

The means to detect the presence of a protein in a test sample are routine and one having ordinary skill in the art can detect the presence or absence of a protein or an antibody using well known methods. One well known method of detecting the presence of a protein is an immunoassay. One having ordinary skill in the art can readily appreciate the multitude of ways to practice an immunoassay to detect the presence of a CRCA-1 translation product in a sample.

According to some embodiments, immunoassays comprise allowing proteins in the sample to bind a solid phase support such as a plastic surface. Detectable antibodies are then added which selectively binding to either the CRCA-1 translation product. Detection of the detectable antibody indicates the presence of CRCA-1 translation product. The detectable antibody may be a labelled or an unlabelled antibody. Unlabelled antibody may be detected using a second, labelled antibody that specifically binds to the first antibody or a second, unlabelled antibody which can be detected using labelled protein A, a protein that complexes with antibodies. Various immunoassay procedures are described in *Immunoassays for the 80's*, A. Voller et al., Eds., University Park, 1981, which is incorporated herein by reference.

Simple immunoassays may be performed in which a solid phase support is contacted with the test sample. Any proteins present in the test sample bind the solid phase support and can be detected by a specific, detectable antibody preparation. Such a technique is the essence of the dot blot, Western blot and other such similar assays.

Other immunoassays may be more complicated but actually provide excellent results. Typical and preferred immunometric assays include "forward" assays for the detection of a protein in which a first anti-protein antibody bound to a solid phase support is contacted with the test sample. After a suitable incubation period, the solid phase support is washed to remove unbound protein. A second, distinct anti-protein antibody is then added which is specific for a portion of the specific protein not recognized by the first antibody. The second antibody is preferably detectable. After a second incubation period to permit the detectable antibody to complex with the specific protein bound to the solid phase support through the first antibody, the solid phase support is washed a second time to remove the unbound detectable antibody. Alternatively, the second antibody may not be detectable. In this case, a third detectable antibody, which binds the second antibody is added to the system. This type of "forward sandwich" assay may be a simple yes/no assay to determine whether binding has occurred or may be made quantitative by comparing the amount of detectable antibody with that obtained in a control. Such "two-site" or "sandwich" assays are described by Wide, *Radioimmune Assay Method*, Kirkham, Ed., E. & S. Livingstone, Edinburgh, 1970, pp. 199–206, which is incorporated herein by reference.

Other types of immunometric assays are the so-called "simultaneous" and "reverse" assays. A simultaneous assay involves a single incubation step wherein the first antibody bound to the solid phase support, the second, detectable antibody and the test sample are added at the same time. After the incubation is completed, the solid phase support is washed to remove unbound proteins. The presence of detectable antibody associated with the solid support is then determined as it would be in a conventional "forward sandwich" assay. The simultaneous assay may also be adapted in a similar manner for the detection of antibodies in a test sample.

The "reverse" assay comprises the stepwise addition of a solution of detectable antibody to the test sample followed by an incubation period and the addition of antibody bound to a solid phase support after an additional incubation period. The solid phase support is washed in conventional fashion to remove unbound protein/antibody complexes and unreacted detectable antibody. The determination of detectable antibody associated with the solid phase support is then determined as in the "simultaneous" and "forward" assays. The reverse assay may also be adapted in a similar manner for the detection of antibodies in a test sample.

The first component of the immunometric assay may be added to nitrocellulose or other solid phase support which is capable of immobilizing proteins. The first component for determining the presence of CRCA-1 translation product in a test sample is an anti-CRCA-1 translation product antibody. By "solid phase support" or "Isupport" is intended any material capable of binding proteins. Well-known solid phase supports include glass, polystyrene, polypropylene, polyethylene, dextran, nylon, amylases, natural and modified celluloses, polyacrylamides, agaroses, and magnetite. The nature of the support can be either soluble to some extent or insoluble for the purposes of the present invention. The support configuration may be spherical, as in a bead, or cylindrical, as in the inside surface of a test tube or the external surface of a rod. Alternatively, the surface may be flat such as a sheet, test strip, etc. Those skilled in the art will know many other suitable "solid phase supports" for binding proteins or will be able to ascertain the same by use of routine experimentation. A preferred solid phase support is a 96-well microtiter plate.

To detect the presence of one or more CRCA-1 translation products, detectable anti-CRCA-1 translation product antibodies are used. Several methods are well known for the detection of antibodies.

One method in which the antibodies can be detectably labelled is by linking the antibodies to an enzyme and subsequently using the antibodies in an enzyme immunoassay (EIA) or enzyme-linked immunosorbent assay (ELISA), such as a capture ELISA. The enzyme, when subsequently exposed to its substrate, reacts with the substrate and generates a chemical moiety which can be detected, for example, by spectrophotometric, fluorometric or visual means. Enzymes which can be used to detectably label antibodies include, but are not limited to malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. One skilled in the art would readily recognize other enzymes which may also be used.

Another method in which antibodies can be detectably labelled is through radioactive isotopes and subsequent use in a radioimmunoassay (RIA) (see, for example, Work, T. S. et al., *Laboratory Techniques and Biochemistry in Molecular Biology*, North Holland Publishing Company, N.Y., 1978, which is incorporated herein by reference). The radioactive isotope can be detected by such means as the use of a gamma counter or a scintillation counter or by autoradiography. Isotopes which are particularly useful for the purpose of the present invention are $^3$H, 125I, 131I, $^{35}$S, and $^{14}$C. Preferably 125I is the isotope. One skilled in the art would readily recognize other radioisotopes which may also be used.

It is also possible to label the antibody with a fluorescent compound. When the fluorescent-labelled antibody is exposed to light of the proper wave length, its presence can be detected due to its fluorescence. Among the most commonly used fluorescent labeling compounds are fluorescein isothiocyanate, rhodamine, phycoerythrin, phycocyanin, allophycocyanin, o-phthaldehyde and fluorescamine. One skilled in the art would readily recognize other fluorescent compounds which may also be used.

Antibodies can also be detectably labelled using fluorescence-emitting metals such as 152Eu, or others of the lanthanide series. These metals can be attached to the protein-specific antibody using such metal chelating groups as diethylenetriaminepentaacetic acid (DTPA) or ethylenediamine-tetraacetic acid (EDTA). One skilled in the art would readily recognize other fluorescence-emitting metals as well as other metal chelating groups which may also be used.

Antibody can also be detectably labelled by coupling to a chemiluminescent compound. The presence of the chemiluminescent-labelled antibody is determined by detecting the presence of luminescence that arises during the course of a chemical reaction. Examples of particularly useful chemoluminescent labeling compounds are luminol, isoluminol, theromatic acridinium ester, imidazole, acridinium salt and oxalate ester. One skilled in the art would readily recognize other chemiluminescent compounds which may also be used.

Likewise, a bioluminescent compound may be used to label antibodies. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. One skilled in the art would readily recognize other bioluminescent compounds which may also be used.

Detection of the protein-specific antibody, fragment or derivative may be accomplished by a scintillation counter if, for example, the detectable label is a radioactive gamma emitter. Alternatively, detection may be accomplished by a fluorometer if, for example, the label is a fluorescent material. In the case of an enzyme label, the detection can be accomplished by colorometric methods which employ a substrate for the enzyme. Detection may also be accomplished by visual comparison of the extent of enzymatic reaction of a substrate in comparison with similarly prepared standards. One skilled in the art would readily recognize other appropriate methods of detection which may also be used.

The binding activity of a given lot of antibodies may be determined according to well known methods. Those skilled in the art will be able to determine operative and optimal assay conditions for each determination by employing routine experimentation.

Positive and negative controls may be performed in which known amounts of one or more CRCA-1 translation products and no CRCA-1 translation product, respectively, are added to assays being performed in parallel with the test assay. One skilled in the art would have the necessary knowledge to perform the appropriate controls. In addition, the kit may comprise instructions for performing the assay. Additionally the kit may optionally comprise depictions or photographs that represent the appearance of positive and negative results.

CRCA-1 translation products may be produced as a reagent for positive controls routinely. One skilled in the art would appreciate the different manners in which the CRCA-1 translation products may be produced and isolated.

Antibody composition refers to the antibody or antibodies required for the detection of the protein. For example, the antibody composition used for the detection of a CRCA-1 translation product in a test sample comprises a first antibody that binds to the CRCA-1 translation product as well as a second or third detectable antibody that binds the first or second antibody, respectively.

To examine a test sample for the presence of a CRCA-1 translation product, a standard immunometric assay such as the one described below may be performed. A first anti-CRCA-1 translation product antibody, which recognizes a specific portion of CRCA-1 translation product, is added to a 96-well microtiter plate in a volume of buffer. The plate is incubated for a period of time sufficient for binding to occur and subsequently washed with PBS to remove unbound antibody. The plate is then blocked with a PBS/BSA solution to prevent sample proteins from non-specifically binding the microtiter plate. Test sample are subsequently added to the wells and the plate is incubated for a period of time sufficient for binding to occur. The wells are washed with PBS to remove unbound protein. Labelled anti-CRCA-1 translation product antibodies, which recognize portions of CRCA-1 translation product not recognized by the first antibody, are added to the wells. The plate is incubated for a period of time sufficient for binding to occur and subsequently washed with PBS to remove unbound, labelled anti-CRCA-1 translation product antibody. The amount of labelled and bound anti-CRCA-1 translation product antibody is subsequently determined by standard techniques.

Kits which are useful for the detection of a CRCA-1 translation product in a test sample comprise a container comprising anti-CRCA-1 translation product antibodies and a container or containers comprising controls. Controls include one control sample which does not contain CRCA-1 translation product and/or another control sample which contained the CRCA-1 translation product. The anti-CRCA-1 translation product antibodies used in the kit are detectable such as being detectably labelled. If the detectable anti-CRCA-1 translation product antibody is not labelled, it may be detected by second antibodies or protein A for example which may also be provided in some kits in separate containers. Additional components in some kits include solid support, buffer, and instructions for carrying out the assay. Additionally the kit may optionally comprise depictions or photographs that represent the appearance of positive and negative results.

The immunoassay is useful for detecting one or more CRCA-1 translation products in homogenized tissue samples and body fluid samples including the plasma portion or cells in the fluid sample.

Western Blots may be used in methods of identifying individuals suffering from colorectal cancer metastasis by detecting presence of one or more CRCA-1 translation products of non-colorectal tissue or body fluid. Western blots may also be used to detect presence of one or more CRCA-1 translation products in sample of tumor from an individual suffering from cancer to identify and/or confirm that the tumor is colorectal in origin. Western blots use detectable anti-CRCA-1 translation product antibodies to bind to any CRCA-1 translation product present in a sample and thus indicate the presence of the receptor in the sample.

Western blot techniques, which are described in Sambrook, J. et al., (1989) *Molecular Cloning: A Laboratory Manual*, Cold Spring Harbor Laboratory Press, Cold Spring Harbor, N.Y., which is incorporated herein by reference, are similar to immunoassays with the essential difference being that prior to exposing the sample to the antibodies, the proteins in the samples are separated by gel electrophoresis and the separated proteins are then probed with antibodies. In some preferred embodiments, the matrix is an SDS-PAGE gel matrix and the separated proteins in the matrix are transferred to a carrier such as filter paper prior to probing with antibodies. Anti-CRCA-1 translation product antibodies described above are useful in Western blot methods.

Generally, samples are homogenized and cells are lysed using detergent such as Triton-X. The material is then separated by the standard techniques in Sambrook, J. et al., (1989) *Molecular Cloning: A Laboratory Manual*, Cold Spring Harbor Laboratory Press, Cold Spring Harbor, N.Y.

Kits which are useful for the detection of one or more CRCA-1 translation products in a test sample by Western Blot comprise a container comprising anti-CRCA-1 translation products antibodies and a container or containers comprising controls. Controls include one control sample which does not contain CRCA-1 translation product and/or another control sample which contained one or more CRCA-1 translation products. The anti-CRCA-1 translation product antibodies used in the kit are detectable such as being detectably labelled. If the detectable anti-CRCA-1 translation product antibody is not labelled, it may be detected by second antibodies or protein A for example which may also be provided in some kits in separate containers. Additional components in some kits include instructions for carrying out the assay. Additionally the kit may optionally comprise depictions or photographs that represent the appearance of positive and negative results.

Western blots are useful for detecting one or more CRCA-1 translation products in homogenized tissue samples and body fluid samples including the plasma portion or cells in the fluid sample.

In addition to detection of one or more CRCA-1 translation products, aspects of the present invention include various methods of determining whether a sample contains cells that express CRCA-1 by nucleotide sequence-based molecular analysis to detect the CRCA-1 transcript. Several different methods are available for doing so including those using Polymerase Chain Reaction (PCR) technology, branched oligonucleotide technology, Northern blot technology, oligonucleotide hybridization technology, and in situ hybridization technology.

The invention relates to oligonucleotide probes and primers used in the methods of identifying the CRCA-1 transcript and to diagnostic kits which comprise such components. The mRNA sequence-based methods for detect the CRCA-1 transcript include but are not limited to polymerase chain reaction technology, branched oligonucleotide technology, Northern and Southern blot technology, in situ hybridization technology and oligonucleotide hybridization technology.

The methods described herein are meant to exemplify how the present invention may be practiced and are not meant to limit the scope of invention. It is contemplated that other sequence-based methodology for detecting the presence of the CRCA-1 transcript in non-colorectal samples may be employed according to the invention.

A preferred method to detecting the CRCA-1 transcript in genetic material derived from non-colorectal samples uses polymerase chain reaction (PCR) technology. PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, CA (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. U.S. Pat. No. 4,683,202, U.S. Pat. No. 4,683,195, U.S. Pat. No. 4,965,188 and U.S. Pat. Nos 5,075,216, which are each incorporated herein by reference describe methods of performing PCR. PCR may be routinely practiced using Perkin Elmer Cetus GENE AMP RNA PCR kit, Part No. N808-0017.

PCR technology allows for the rapid generation of multiple copies of DNA sequences by providing 5' and 3' primers that hybridize to sequences present in an RNA or DNA molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the same small fragment of nucleic acid, exponential amplification of a specific double-stranded size product results. If only a single primer hybridizes to the nucleic acid fragment, linear amplification produces single-stranded products of variable length.

PCR primers can be designed routinely by those having ordinary skill in the art using sequence information. The nucleotide sequence of the the CRCA-1 transcript is set forth in SEQ ID NO:1. To perform this method, RNA is extracted from cells in a sample and tested or used to make cDNA using well known methods and readily available starting materials. Those having ordinary skill in the art can readily prepare PCR primers. A set of primers generally contains two primers. When performing PCR on extracted mRNA or cDNA generated therefrom, if the CRCA-1 transcript or cDNA generated thererefrom is present, multiple copies of the mRNA or cDNA will be made. If it is not present, PCR will not generate a discrete detectable product. Primers are generally 8–50 nucleotides, preferably about 15–35 nucleotides, more preferably 18–28 nucleotides, which are identical or complementary to and therefor hybridize to the CRCA-1 transcript or cDNA generated therefrom. In preferred embodiments, the primers are each 15–35 nucleotide, more preferably 18–28 nucleotide fragments of SEQ ID NO:1. The primer must hybridize to the sequence to be amplified. Typical primers are 18–28 nucleotides in length and are generally have 500 to 60% G+C composition. The entire primer is preferably complementary to the sequence it must hybridize to. Preferably, primers generate PCR products 100 base pairs to 2000 base pairs. However, it is possible to generate products of 50 to up to 10 kb and more. If mRNA is used as a template, the primers must hybridize to mRNA sequences. If cDNA is used as a template, the primers must hybridize to cDNA sequences. At least one primer hybridizes to a unique nucleotide sequence not found on mRNA that encodes ST receptor protein.

The mRNA or cDNA is combined with the primers, free nucleotides and enzyme following standard PCR protocols. The mixture undergoes a series of temperature changes. If the CRCA-1 transcript or cDNA generated therefrom is present, that is, if both primers hybridize to sequences on the same molecule, the molecule comprising the primers and the intervening complementary sequences will be exponentially amplified. The amplified DNA can be easily detected by a variety of well known means. If no CRCA-1 transcript or cDNA generated therefrom is present, no PCR product will be exponentially amplified. The PCR technology therefore provides an extremely easy, straightforward and reliable method of detecting the CRCA-1 transcript in a sample.

PCR product may be detected by several well known means. The preferred method for detecting the presence of amplified DNA is to separate the PCR reaction material by gel electrophoresis and stain the gel with ethidium bromide in order to visual the amplified DNA if present. A size standard of the expected size of the amplified DNA is preferably run on the gel as a control.

In some instances, such as when unusually small amounts of RNA are recovered and only small amounts of cDNA are generated therefrom, it is desirable or necessary to perform a PCR reaction on the first PCR reaction product. That is, if difficult to detect quantities of amplified DNA are produced by the first reaction, a second PCR can be performed to make multiple copies of DNA sequences of the first amplified DNA. A nested set of primers are used in the second PCR reaction. The nested set of primers hybridize to sequences downstream of the 5' primer and upstream of the 3' primer used in the first reaction.

The present invention includes oligonucleotide which are useful as primers for performing PCR methods to amplify the CRCA-1 transcript or cDNA generated therefrom.

According to the invention, diagnostic kits can be assembled which are useful to practice methods of detecting the presence of the CRCA-1 transcript or cDNA generated therefrom in non-colorectal samples. Such diagnostic kits comprise oligonucleotide which are useful as primers for performing PCR methods. It is preferred that diagnostic kits according to the present invention comprise a container comprising a size marker to be run as a standard on a gel used to detect the presence of amplified DNA. The size marker is the same size as the DNA generated by the primers in the presence of the the CRCA-1 transcript or cDNA generated therefrom. Additional components in some kits include instructions for carrying out the assay. Additionally the kit may optionally comprise depictions or photographs that represent the appearence of positive and negative results.

PCR assays are useful for detecting the CRCA-1 transcript in homogenized tissue samples and cells in body fluid samples. It is contemplated that PCR on the plasma portion of a fluid sample could be used to detect the CRCA-1 transcript.

Another method of determining whether a sample contains cells expressing CRCA-1 is by branched chain oligonucleotide hybridization analysis of mRNA extracted from a sample. Branched chain oligonucleotide hybridization may be performed as described in U.S. Pat. No. 5,597,909, U.S. Pat. No. 5,437,977 and U.S. Pat. No. 5,430,138, which are each incorporated herein by reference. Reagents may be designed following the teachings of those patents and that sequence of the CCRA-1 transcript.

Another method of determining whether a sample contains cells expressing CRCA-1 is by Northern Blot analysis of mRNA extracted from a non-colorectal sample. The techniques for performing Northern blot analyses are well known by those having ordinary skill in the art and are described in Sambrook, J. et al., (1989) *Molecular Cloning: A Laboratory Manual*, Cold Spring Harbor Laboratory Press, Cold Spring Harbor, N.Y. mRNA extraction, electrophoretic separation of the mRNA, blotting, probe preparation and hybridization are all well known techniques that can be routinely performed using readily available starting material.

The mRNA is extracted using poly dT columns and the material is separated by electrophoresis and, for example, transferred to nitrocellulose paper. Labelled probes made from an isolated specific fragment or fragments can be used to visualize the presence of a complementary fragment fixed to the paper. Probes useful to identify mRNA in a Northern Blot have a nucleotide sequence that is complementary to the CRCA-1 transcript. Those having ordinary skill in the art could use the sequence information in SEQ ID NO:1 to design such probes or to isolate and clone the the CRCA-1 transcript or cDNA generated therefrom to be used as a probe. Such probes are at least 15 nucleotides, preferably 30–200, more preferably 40–100 nucleotide fragments and may be the entire CRCA-1 transcript.

According to the invention, diagnostic kits can be assembled which are useful to practice methods of detecting the presence of the CRCA-1 transcript in non-colorectal samples by Northern blot analysis. Such diagnostic kits comprise oligonucleotide which are useful as probes for hybridizing to the mRNA. The probes may be radiolabelled. It is preferred that diagnostic kits according to the present invention comprise a container comprising a size marker to be run as a standard on a gel. It is preferred that diagnostic kits according to the present invention comprise a container comprising a positive control which will hybridize to the probe. Additional components in some kits include instructions for carrying out the assay. Additionally the kit may optionally comprise depictions or photographs that represent the appearence of positive and negative results.

Northern blot analysis is useful for detecting the CRCA-1 transcript in homogenized tissue samples and cells in body fluid samples. It is contemplated that PCR on the plasma portion of a fluid sample could be used to detect the CRCA-1 transcript.

Another method of detecting the presence of the CRCA-1 transcript by oligonucleotide hybridization technology. Oligonucleotide hybridization technology is well known to those having ordinary skill in the art. Briefly, detectable probes which contain a specific nucleotide sequence that will hybridize to nucleotide sequence of the CRCA-1 transcript. RNA or cDNA made from RNA from a sample is fixed, usually to filter paper or the like. The probes are added and maintained under conditions that permit hybridization only if the probes fully complement the fixed genetic material. The conditions are sufficiently stringent to wash off probes in which only a portion of the probe hybridizes to the fixed material. Detection of the probe on the washed filter indicate complementary sequences.

Probes useful in oligonucleotide assays at least 18 nucleotides of complementary DNA and may be as large as a complete complementary sequence to the CRCA-1 transcript. In some preferred embodiments the probes of the invention are 30–200 nucleotides, preferably 40–100 nucleotides. The probes preferably contain a sequence that is unique with respect to the sequence that encodes the ST receptor.

One having ordinary skill in the art, using the sequence information disclosed in SEQ ID NO:1 can design probes which are fully complementary to the CRCA-1 transcript but not the sequence that encodes ST receptor. Hybridization conditions can be routinely optimized to minimize background signal by non-fully complementary hybridization. In some preferred embodiments, the probes are full length clones. Probes are at least 15 nucleotides, preferably 30–200, more preferably 40–100 nucleotide fragments and may be the entire CRCA-1 transcript.

The present invention includes labelled oligonucleotide which are useful as probes for performing oligonucleotide hybridization. That is, they are fully complementary with the CRCA-1 transcript but not the ST receptor transcript. For example, the mRNA sequence includes portions encoded by different exons. The labelled probes of the present invention are labelled with radiolabelled nucleotides or are otherwise detectable by readily available nonradioactive detection systems.

According to the invention, diagnostic kits can be assembled which are useful to practice oligonucleotide hybridization methods of the invention. Such diagnostic kits comprise a labelled oligonucleotide which encodes portions of the CRCA-1 transcript different from coding sequences that encode ST receptor. It is preferred that labelled probes of the oligonucleotide diagnostic kits according to the present invention are labelled with a radionucleotide. The oligonucleotide hybridization-based diagnostic kits according to the invention preferably comprise DNA samples that represent positive and negative controls. A positive control DNA sample is one that comprises a nucleic acid molecule which has a nucleotide sequence that is fully complementary to the probes of the kit such that the probes will hybridize to the molecule under assay conditions. A negative control DNA sample is one that comprises at least one nucleic acid molecule, the nucleotide sequence of which is partially complementary to the sequences of the probe of the kit. Under assay conditions, the probe will not hybridize to the negative control DNA sample. Additional components in some kits include instructions for carrying out the assay. Additionally the kit may optionally comprise depictions or photographs that represent the appearence of positive and negative results.

Oligonucleotide hybridization techniques are useful for detecting the CRCA-1 transcript in homogenized tissue samples and cells in body fluid samples. It is contemplated that PCR on the plasma portion of a fluid sample could be used to detect the CRCA-1 transcript.

The present invention relates to in vitro kits for evaluating tissues samples to determine the level of metastasis and to reagents and compositions useful to practice the same.

In some embodiments of the invention, tissue samples that include portions of the lamina propria may be isolated from individuals undergoing or recovery from surgery to remove colorectal tumors include resection or colonoscopy. The tissue is analyzed to identify the presence or absence of the CRCA-1 transcript. Techniques such as immunohistochemistry assays may be performed to determine whether the one or more CRCA-1 translation products is present in cells in the tissue sample which are indicative of metastatic migration. In some embodiments of the invention, tissue samples are analyzed to identify whether the CRCA-1 is being expressed in cells in the tissue sample which indicate metastatic migration by detecting the presence or absence of the CRCA-1 transcript or one or more CRCA-1 translation products. The presence of the CRCA-1 transcript or cDNA generated therefrom can be determined using techniques such as in situ hybridization or immunohistochemistry.

The present invention relates to in vitro kits for evaluating samples of tumors to determine whether or not they are colorectal in origin and to reagents and compositions useful to practice the same. In some embodiments of the invention, tumor samples may be isolated from individuals undergoing or recovery from surgery to remove tumors in the colon, tumors in other organs or biopsy material. The tumor sample is analyzed to identify the presence or absence of the CRCA-1 transcript. Techniques such as immunohistochemistry assays may be performed to determine whether one or more CRCA-1 translation products are present in cells in the tumor sample which are indicative of colorectal origin. Alternatively, in some embodiments of the invention, lumen tissue samples are analyzed to identify whether CRCA-1 is being expressed in cells in the tumor sample which indicate colorectal origin by detecting the presence or absence of the CRCA-1 transcript or one or more CRCA-1 translation products. The presence of mRNA that encodes the ST receptor protein or cDNA generated therefrom can be determined using techniques such as in situ hybridization, immunohistochemistry and in situ ST binding assay.

In situ hybridization technology is well known by those having ordinary skill in the art. Briefly, cells are fixed and detectable probes which contain a specific nucleotide sequence are added to the fixed cells. If the cells contain complementary nucleotide sequences, the probes, which can be detected, will hybridize to them.

Probes useful in oligonucleotide assays at least 18 nucleotides of complementary DNA and may be as large as a complete complementary sequence to the CRCA-1 transript. In some preferred embodiments the probes of the invention are 30–200 nucleotides, preferably 40–100 nucleotides. The probes contain a sequence that is unique from those that encode the ST receptor.

One having ordinary skill in the art, using the sequence information set forth in SEQ ID NO:1 and the known sequence for human ST receptor mRNA can design probes useful in in situ hybridization technology to identify cells that express CRCA-1. Probes preferably hybridizes to a nucleotide sequence that corresponds to the CRCA-1 transcript. Hybridization conditions can be routinely optimized to minimize background signal by non-fully complementary hybridization and cross hybridization to sequences encoding ST receptors. Probes preferably hybridize to the full length CRCA-1 transcript. Probes are at least 15 nucleotides, preferably 30–200, more preferably 40–100 nucleotide fragments and may be the CRCA transcript, more preferably 18–28 nucleotide fragments of the CRCA-1 transcript.

The probes are fully complementary and do not hybridize well to partially complementary sequences. For in situ hybridization according to the invention, it is preferred that the probes are detectable by fluorescence. A common procedure is to label probe with biotin-modified nucleotide and then detect with fluorescently tagged avidin. Hence, probe does not itself have to be labelled with florescent but can be subsequently detected with florescent marker.

The present invention includes labelled oligonucleotide which are useful as probes for performing oligonucleotide hybridization. That is, they are fully complementary with mRNA sequences but not genomic sequences or ST recpetor mRNA. For example, the mRNA sequence includes portions encoded by different exons. The labelled probes of the present invention are labelled with radiolabelled nucleotides or are otherwise detectable by readily available nonradioactive detection systems. The present invention relates to probes useful for in situ hybridization to identify cells that express CRCA-1.

Cells are fixed and the probes are added to the genetic material. Probes will hybridize to the complementary nucleic acid sequences present in the sample. Using a fluorescent microscope, the probes can be visualized by their fluorescent markers.

According to the invention, diagnostic kits can be assembled which are useful to practice in situ hybridization methods of the invention are fully complementary with mRNA sequences but not genomic sequences. For example, the mRNA sequence includes different exon sequences. It is preferred that labelled probes of the in situ diagnostic kits according to the present invention are labelled with a fluorescent marker.

Those having ordinary skill in the art can analyze the fixed cells to characterize the level of metastatic migration of the colon cancer cells. The labelling of colon-derived cells allows for improved analysis.

Immunohistochemistry techniques may be used to identify and essentially stain cells with one or more CRCA-1 translation products. Such "staining" allows for analysis of metastatic migration. Anti-CRCA-1 translation product antibodies such as those described above of contacted with fixed cells and the CRCA-1 translation products present in the cells reacts with the antibodies. The antibodies are detectably labelled or detected using labelled second antibody or protein A to stain the cells.

The techniques described herein for evaluating tumor sections can also be used to analyze tissue sections for samples of lymph nodes as well as other tissues to identify the presence of colorectal tumor cells. The samples can be prepared and "stained" to detect expression of CRCA-1.

In vivo Imaging and Therapeutics

According to some embodiments of the invention, compositions and in vivo methods are provided for detecting, imaging, or treating colorectal tumors in an individual.

The conjugated compositions of the present invention are useful for targeting cells that line the inner intestine wall including cancer cells derived from such cells, particularly metastasized cancer cells derived from such cells.

When the conjugated compositions of the present invention are administered outside the intestinal tract such as when administered in the circulatory system, they remain segregated from the cells that line the intestinal tract and will bind only to cells outside the intestinal tract which are derived from the intestinal tract such as metastasized colorectal cells. The conjugated compositions will not bind to non-colorectal derived cells. Thus, the active moieties of conjugated compositions administered outside the intestinal tract are delivered to cells which are derived from the intestinal tract such as metastasized colorectal cells but will not be delivered to any other cells.

Therapeutic and diagnostic pharmaceutical compositions of the present invention include conjugated compounds specifically targeted to metastatic disease. These conjugated compounds include moieties that bind to one or more CRCA-1 translation products which do not bind to cells of normal tissue in the body except cells of the intestinal tract since the cells of other tissues do not possess such translation products. Further, according to the invention, the CRCA-1 translation product binding moieties do not bind to ST receptors.

Unlike normal colorectal cells and localized colorectal cancer cells, metastasized colorectal cancer cells are accessible to substances administered outside the intestinal tract, for example administered in the circulatory system. The only CRCA-1 translation products in normal tissue exist in the apical membranes of intestinal mucosa cells and thus effectively isolated from the targeted cancer chemotherapeutics and imaging agents administered outside the intestinal tract by the intestinal mucosa barrier. Thus, metastasized colorectal cells may be targeted by conjugated compounds of the present invention by introducing such compounds outside the intestinal tract such as for example by administering pharmaceutical compositions that comprise conjugated compounds into the circulatory system.

One having ordinary skill in the art can identify individuals suspected of suffering from colorectal cancer and metastasized colorectal cells. In those individuals diagnosed with colorectal cancer, it is standard therapy to suspect metastasis and aggressively attempt to eradicate metastasized cells. The present invention provides pharmaceutical compositions and methods for imaging and thereby will more definitively diagnose metastasis. Further, the present invention provides pharmaceutical compositions comprising therapeutic agents and methods for specifically targeting and eliminating metastasized colorectal cancer cells. Further, the present invention provides pharmaceutical compositions that comprise therapeutics and methods for specifically eliminating colorectal cancer cells.

The pharmaceutical compositions which comprise conjugated compositions of the present invention may be used to diagnose or treat individuals suffering from localized colorectal tumors, that is primary or non-metastatic colorectal tumors if these have penetrated the basement membrane underlying the mucosa into the submucosa where there is abundant blood supply to which they have access. Penetration into the submucosa circumvents the mucosal barrier resulting in the ability of conjugated compositions introduced into the circulatory system to interact with these tumors.

The present invention relies upon the use of a CRCA-1 translation product binding moiety in a conjugated composition. The CRCA-1 translation product binding moiety is essentially a portion of the conjugated composition which acts as a ligand to a CRCA-1 translation product and thus specifically binds to it. The conjugated composition also includes an active moiety which is associated with the CRCA-1 translation product binding moiety; the active moiety being an active agent which is either useful to image, target, neutralize or kill the cell.

According to the present invention, the CRCA-1 translation product binding moiety is the CRCA-1 translation product ligand portion of a conjugated composition. In some embodiments, the CRCA-1 translation product ligand is an antibody.

In some preferred embodiments, conjugated compounds comprise CRCA-1 translation product binding moieties that comprise an anti-CRCA-1 translation product antibody.

It is preferred that the CRCA-1 translation product ligand used as the CRCA-1 translation product binding moiety be as small as possible. Thus it is preferred that the CRCA-1 translation product ligand be a non-peptide small molecule or small peptide, preferably less than 25 amino acids, more preferably less than 20 amino acids. In some embodiments, the CRCA-1 translation product ligand which constitute the CRCA-1 translation product binding moiety of a conjugated composition is less than 15 amino acids. CRCA-1 translation product binding peptide comprising less than 10 amino acids and CRCA-1 translation product binding peptide less than 5 amino acids may be used as CRCA-1 translation product binding moieties according to the present invention. It is within the scope of the present invention to include larger molecules which serve as CRCA-1 translation product binding moieties including, but not limited to molecules such as antibodies which specifically bind to CRCA-1 translation product.

CRCA-1 translation product ligands useful as CRCA-1 translation product binding moieties may be identifed using various well known combinatorial library screening technologies such as those set forth in Example 1 herein.

An assay may be used to test both peptide and non-peptide compositions to determine whether or not they are CRCA-1 translation product ligands or, to test conjugated compositions to determine if they possess CRCA-1 translation product binding activity. Such compositions that specifically bind to CRCA-1 translation product can be identified by a competitive binding assay using antibodies known to bind to the CRCA-1 translation product. The competitive binding assay is a standard technique in pharmacology which can be readily performed by those having ordinary skill in the art using readily available starting materials.

CRCA-1 translation products may be produced synthetically, recombinantly or isolated from natural sources.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptide of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

CRCA-1 translation products and conjugated compositions or portions thereof which are peptides may also be prepared by recombinant DNA techniques. Provision of a suitable DNA sequence encoding the desired peptide permits the production of the peptide using recombinant techniques now known in the art. The coding sequence can be obtained from natural sources or synthesized or otherwise constructed using widely available starting materials by routine methods. When the coding DNA is prepared synthetically, advantage can be taken of known codon preferences of the intended host where the DNA is to be expressed.

To produce a CRCA-1 translation product which occurs in nature, one having ordinary skill in the art can, using well-known techniques, obtain a DNA molecule encoding the CRCA-1 translation product and insert that DNA molecule into a commercially available expression vector for use in well-known expression systems such as for example those described herein.

For example, the commercially available plasmid pSE420 (Invitrogen, San Diego, Calif.) may be used for recombinant production in *E. coli*. The commercially available plasmid pYES2 (Invitrogen, San Diego, Calif.) may be used for production in *S. cerevisiae* strains of yeast. The commercially available MaxBac™ (Invitrogen, San Diego, Calif.) complete baculovirus expression system may be used for production in insect cells. The commercially available plasmid pcDNA I (Invitrogen, San Diego, CA) may be used for production in mammalian cells such as Chinese Hamster Ovary cells.

One having ordinary skill in the art may use these or other commercially available expression vectors and systems or produce vectors using well-known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989). Thus, the desired proteins can be prepared in both prokaryotic and eukaryotic systems, resulting in a spectrum of processed forms of the protein.

The most commonly used prokaryotic system remains E. coli, although other systems such as B. subtilis and Pseudomonas are also useful. Suitable control sequences for prokaryotic systems include both constitutive and inducible promoters including the lac promoter, the trp promoter, hybrid promoters such as tac promoter, the lambda phage P1 promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in prokaryotic hosts in this matter, the signal sequence is removed upon secretion.

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but are not limited to, yeast, fungal cells, insect cells, mammalian cells, avian cells, and cells of higher plants. Suitable promoters are available which are compatible and operable for use in each of these host types as well as are termination sequences and enhancers, as e.g. the baculovirus polyhedron promoter. As above, promoters can be either constitutive or inducible. For example, in mammalian systems, the mouse metallothionene promoter can be induced by the addition of heavy metal ions.

The particulars for the construction of expression systems suitable for desired hosts are known to those in the art. For recombinant production of the protein, the DNA encoding it is suitably ligated into the expression vector of choice and then used to transform the compatible host which is then cultured and maintained under conditions wherein expression of the foreign gene takes place. The protein of the present invention thus produced is recovered from the culture, either by lysing the cells or from the culture medium as appropriate and known to those in the art.

One having ordinary skill in the art can, using well-known techniques, isolate the protein that is produced.

According to the present invention, the active moiety may be a therapeutic agent or an imaging agent. One having ordinary skill in the art can readily recognize the advantages of being able to specifically target metastasized colorectal cells with an CRCA-1 translation product ligand and conjugate such a ligand with many different active agents.

Chemotherapeutics useful as active moieties which when conjugated to a CRCA-1 translation product binding moiety are specifically delivered to metastasized colorectal cells are typically, small chemical entities produced by chemical synthesis. Chemotherapeutics include cytotoxic and cytostatic drugs. Chemotherapeutics may include those which have other effects on cells such as reversal of the transformed state to a differentiated state or those which inhibit cell replication. Examples of chemotherapeutics include common cytotoxic or cytostatic drugs such as for example: methotrexate (amethopterin), doxorubicin (adrimycin), daunorubicin, cytosinarabinoside, etoposide, 5-4 fluorouracil, melphalan, chlorambucil, and other nitrogen mustards (e.g. cyclophosphamide), cis-platinum, vindesine (and other vinca alkaloids), mitomycin and bleomycin. Other chemotherapeutics include: purothionin (barley flour oligopeptide), macromomycin. 1,4-benzoquinone derivatives and trenimon.

Toxins are useful as active moieties. When a toxin is conjugated to a CRCA-1 translation product binding moiety, the conjugated composition is specifically delivered to a metastasized colorectal cell by way of the CRCA-1 translation product binding moiety and the toxin moiety kills the cell. Toxins are generally complex toxic products of various organisms including bacteria, plants, etc. Examples of toxins include but are not limited to: ricin, ricin A chain (ricin toxin), Pseudomonas exotoxin (PE), diphtheria toxin (DT), *Clostridium perfringens* phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin and volkensin. As discussed above, when protein toxins are employed with CRCA-1 translation product binding peptides, conjugated compositions may be produced using recombinant DNA techniques. Briefly, a recombinant DNA molecule can be constructed which encodes both the CRCA-1 translation product ligand and the toxin on a chimeric gene. When the chimeric gene is expressed, a fusion protein is produced which includes a CRCA-1 translation product binding moiety and an active moiety. Protein toxins are also useful to form conjugated compounds with CRCA-1 translation product binding peptides through non-peptidyl bonds.

In addition, there are other approaches for utilizing active agents for the treatment of cancer. For example, conjugated compositions may be produced which include a CRCA-1 translation product binding moiety and an active moiety which is an active enzyme. The CRCA-1 translation product binding moiety specifically localizes the conjugated composition to the tumor cells. An inactive prodrug which can be converted by the enzyme into an active drug is administered to the patient. The prodrug is only converted to an active drug by the enzyme which is localized to the tumor. An example of an enzyme/prodrug pair includes alkaline phosphatase/ etoposidephosphate. In such a case, the alkaline phosphatase is conjugated to a CRCA-1 translation product binding ligand. The conjugated compound is administered and localizes at the metastasized cell. Upon contact with etoposidephosphate (the prodrug), the etoposidephosphate is converted to etoposide, a chemotherapeutic drug which is taken up by the cancer cell.

Radiosensitizing agents are substances that increase the sensitivity of cells to radiation. Examples of radiosensitizing agents include nitroimidazoles, metronidazole and misonidazole (see: DeVita, V. T. Jr. in *Harrison's Principles of Internal Medicine*, p.68, McGraw-Hill Book Co., N.Y. 1983, which is incorporated herein by reference). The conjugated compound that comprises a radiosensitizing agent as the active moiety is administered and localizes at the metastasized cell. Upon exposure of the individual to radiation, the radiosensitizing agent is "excited" and causes the death of the cell.

Radionuclides may be used in pharmaceutical compositions that are useful for radiotherapy or imaging procedures.

Examples of radionuclides useful as toxins in radiation therapy include: $^{47}$Sc, $^{67}$Cu, 90Y, $^{109}$Pd, 123I, 125I, $^{131}$I, $^{186}$Re, $^{188}$Re, $^{199}$Au, $^{211}$At, $^{212}$Pb and $^{212}$B. Other radionuclides which have been used by those having ordinary skill in the art include: $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193}$Pt, $^{197}$Hg, all beta negative and/or auger emitters. Some preferred radionuclides include: $^{90}$Y, $^{131}$I, $^{211}$At and $^{212}$Pb/$^{212}$Bi.

According to the present invention, the active moieties may be an imaging agent. Imaging agents are useful diagnostic procedures as well as the procedures used to identify the location of metastasized cells. Imaging can be performed by many procedures well-known to those having ordinary skill in the art and the appropriate imaging agent useful in such procedures may be conjugated to a CRCA-1 translation product ligand by well-known means. Imaging can be performed, for example, by radioscintigraphy, nuclear magnetic resonance imaging (MRI) or computed tomography (CT scan). The most commonly employed radionuclide imaging agents include radioactive iodine and indium. Imaging by CT scan may employ a heavy metal such as iron chelates. MRI scanning may employ chelates of gadolinium or manganese. Additionally, positron emission tomography (PET) may be possible using positron emitters of oxygen, nitrogen, iron, carbon, or gallium. Example of radionuclides useful in imaging procedures include: $^{43}$K, $^{52}$Fe, 57Co, $^{67}$Cu, $^{67}$Ga, $^{68}$Ga, 77Br, 81Rb/$^{81M}$Kr, $^{87M}$Sr, $^{99M}$Tc, $^{111}$In, $^{113M}$In, $^{123}$I, $^{125}$I, $^{127}$Cs, $^{129}$Cs, 131I, $^{132}$I, $^{197}$Hg, $^{203}$Pb and $^{206}$Bi.

It is preferred that the conjugated compositions be non-immunogenic or immunogenic at a very low level. Accordingly, it is preferred that the CRCA-1 translation product binding moiety be a small, poorly immunogenic or non-immunogenic peptide or a non-peptide. Alternatively, the CRCA-1 translation product binding moiety may be a humanized or primatized antibody or a human antibody.

CRCA-1 translation product ligands are conjugated to active agents by a variety of well-known techniques readily performed without undue experimentation by those having ordinary skill in the art. The technique used to conjugate the CRCA-1 translation product ligand to the active agent is dependent upon the molecular nature of the CRCA-1 translation product ligand and the active agent. After the CRCA-1 translation product ligand and the active agent are conjugated to form a single molecule, assays may be performed to ensure that the conjugated molecule retains the activities of the moieties. The competitive binding assay described above may be used to confirm that the CRCA-1 translation product binding moiety retains its binding activity as a conjugated compound. Similarly, the activity of the active moiety may be tested using various assays for each respective type of active agent. Radionuclides retain there activity, i.e. their radioactivity, irrespective of conjugation. With respect to active agents which are toxins, drugs and targeting agents, standard assays to demonstrate the activity of unconjugated forms of these compounds may be used to confirm that the activity has been detained.

Conjugation may be accomplished directly between the CRCA-1 translation product ligand and the active agent or linking, intermediate molecular groups may be provided between the CRCA-1 translation product ligand and the active agent. Crosslinkers are particularly useful to facilitate conjugation by providing attachment sites for each moiety. Crosslinkers may include additional molecular groups which serve as spacers to separate the moieties from each other to prevent either from interfering with the activity of the other.

One having ordinary skill in the art may conjugate a CRCA-1 translation product ligand to a chemotherapeutic drug using well-known techniques. For example, Magerstadt, M. *Antibody Conjugates and Malignant Disease.* (1991) CRC Press, Boca Raton, USA, pp. 110–152) which is incorporated herein by reference, teaches the conjugation of various cytostatic drugs to amino acids of antibodies. Such reactions may be applied to conjugate chemotherapeutic drugs to CRCA-1 translation product ligands, including anti-CRCA-1 translation product antibodies, with an appropriate linker. Most of the chemotherapeutic agents currently in use in treating cancer possess functional groups that are amenable to chemical crosslinking directly with proteins. For example, free amino groups are available on methotrexate, doxorubicin, daunorubicin, cytosinarabinoside, cis-platin, vindesine, mitomycin and bleomycin while free carboxylic acid groups are available on methotrexate, melphalan, and chlorambucil. These functional groups, that is free amino and carboxylic acids, are targets for a variety of homobifunctional and heterobifunctional chemical crosslinking agents which can crosslink these drugs directly to the single free amino group of an antibody. For example, one procedure for crosslinking CRCA-1 translation product ligands which have a free amino group to active agents which have a free amino group such as methotrexate, doxorubicin, daunorubicin, cytosinarabinoside, cis-platin, vindesine, mitomycin and bleomycin, or alkaline phosphatase, or protein- or peptide-based toxin employs homobifunctional succinimidyl esters, preferably with carbon chain spacers such as disuccinimidyl suberate (Pierce Co, Rockford, Ill.). In the event that a cleavable conjugated compound is required, the same protocol would be employed utilizing 3,3'- dithiobis (sulfosuccinimidylpropionate; Pierce Co.).

In order to conjugate a CRCA-1 translation product ligand that is a peptiode or protein to a peptide-based active agent such as a toxin, the CRCA-1 translation product ligand and the toxin may be produced as a single, fusion protein either by standard peptide synthesis or recombinant DNA technology, both of which can be routinely performed by those having ordinary skill in the art. Alternatively, two peptides, the CRCA-1 translation product ligand peptide and the peptide-based toxin may be produced and/or isolated as separate peptides and conjugated using crosslinkers. As with conjugated compositions that contain chemotherapeutic drugs, conjugation of CRCA-1 translation product binding peptides and toxins can exploit the ability to modify the single free amino group of a CRCA-1 translation product binding peptide while preserving the receptor-binding function of this molecule.

One having ordinary skill in the art may conjugate a CRCA-1 translation product ligand to a radionuclide using well-known techniques. For example, Magerstadt, M. (1991) *Antibody Conjugates And Malignant Disease*, CRC Press, Boca Raton, Fla.; and Barchel, S. W. and Rhodes, B. H., (1983) *Radioimaging and Radiotherapy*, Elsevier, NY, N.Y., each of which is incorporated herein by reference, teach the conjugation of various therapeutic and diagnostic radionuclides to amino acids of antibodies.

The present invention provides pharmaceutical compositions that comprise the conjugated compounds of the invention and pharmaceutically acceptable carriers or diluents. The pharmaceutical composition of the present invention may be formulated by one having ordinary skill in the art. Suitable pharmaceutical carriers are described in Remington's Pharmaceutical Sciences, A. Osol, a standard reference text in this field, which is incorporated herein by reference. In carrying out methods of the present invention, conjugated compounds of the present invention can be used alone or in combination with other diagnostic, therapeutic or additional agents. Such additional agents include excipients such as coloring, stabilizing agents, osmotic agents and antibacterial agents. Pharmaceutical compositions are preferably sterile and pyrogen free.

The conjugated compositions of the invention can be, for example, formulated as a solution, suspension or emulsion in association with a pharmaceutically acceptable parenteral vehicle. Examples of such vehicles are water, saline, Ringer's solution, dextrose solution, and 5% human serum albumin. Liposomes may also be used. The vehicle may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as either a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The pharmaceutical compositions of the present invention may be administered by any means that enables the conjugated composition to reach the targeted cells. In some embodiments, routes of administration include those selected from the group consisting of intravenous, intraarterial, intraperitoneal, local administration into the blood supply of the organ in which the tumor resides or directly into the tumor itself. Intravenous administration is the preferred mode of administration. It may be accomplished with the aid of an infusion pump.

The dosage administered varies depending upon factors such as: the nature of the active moiety; the nature of the conjugated composition; pharmacodynamic characteristics; its mode and route of administration; age, health, and weight of the recipient; nature and extent of symptoms; kind of concurrent treatment; and frequency of treatment.

Because conjugated compounds are specifically targeted to cells with one or more CRCA-1 translation products, conjugated compounds which comprise chemotherapeutics or toxins are administered in doses less than those which are used when the chemotherapeutics or toxins are administered as unconjugated active agents, preferably in doses that contain up to 100 times less active agent. In some embodiments, conjugated compounds which comprise chemotherapeutics or toxins are administered in doses that contain 10–100 times less active agent as an active moiety than the dosage of chemotherapeutics or toxins administered as unconjugated active agents. To determine the appropriate dose, the amount of compound is preferably measured in moles instead of by weight. In that way, the variable weight of different CRCA-1 translation product binding moieties does not affect the calculation. Presuming a one to one ratio of CRCA-1 translation product binding moiety to active moiety in conjugated compositions of the invention, less moles of conjugated compounds may be administered as compared to the moles of unconjugated compounds administered, preferably up to 100 times less moles.

Typically, chemotherapeutic conjugates are administered intravenously in multiple divided doses.

Up to 20 gm IV/dose of methotrexate is typically administered in an unconjugated form. When methotrexate is administered as the active moiety in a conjugated compound of the invention, there is a 10-to 100-fold dose reduction. Thus, presuming each conjugated compound includes one molecule of methotrexate conjugated to one CRCA-1 translation product binding moiety, of the total amount of conjugated compound administered, up to about 0.2–2.0 g of methotrexate is present and therefore administered. In some embodiments, of the total amount of conjugated compound administered, up to about 200 mg—2g of methotrexate is present and therefore administered.

To dose conjugated compositions comprising CRCA-1 translation product binding moieties linked to active moieties that are radioisotopes in pharmaceutical compositions useful as imaging agents, it is presumed that each CRCA-1 translation product binding moiety is linked to one radioactive active moiety. The amount of radioisotope to be administered is dependent upon the radioisotope. Those having ordinary skill in the art can readily formulate the amount of conjugated compound to be administered based upon the specific activity and energy of a given radionuclide used as an active moiety. Typically 0.1–100 millicuries per dose of imaging agent, preferably 1–10 millicuries, most often 2–5 millicuries are administered. Thus, pharmaceutical compositions according to the present invention useful as imaging agents which comprise conjugated compositions comprising a CRCA-1 translation product binding moiety and a radioactive moiety comprise 0.1–100 millicuries, in some embodiments preferably 1–10 millicuries, in some embodiments preferably 2–5 millicuries, in some embodiments more preferably 1–5 millicuries. Examples of dosages include: $^{131}I$=between about 0.1–100 millicuries per dose, in some embodiments preferably 1–10 millicuries, in some embodiments 2–5 millicuries, and in some embodiments about 4 millicuries; $^{111}$In=between about 0.1–100 millicuries per dose, in some embodiments preferably 1–10 millicuries, in some embodiments 1–5 millicuries, and in some embodiments about 2 millicuries; $^{99}$Tc=between about 0.1–100 millicuries per dose, in some embodiments preferably 5–75 millicuries, in some embodiments 10–50 millicuries, and in some embodiments about 27 millicuries. Wessels B. W. and R. D. Rogus (1984) *Med. Phys.* 11:638 and Kwok, C. S. et al. (1985) *Med. Phys.* 12:405, both of which are incorporated herein by reference, disclose detailed dose calculations for diagnostic and therapeutic conjugates which may be used in the preparation of pharmaceutical compositions of the present invention which include radioactive conjugated compounds.

One aspect of the present invention relates to a method of treating individuals suspected of suffering from metastasized colorectal cancer. Such individuals may be treated by administering to the individual a pharmaceutical composition that comprises a pharmaceutically acceptable carrier or diluent and a conjugated compound that comprises a CRCA-1 translation product binding moiety and an active moiety wherein the active moiety is a radiostable therapeutic agent. In some embodiments of the present invention, the pharmaceutical composition comprises a pharmaceutically acceptable carrier or diluent and a conjugated compound that comprises a CRCA-1 translation product binding moiety and an active moiety wherein the active moiety is a radiostable active agent and the CRCA-1 translation product binding moiety is an antibody. In some embodiments of the present invention, the pharmaceutical composition comprises a pharmaceutically acceptable carrier or diluent and a conjugated compound that comprises a CRCA-1 translation product binding moiety and an active moiety wherein the active moiety is a radiostable therapeutic agent. In some embodiments of the present invention, the pharmaceutical composition comprises a pharmaceutically acceptable carrier or diluent and a conjugated compound that comprises a CRCA-1 translation product binding moiety and an active moiety wherein the active moiety is a radiostable active agent selected from the group consisting of: methotrexate, doxorubicin, daunorubicin, cytosinarabinoside, etoposide, 5-4 fluorouracil, melphalan, chlorambucil, cis-platinum, vindesine, mitomycin, bleomycin, purothionin, macromomycin, 1,4-benzoquinone derivatives, trenimon, ricin, ricin A chain, Pseudomonas exotoxin, diphtheria toxin, *Clostridium perfringens* phospholipase C, bovine pancreatic ribonuclease, pokeweed antiviral protein, abrin, abrin A chain, cobra venom factor, gelonin, saporin, modeccin, viscumin, volkensin, alkaline phosphatase, nitroimidazole, metronidazole and misonidazole. The individual being treated may be diagnosed as having metastasized colorectal cancer or may be diagnosed as having localized colorectal cancer and may undergo the treatment proactively in the event that there is some metastasis as yet undetected. The pharmaceutical composition contains a therapeutically effective amount of the conjugated composition. A therapeutically effective amount is an amount which is effective to cause a cytotoxic or cytostatic effect on metastasized colorectal cancer cells without causing lethal side effects on the individual.

One aspect of the present invention relates to a method of treating individuals suspected of suffering from metastasized colorectal cancer. Such individuals may be treated by administering to the individual a pharmaceutical composition that comprises a pharmaceutically acceptable carrier or diluent and a conjugated compound that comprises a CRCA-1 translation product binding moiety and an active moiety wherein the active moiety is a radioactive. In some embodiments of the present invention, the pharmaceutical composition comprises a pharmaceutically acceptable carrier or diluent and a conjugated compound that comprises a CRCA-1 translation product binding moiety and an active moiety wherein the active moiety is a radioactive and the ST receptor binding moiety is an antibody. In some embodiments of the present invention, the pharmaceutical composition comprises a pharmaceutically acceptable carrier or diluent and a conjugated compound that comprises a CRCA-1 translation product and an active moiety wherein the active moiety is a radioactive agent selected from the group consisting of: $^{47}$Sc, $^{67}$Cu, 90Y, $^{109}$Pd, 123I, 125I, 131I, $^{186}$Re, $^{188}$Re, $^{199}$Au, $^{211}$At, $^{212}$Pb, $^{212}$B, $^{32}$P and 33P, $^{71}$Ge, $^{77}$As, $^{103}$Pb, $^{105}$Rh, $^{111}$Ag, $^{119}$Sb, $^{121}$Sn, $^{131}$Cs, 143 Pr, $^{1631}$Tb, $^{177}$Lu, $^{191}$Os. $^{193M}$Pt, $^{197}$Hg, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt, $^{197}$Hg, all beta negative and/or auger emitters. The individual being treated may be diagnosed as having metastasized colorectal cancer or may be diagnosed as having localized colorectal cancer and may undergo the treatment proactively in the event that there is some metastasis as yet undetected. The pharmaceutical composition contains a therapeutically effective amount of the conjugated composition. A therapeutically effective amount is an amount which is effective to cause a cytotoxic or cytostatic effect on metastasized colorectal cancer cells without causing lethal side effects on the individual.

One aspect of the present invention relates to a method of detecting metastasized colorectal cancer cells in an individual suspected of suffering from metastasized colorectal cancer by radioimaging. Such individuals may be diagnosed as suffering from metastasized colorectal cancer and the metastasized colorectal cancer cells may be detected by administering to the individual, preferably by intravenous administration, a pharmaceutical composition that comprises a pharmaceutically acceptable carrier or diluent and a conjugated compound that comprises a CRCA-1 translation product binding moiety and an active moiety wherein the active moiety is a radioactive and detecting the presence of a localized accumulation or aggregation of radioactivity, indicating the presence of cells with a CRCA-1 translation product. In some embodiments of the present invention, the pharmaceutical composition comprises a pharmaceutically acceptable carrier or diluent and a conjugated compound that comprises a CRCA-1 translation product binding moiety and an active moiety wherein the active moiety is a radioactive and the ST receptor binding moiety is an antibody. In some embodiments of the present invention, the pharmaceutical composition comprises a pharmaceutically acceptable carrier or diluent and a conjugated compound that comprises an ST receptor binding moiety and an active moiety wherein the active moiety is a radioactive agent selected from the group consisting of: radioactive heavy metals such as iron chelates, radioactive chelates of gadolinium or manganese, positron emitters of oxygen, nitrogen, iron, carbon, or gallium, $^{43}$K $^{52}$Fe $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{113M}$In, $^{123}$I, $^{125}$I, $^{127}$Cs, $^{129}$Cs, 131I, $^{132}$I, $^{197}$Hg, $^{203}$Pb and $^{206}$Bi. The individual being treated may be diagnosed as having metastasized colorectal cancer or may be diagnosed as having localized colorectal cancer and may undergo the treatment roactively in the event that there is some metastasis as yet undetected. The pharmaceutical composition contains a diagnostically effective amount of the conjugated composition. diagnostically effective amount is an amount which can be detected at a site in the body where cells with ST receptors are located without causing lethal side effects on the individual.

Another aspect of the invention relates to unconjugated compositions which comprise a CRCA-1 translation product binding ligand and an active agent. For example, liposomes are small vesicles composed of lipids. Drugs can be introduced into the center of these vesicles. The outer shell of these vesicles comprise a CRCA-1 translation product binding ligand. Liposomes Volumes 1, 2 and 3 CRC Press Inc. Boca Raton Fla., which is incorporated herein by reference, disclose preparation of liposome-encapsulated active agents which include targeting agents that correspond to CRCA-1 translation product ligand in the outer shell. Unconjugated compositions which comprise a CRCA-1 translation product ligand in the matrix of a liposome with an active agent inside include such compositions in which the CRCA-1 translation product ligand is san antibody and the active agent is selected from the group consisting of: methotrexate, doxorubicin, daunorubicin, cytosinarabinoside, etoposide, 5-4 fluorouracil, melphalan, chlorambucil, cis-platinum, vindesine, mitomycin, bleomycin, purothionin, macromomycin, 1,4-benzoquinone derivatives, trenimon, ricin, ricin A chain, Pseudomonas exotoxin, diphtheria toxin, *Clostridium perfringens* phospholipase C, bovine pancreatic ribonuclease, pokeweed antiviral protein, abrin, abrin A chain, cobra venom factor, gelonin, saporin, modeccin, viscumin, volkensin, alkaline phosphatase, nitroimidazole, metronidazole and misonidazole.

Drug Delivery Targeted To Colon Cells Generally

Another aspect of the invention relates to unconjugated and conjugated compositions which comprise a CRCA-1 translation product ligand used to deliver therapeutic nucleic acid molecules to cells that comprise a CRCA-1 translation product such as normal and cancer cells of the intestinal tract as well as metastasized colorectal cancer cells. In some embodiments, the genetic material is delivered to metastasized tumor cells to produce an antigen that can be targeted by the immune system or to produce a protein which kills the cell or inhibits its proliferation. In some embodiments, the CRCA-1 translation product ligand is used to deliver nucleic acids that encode nucleic acid molecules which replace defective endogenous genes or which encode therapeutic proteins. In some embodiments, the CRCA-1 translation product ligand is thus used to deliver the active agent specifically to the cells lining the intestinal tract to treat diseases specific to this organ. According to this aspect of the invention, compositions comprise nucleic acid molecules which can replace defective genes. In some embodiments, the compositions are used in gene therapy protocols to deliver to individuals, genetic material needed and/or desired to make up for a genetic deficiency.

In some embodiments, the CRCA-1 translation product ligand is combined with or incorporated into a delivery vehicle thereby converting the delivery vehicle into a specifically targeted delivery vehicle. For example, a CRCA-1 translation product binding peptide may be integrated into the outer portion of a viral particle making such a virus a CRCA-1 translation product-bearing cell specific virus. Similarly, the coat protein of a virus may be engineered such that it is produced as a fusion protein which includes an active CRCA-1 translation product binding peptide that is exposed or otherwise accessible on the outside of the viral particle making such a virus a CRCA-1 translation product-bearing cell-specific virus. In some embodiments, a CRCA-1 translation product ligand may be integrated or otherwise incorporated into the liposomes wherein the CRCA-1 translation product ligand is exposed or otherwise accessible on the outside of the liposome making such liposomes specifically targeted to CRCA-1 translation product-bearing cells.

The active agent in the conjugated or unconjugated compositions according to this aspect of the invention is a nucleic acid molecule. The nucleic acid may be RNA or preferably DNA. In some embodiments, the nucleic acid molecule is an antisense molecule or encodes an antisense sequence whose presence in the cell inhibits production of an undesirable protein. In some embodiments, the nucleic acid molecule encodes a ribozyme whose presence in the cell inhibits production of an undesirable protein. In some embodiments, the nucleic acid molecule encodes a protein or peptide that is desirably produced in the cell. In some embodiments, the nucleic acid molecule encodes a functional copy of a gene that is defective in the targeted cell. The nucleic acid molecule is preferably operably linked to regulatory elements needed to express the coding sequence in the cell.

Liposomes are small vesicles composed of lipids. Genetic constructs which encode proteins that are desired to be expressed in CRCA-1 translation product-bearing cells are introduced into the center of these vesicles. The outer shell of these vesicles comprise an a CRCA-1 translation product ligand. Liposomes Volumes 1, 2 and 3 CRC Press Inc. Boca Raton Fla., which is incorporated herein by reference, disclose preparation of liposome-encapsulated active agents which include antibodies in the outer shell. In the present invention, a CRCA-1 translation product ligand such as for example an anti-CRCA-1 translation product antibodies is associated with the in the outer shell. Unconjugated compositions which comprise a CRCA-1 translation product ligand in the matrix of a liposome with an active agent inside include such compositions in which the CRCA-1 translation product ligand is preferably an antibody.

In one embodiment for example, cystic fibrosis, a genetic disease in which there is a mutation of a specific gene encoding a chloride transport protein which ultimately produces abnormalities of function in many systems, most notably in the respiratory and intestinal tract, is treated by gene therapy techniques using CRCA-1 translation product ligands to deliver the corrective gene to cells. Current therapy has been directed at replacing the mutant gene in the respiratory system with the normal gene by targeting these genes directly to the cells lining the respiratory tract using viruses which bind only to those cells. Similarly, the normal gene is packaged in liposomes targeted on their surface with CRCA-1 translation product ligands and delivered to the intestinal tract. CRCA-1 translation product ligands specifically target and direct the liposomes containing the normal gene to correct the lesion for cystic fibrosis to the specific cells lining the intestinal tract, from the duodenum to the rectum. Uptake of that genetic is material by those cells should result in a cure of cystic fibrosis in the intestinal tract.

In another embodiment, the delivery of normal copies of the p53 tumor suppressor gene to the intestinal tract is accomplished using CRCA-1 translation product ligand to target the gene therapeutic. Mutations of the p53 tumor suppressor gene appears to play a prominent role in the development of colorectal cancer in the intestinal tract. One approach to combatting this disease is the delivery of normal copies of this gene to the intestinal tract to cells expressing mutant forms of this gene. Genetic constructs that comprise normal p53 tumor suppressor genes are incorporated into liposomes that comprise a CRCA-1 translation product ligand. The composition is delivered to the intestinal tract.

CRCA-1 translation product binding ligands specifically target and direct the liposomes containing the normal gene to correct the lesion created by mutation of p53 suppressor gene in intestinal cells.

Preparation of genetic constructs is with the skill of those having ordinary skill in the art. The present invention allows such construct to be specifically targeted by using the CRCA-1 translation product ligands of the present invention. The compositions of the invention include a CRCA-1 translation product ligand such as an anti-CRCA-1 translation product antibody associated with a delivery vehicle and a gene construct which comprises a coding sequence for a protein whose production is desired in the cells of the intestinal tract linked to necessary regulatory sequences for expression in the cells. For uptake by cells of the intestinal tract, the compositions are administered orally or by enema whereby they enter the intestinal tract and contact cells which comprise one or more CRCA-1 translation products. The delivery vehicles associate with the CRCA-1 translation product by virtue of the CRCA-1 translation product ligand and the vehicle is internalized into the cell or the active agent/genetic construct is otherwise taken up by the cell. Once internalized, the construct can provide a therapeutic effect on the individual. One having ordinary skill in the art can readily formulate such compositions for oral or enema administration and determine the effective amount of such composition to be administered to treat the disease or disorder.

Antisense

The present invention procvides compositions, kits and methods which are useful to prevent and treat diseases effecting colon cells by providing the means to specifically deliver antisense compounds to colon cells and thereby stop expression of genes in such colon cells in which undesirable gene expression is taking place without negatively effecting cells in which no such expression occurs.

The conjugated compositions of the present invention are useful for targeting cells that line the inner intestine wall including those cancer cells derived from such cells, including metastasized cancer cells as well as localized cancer and normal colon cells. The conjugated compositions will not bind to non-colorectal derived cells. Thus, the active moieties of conjugated compositions administered to an individual are delivered to cells which are derived from the intestinal tract such as local normal and cancerous colorectal cells and metastasized colorectal cells. Non-colorectal cells, lacking one or more CRCA-1 translation products, do not take up the conjugated compositions. Thus, the present invention provides compositions and methods of delivering antisense compositions to colon cells only.

The present invention provides a colorectal cancer specific approach in which only colorectal cells are exposed to the active portion of the compound and only colorectal cancer cells are effected by the conjugated compound. The ST receptor binding moiety specifically binds to colorectal cells, including normal colorectal cells, localized colorectal cancer cells and metastasized colorectal cancer cells. Upon binding to these cells, the conjugated compound is internalized and the delivery of the conjugated compound including the antisense portion of the molecule is effected. The presence of the conjugated compound in normal colorectal cells has no effect on such cells because the colorectal cancer-associated gene for which the antisense molecule that makes up the active moiety of the conjugated compound is complementary is not being expressed. However, in colorectal cancer cells, the cancer gene for which the antisense molecule that makes up the active moiety of the conjugated compound is complementary is being expressed. The presence of the conjugated compound in colorectal cancer cells serves to inhibit or prevent transcription or translation of the cancer gene and thereby reduce or eliminate the transformed phenotype.

The invention can be used to combat localized or metastasized colorectal cancer as well as to prevent the emergence of the transformed phenotype. Thus the invention can be used therapeutically as well as prophylactically.

Therapeutic and prophylactic pharmaceutical compositions of the present invention include conjugated compounds specifically targeted to colon cells. These conjugated compounds include CRCA-1 translation products binding moieties which do not bind to cells of normal tissue in the body except cells of the intestinal tract since the cells of other tissues do not possess ST receptors. Thus, only normal colorectal cells, localized colorectal cancer cells and metastasized colorectal cancer cells take up the conjugated compositions.

One having ordinary skill in the art can readily identify individuals suspected of suffering from colorectal cancer and metastasized colorectal cells. In those individuals diagnosed with colorectal cancer, it is standard therapy to suspect metastasis and aggressively attempt to eradicate metastasized cells. The present invention provides pharmaceutical compositions and methods for specifically targeting and eliminating metastasized colorectal cancer cells. Further, the present invention provides pharmaceutical. compositions that comprise therapeutics and methods for specifically eliminating colorectal cancer cells. The present invention provides pharmaceutical compositions and methods for specifically in colorectal cells and preventing transformation by such cells by prophylactically furnishing such cells with antisense molecules that inhibit transcription or translation of genes involved in transformation.

The pharmaceutical compositions which comprise conjugated compositions of the present invention may be used to diagnose or treat individuals suffering from localized and/or metastatic colorectal tumors, that is primary or non-metastatic colorectal tumors as well as metastasized colorectal tumors.

The present invention relies upon the use of a CRCA-1 translation product binding moiety in a conjugated composition. The CRCA-1 translation product binding moiety is essentially a portion of the conjugated composition which acts as a ligand to the CRCA-1 translation product and thus specifically binds to these receptors. The conjugated composition also includes an active moiety which is associated with the CRCA-1 translation product binding moiety; the active moiety being an antisense composition useful to inhibit or prevent transcription or translation of expression of genes whose expression is associated with cancer.

According to the present invention, the active moiety is an antisense composition. In particular, the antisense molecule that makes up the active moiety of a conjugated compound hybridizes to DNA or RNA in a colon cell and inhibits and/or prevents transcription or translation of the DNA or RNA from taking place. The antisense compositions may be a nucleic acid molecule, a derivative or an analogs thereof. The chemical nature of the antisense composition may be that of a nucleic acid molecule or a modified nucleic acid molecule or a non-nucleic acid molecule which possess functional groups that mimic a DNA or RNA molecule that is complementary to the DNA or RNA molecule whose expression is to be inhibited or otherwise prevented. Antisense compositions inhibit or prevent transcription or translation of genes whose expression is linked to colorectal cancer, i.e. colorectal cancer associated genes. Examples of such genes include, but are not limited to: hereditary non-polyposis coli (HNPCC) genes such as hMSH2, hMLH1, hPMS1, and hPMS2, Ras, adenomatous polyposis coli (APC), ERBB-1/HER-1, ERBB-2/HER-2, p53 Tumor Suppressor, MYB, FOS, ABL, MYC, Protein Tyrosine Phosphatase G1, Cyclic AMP-Dependent Protein Kinase (PKA), CRIPTO, Transforming Growth Factor Alpha and 1p.

Colorectal cancer-associated genes provide the genetic basis for colorectal cancer. Colorectal cancer is a process involving accumulation of genetic mutations in epithelial cells leading to the neoplastic phenotype associated with unregulated growth. Colorectal carcinogenesis is a multi-stage process involving the progression from adenomas to invasive carcinomas. Indeed, the cumulative total of genetic abnormalities appear to be more important than their order of appearance. Many of the genetic abnormalities result from allelic loss or deletion of fragments of chromosomes. Specific genetic abnormalities which have been associated with the colorectal cancer phenotype will be discussed below. These all are potential s for treatment employing genetic approaches. See: Toribara, N W and Sleisenger, M H (1995) Screening for colorectal cancer. New *Eng. J. Med.* 332:861–867 which is hereby incorporated herein by reference including all references cited therein which are also hereby incorporated herein by reference.

HNPCC refers to 4 genes that are suspected to be responsible for hereditary nonpolyposis coli (HNPCC) colorectal cancer. These four genes have been identified and are discussed in Toribara, N W and Sleisenger, M H (1995) Screening for colorectal cancer. *New Eng. J. Med.* 332:861–867. The genes, called hMSH2, hMLH1, hPMS1, and hPMS2, are proofreading genes that repair mismatches of bases in DNA. Loss of this function allows replication errors to occur in the DNA.

Point mutations insertions, and deletions in K-ras and H-ras have been identified in colorectal tumors. See: Toribara, N W and Sleisenger, M H (1995) Screening for colorectal cancer. *New Eng. J. Med.* 332:861–867; Kniazev, PG, et al. Complex characteristics of the alterations of oncogenes HER-2/ERBB-2, HER-1/ERBB-1, HRAS-1, C-MYC and anti-oncogenes p53, RB1, as well as deletions of loci of chromosome 17 in colon carcinoma. *Molekuliarnaia Biologiia.* 26(5) :1134–47, September–October 1992, and Ramsay, R G, et al. Myb expression is higher in malignant human colonic carcinoma and premalignant adenomatous polyps than in normal mucosa. *Cell Growth & Differentiation.* 3(10):723–30, 1992 Oct., which are each hereby incorporated herein by reference including all references cited therein which are also hereby incorporated herein by reference.

Patients with familial adenomatous polyposis coli (APC) appear to have a series of deletions including deletions of chromosome 5q, 18q, 17p. The 17p deletion represents a deletion of the p53 suppressor gene.

ERBB-1/HER-1 and ERBB-2/HER-2 genes have been demonstrated to be amplified in about 4–8% of cases of colorectal cancer.

Point mutations in p53 genes have been reported to be mutated in about 3% of colorectal cancer cases.

MYB proto-oncogene expression has been demonstrated to be higher in colorectal tumors. See: Ramsay, R G, Thompson, M A, Hayman, J A, Reid, G, Gonda, T J, Whitehead, R H. Myb expression is higher in malignant human colonic carcinoma and premalignant adenomatous polyps than in normal mucosa. Cell Growth & Differentia-tion. 3(10):723–30, October 1992; Melani, C. et al. Inhibition of proliferation by c-myb antisense oligodeoxynucle-otides in colon adenocarcinoma cell lines that express c-myb. Cancer Research 51(11) :2897–901, Jun. 1, 1992;

and Ramsay RG, et al. Myb expression is higher in malignant human colonic carcinoma and premalignant adenomatous polyps than in normal mucosa. Cell Growth & Differentiation. 3(10):723–30, October 1992; which are each hereby incorporated herein by reference including all references cited therein which are also hereby incorporated herein by reference. Indeed, tumors and cells with the highest levels of expression of MYB were the most dysplastic and had the highest levels of proliferation. cMYB is a protooncogene which plays a role in the proliferation signaling pathway. Rearrangements, insertions, and deletions of this gene have been observed. See: Alexander, R J, et al. Oncogene alterations in rat colon tumors induced by N-methyl-N-nitrosourea. *American Journal of the Medical Sciences.* 303(1):16–24, January 1992, which is hereby incorporated herein by reference including all references cited therein which are also hereby incorporated herein by reference. Antisense MYB oligonucleotides retard the proliferation of colonic adenocarcinoma cells which had the highest level of expression of this oncogene, in vitro.

Chemical carcinogenesis in a rat model demonstrated point mutations in fos, an oncogene which mediates transcriptional regulation and proliferation. See: Alexander, R J, et al. Oncogene alterations in rat colon tumors induced by N-methyl-N-nitrosourea. *American Journal of the Medical Sciences.* 303(1):16–24, January 1992, which is hereby incorporated herein by reference including all references cited therein which are also hereby incorporated herein by reference.

Chemical carcinogenesis in a rat model demonstrated point mutations in the oncogene abl. See: Alexander, R J, et al. Oncogene alterations in rat colon tumors induced by N-methyl-N-nitrosourea. *American Journal of the Medical Sciences.* 303(1):16–24, January 1992.

MYC is an oncogene that plays a role in regulating transcription and proliferation. Increased expression of MYC has been found in colorectal cancer cells. Collins, J F, et al. c-myc antisense oligonucleotides inhibit the colony-forming capacity of Colo 320 colonic carcinoma cells. Journal of Clinical Investigation. 89(5):1523–7, May 1992; and Rodriguez-Alfageme, C, et al. Suppression of deregulated c-MYC expression in human colon carcinoma cells by chromosome 5 transfer. *Proceedings of the National Academy of Sciences of the United States of America.* 89(4) : 1482–6, Feb. 15, 1992. which are both hereby incorporated herein by reference including all references cited therein which are also hereby incorporated herein by reference. A 15-base antisense oligonucleotide to myc complementary to the translation initiation region of exon II was incubated with colorectal cancer cells. This antisense molecule inhibited proliferation of colorectal cancer cells in a dos-dependent fashion. Interestingly, the uptake of this oligonucleotide was low (0.7%). Also, transfer of a normal chromosome 5 to colorectal cancer cells resulted in the regulation of myc expression and loss of proliferation. These data suggest that a tumor suppressor gene important in the regulation of myc is contained on this chromosome.

A novel protein tyrosine phosphatase, G1, has been identified. Examination of the mRNA encoding this protein in colorectal tumor cells revealed that it undergoes point mutations and deletions in these cells and may play a role in proliferation characteristic of these cells. Takekawa, M. et al. Chromosomal localization of the protein tyrosine phosphatase G1 gene and characterization of the aberrant transcripts in human colon cancer cells. *FEBS Letters.* 339(3) :222–8, Feb. 21, 1994, which is hereby incorporated herein by reference including all references cited therein which are also hereby incorporated herein by reference.

Gastrin regulates colon cancer cell growth through a cyclic AMP-dependent mechanism mediated by PKA. Antisense oligodeoxynucleotides to the regulatory subunit of a specific class of PKA inhibited the growth-promoting effects of cyclic AMP in colon carcinoma cells. See: Bold, R J, et al. Experimental gene therapy of human colon cancer. *Surgery.* 116(2):189–95; discussion 195–6, August 1994 and Yokozaki, H., et al. An antisense oligodeoxynucleotide that depletes RI alpha subunit of cyclic AMP-dependent protein kinase induces growth inhibition in human cancer cells. *Cancer Research.* 53(4):868–72, Feb 15, 1993, which are both hereby incorporated herein by reference including all references cited therein which are also hereby incorporated herein by reference.

CRIPTO is an epidermal growth factor-related gene expressed in a majority of colorectal cancer tumors. Antisense phosphorothioate oligodeoxynucleotides to the 5'-end of CRIPTO mRNA significantly reduced CRIPTO expression and inhibited colorectal tumor cell growth in vitro and in vivo. Ciardiello, F. et al. Inhibition of CRIPTO expression and tumorigenicity in human colon cancer cells by antisense RNA and oligodeoxynucleotides. *Oncogene.* 9(1) :291–8, January 1994 which are both hereby incorporated herein by reference including all references cited therein which are also hereby incorporated herein by reference.

Many carcinoma cells secrete transforming growth factor alpha. A 23 nucleotide antisense oligonucleotide to TGF alpha mRNA inhibited both DNA synthesis an proliferation of colorectal cancer cells. Sizeland, AM, Burgess, AW. Antisense transforming growth factor alpha oligonucleotides inhibit autocrine stimulated proliferation of a colon carcinoma cell line. *Molecular Biology of the Cell.* 3(11) :1235–43, November 1992 which is hereby incorporated herein by reference including all references cited therein which are also hereby incorporated herein by reference.

Human colorectal tumors have been identified with deletions of chromosome 1p. It appears that a portion of this chromosome, 1p36–34, contains a tumor suppressor gene that regulates the expression of MYC. Tanaka, K, et al. Suppression of tumorigenicity in human colon carcinoma cells by introduction of normal chromosome 1p36 region. *Oncogene.* 8(8):2253–8, August 1993, which is hereby incorporated herein by reference including all references cited therein which are also hereby incorporated herein by reference.

Antisense compositions including oligonucleotides, derivatives and analogs thereof, conjugation protocols, and antisense strategies for inhibition of transcription and translation are generally described in: *Antisense Research and Applications*, Crooke, S. and B. Lebleu, eds. CRC Press, Inc. Boca Raton Fla. 1993; *Nucleic Acids in Chemistry and Biology* Blackburn, G. and M. J. Gait, eds. IRL Press at Oxford University Press, Inc. New York 1990; and *Oligonucleotides and Analogues: A Practical Approach Eckstein*, F. ed., IRL Press at Oxford University Press, Inc. New Yoprk 1991; which are each hereby incorporated herein by reference including all references cited therein which are hereby incorporated herein by reference.

The antisense molecules of the present invention comprise a sequence complementary to a fragment of a colorectal cancer gene. See Ullrich et al., *EMBO J.,* 1986, 5:2503, which is hereby incorporated herein by reference. Contemplated by this definition are fragments of oligos within the coding sequence of colorectal cancer genes. Antisense compositions which can make up an active moiety in conjugated compounds of the invention include oligonucleotides formed of homopyrimidines can recognize local stretches of homopurines in the DNA double helix and bind to them in the major groove to form a triple helix. See: Helen, C and Toulme, J J. Specific regulation of gene expression by antisense, sense, and antigene nucleic acids. *Biochem. Biophys Acta,* 1049:99–125, 1990 which is hereby incorporated herein by reference including all references cited therein which are hereby incorporated herein by reference. Formation of the triple helix would interrupt the ability of the specific gene to undergo transcription by RNA polymerase. Triple helix formation using myc-specific oligonucleotides has been observed. See: Cooney, M, et al. *Science* 241:456–459 which is hereby incorporated herein by reference including all references cited therein which are hereby incorporated herein by reference.

Antisense oligonucleotides of DNA or RNA complementary to sequences at the boundary between introns and exons can be employed to prevent the maturation of newly-generated nuclear RNA transcripts of specific genes into mRNA for transcription. Antisense RNA complimentary to specific genes can hybridize with the mRNA for tat gene and prevent its translation. Antisense RNA can be provided to the cell as "ready-to-use" RNA synthesized in vitro or as an antisense gene stably transfected into cells which will yield antisense RNA upon transcription. Hybridization with mRNA results in degradation of the hybridized molecule by RNAse H and/or inhibition of the formation of translation complexes. Both result in a failure to produce the product of the original gene.

Antisense sequences of DNA or RNA can be delivered to cells. Several chemical modifications have been developed to prolong the stability and improve the function of these molecules without interfering in their ability to recognize specific sequences. These include increasing their resistance to degradation by DNases, including phosphotriesters, methylphosphonates, phosphorothioates, alpha-anomers, increasing their affinity for their s by covalent linkage to various intercalating agents such as psoralens, and increasing uptake by cells by conjugation to various groups including polylysine. These molecules recognize specific sequences encoded in mRNA and their hybridization prevents translation of and increases the degradation of these messages.

Conjugated compositions of the invention provide a specific and effective means for terminating the expression of genes which cause neoplastic transformation. CRCA-1 translation products undergo ligand-induced endocytosis and can deliver conjugated compounds to the cytoplasm of cells when the CRCA-1 translation product binding moiety binds to an ST receptor on a colon cell. The unique localization of these receptors and their ability to undergo endocytosis make them excellent candidates for targeting therapeutics to these tumors.

CRCA-1 translation product binding moieties are conjugated directly to antisense compositions such as nucleic acids which are active in inducing a response in colorectal tumor cells. For example, antisense oligonucleotides to MYC are conjugated directly to an anti-CRCA-1 translation product antibody. This has been performed employing peptides that bind to the CD4 receptor. See: Cohen, JS, ed. *Oligodeoxynucleotides: Antisense Inhibitors of Gene Expression. Topics in Molecular and Structural Biology.* CRC Press, Inc., Boca Raton, 1989. which is hereby incorporated herein by reference including all references cited therein which are hereby incorporated herein by reference. The precise backbone and its synthesis is not specified and can be selected from well-established techniques. Synthesis would involve either chemical conjugation or direct synthesis of the chimeric molecule by solid phase synthesis employing FMOC chemistry. See: Haralambidis, J, et al. (1987) *Tetrahedron Lett.* 28:5199–5202, which is hereby incorporated herein by reference including all references cited therein which are hereby incorporated herein by reference. Alternatively, the peptide-nucleic acid conjugate may be synthesized directly by solid phase synthesis as a peptide-peptide nucleic acid chimera by solid phase synthesis. Nielsen, PE, et al. (1994) Sequence-specific transcription arrest by peptide nucleic acid bound to the DNA template strand. *Gene* 149:139–145, which is hereby incorporated herein by reference including all references cited therein which are hereby incorporated herein by reference.

In some embodiments, polylysine can be complexed to conjugated compositions of the invention in a non-covalent fashion to nucleic acids and used to enhance delivery of these molecules to the cytoplasm of cells. In addition, peptides and proteins can be conjugated to polylysine in a covalent fashion and this conjugate complexed with nucleic acids in a non-covalent fashion to further enhance the specificity and efficiency of uptake of the nucleic acids into cells. Thus, CRCA-1 translation product ligand is conjugated chemically to polylysine by established techniques. The polylysine-CRCA-1 translation product ligand conjugate may be complexed with nucleic acids of choice. Thus, polylysine-orosomucoid conjugates were employed to specifically plasmids containing genes to be expressed to hepatoma cells expressing the orosomucoid receptor. This approach can be used to delivery whole genes, or oligonucleotides. Thus, it has the potential to terminate the expression of an undesired gene (eg. MYC, ras) or replace the function of a lost or deleted gene (eg. hMSH2, hMLH1, hPMS1, and hPMS2).

According to a preferred embodiment, Myc serves as a gene whose expression is inhibited by an antisense molecule within a conjugated composition. Many, if not most, colorectal tumor cells overexpress MYC, a gene involved in mediating proliferation. Decreasing the proliferation of colorectal tumor cells is attained by employing antisense oligonucleotides complimentary to MYC to hybridize with the mRNA for this protein, resulting in the degradation of this message and a dramatic reduction in the production of MYC. CRCA-1 translation product binding moieties are used to deliver a 15-based antisense oligonucleotide to myc complementary to the translation initiation region of exon II. This construct was active in inhibiting the expression of MYC when it was incubated with colorectal cancer cells. The 15-base antisense oligonucleotide to MYC is synthesized as reported in Collins, J F, Herman, P, Schuch, C, Bagby G C, Jr. *Journal of Clinical Investigation.* 89(5): 1523–7, May 1992. In some embodiments, the conjugated composition is conjugated to polylysine as reported previously. Wu, GY, and Wu, CH. (1988) Evidence for ed gene delivery to Hep G2 hepatoma cells in vitro. *Biochem.* 27:887–892 which is incorporated herein by reference.

Conjugated compositions may be synthesized as a chimeric molecule directly by solid phase synthesis. pmolar to nanomolar concentrations for this conjugate suppress MYC synthesis in colorectal cancer cells in vitro.

Antisense molecules are preferably hybridize to, i.e. are complementary to, a nucleotide sequence that is 5–50 nucleotides in length, more preferably 5-25 nucleotides and in some embodiments 10–15 nucleotides.

In addition, mismatches within the sequences identified above, which achieve the methods of the invention, such that the mismatched sequences are substantially complementary to the colorectal cancer gene sequences are also considered within the scope of the disclosure. Mismatches which permit substantial complementarity to the colorectal cancer gene sequences will be known to those of skill in the art once armed with the present disclosure. The oligos may also be unmodified or modified.

Therapeutic compositions and methods may be used to combat colorectal cancer in cases where the cancer is localized and/or metastasized. Individuals are administered a therapeutically effective amount of conjugated compound. A therapeutically effective amount is an amount which is effective to cause a cytotoxic or cytostatic effect on metastasized colorectal cancer cells without causing lethal side effects on the individual. An individual who has been administered a therapeutically effective amount of a conjugated composition has a increased chance of eliminating colon cancer as compared to the risk had the individual not received the therapeutically effective amount.

To treat localized colorectal cancer, a therapeutically effective amount of a conjugated compound is administered such that it will come into contact with the localized tumor within the colon. Thus, the conjugated compound is administered orally or rectally. In cases where conjugated compounds are orally administered, they are preferably enteric coated or otherwise formulated to avoid degradation by stomach acids. Enteric formulations are described in U.S. Pat. No. 4,601,896, U.S. Pat. No. 4,729,893, U.S. Pat. No. 4,849,227, U.S. Pat. No. 5,271,961, U.S. Pat. No. 5,350,741, and U.S. Pat. No. 5,399,347, which are each hereby incorporated herein by reference. Oral and rectal formulation are taught in Remington's Pharmaceutical Sciences, 18th Edition, 1990, Mack Publishing Co., Easton Pa. which is incorporated herein by reference. Alternative embodiments include sustained release formulations and implant devices which provide continuous delivery of conjugated compositions to the colon.

The pharmaceutical compositions according to the present invention may be administered as either a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The present invention is directed to a method of delivering antisense compounds to colon cells and inhibiting expression of colorectal cancer genes in mammals. The methods comprise administering to a mammal an effective amount of a conjugated composition which comprises a CRCA-1 translation product binding moiety conjugated to an antisense oligonucleotide having a sequence which is complementary to a region of DNA or mRNA of a colorectal cancer gene.

The conjugated compounds may be administering to mammals in a mixture with a pharmaceutically-acceptable carrier, selected with regard to the intended route of administration and the standard pharmaceutical practice. Dosages will be set with regard to weight, and clinical condition of the patient. The conjugated compositions of the present invention will be administered for a time sufficient for the mammals to be free of undifferentiated cells and/or cells having an abnormal phenotype. In therapeutic methods treatment extends for a time sufficient to inhibit transformed cells from proliferating and conjugated compositions may be administered in conjunction with other chemotherapeutic agents to manage and combat the patient's cancer.

The conjugated compounds of the invention may be employed in the method of the invention singly or in combination with other compounds. The amount to be administered will also depend on such factors as the age, weight, and clinical condition of the patient. See Gennaro, Alfonso, ed., Remington's Pharmaceutical Sciences, 18th Edition, 1990, Mack Publishing Co., Easton Pa.

Prophylactic compositions and methods may be used to prevent the origin of colorectal cancer. In particular, conjugated compounds may be administered to an individual is suspected of being susceptible to colorectal cancer. Using genotyping techniques, the specific nature of an individuals susceptibility may be identified. That is, it may be possible to determine what cancer gene will be associated with colorectal cancer in an individual. For example, defects in the APC gene and kits for diagnosing the same are disclosed in U.S. Pat. No. 5,352,775 which is hereby incorporated herein by reference. Similarly, defects in the MCC gene and kits for diagnosing the same are disclosed in U.S. Pat. No. 5,330,892 which is hereby incorporated herein by reference. In prophylactic methods, treatment extends continuously or sporadically from time to time for a time sufficient to inhibit transformation.

To prevent colorectal cancer, a prophylactically effective amount of a conjugated compound is administered such that it will come into contact with and incorporated by normal colon cells. Thus, the conjugated compound is administered orally or rectally. In cases where conjugated compounds are orally administered, they are preferably enteric coated or otherwise formulated to avoid degradation by stomach acids as described above.

A prophylactically effective amount is an amount which is effective to prevent the initiation of transformation of colon cancer in cells. An individual who has been administered a prophylactically effective amount of a conjugated composition has a reduced risk of development of colon cancer as compared to the risk had the individual not received the prophylactically effective.

Therapeutic and Prophylactic Vaccines

The invention relates to prophylactic and therapeutic vaccines for protecting individuals against metastatic colorectal cancer and for treating individuals who are suffering from metastatic colorectal cancer.

According to the present invention, one or more of the CRCA-1 translation products serves as a target against which a protective and therapeutic immune response can be induced.

Specifically, vaccines are provided which induce an immune response against a CRCA-1 translation product. The vaccines of the invention include, but are not limited to, the following vaccine technologies:

1) DNA vaccines, i.e. vaccines in which DNA that encodes at least an epitope from a CRCA-1 translation product that is not present on ST receptor protein is administered to an individual's cells where the epitope is expressed and serves as a target for an immune response;

2) infectious vector mediated vaccines such as recombinant adenovirus, vaccinia, Salmonella, and BCG wherein the vector carries genetic information that encodes at least an epitope from a CRCA-1 translation product that is not present on ST receptor protein such that when the infectious vector is administered to an individual, the epitope is expressed and serves as a target for an immune response;

3) killed or inactivated vaccines which a) comprise either killed cells or inactivated viral particles that display at least an epitope from a CRCA-1 translation product that is not present on ST receptor protein and b) when administered to an individual serves as a target for an immune response;

3) haptenized killed or inactivated vaccines which a) comprise either killed cells or inactivated viral particles that display at least an epitope from a CRCA-1 translation product that is not present on ST receptor protein, b) are haptenized to be more immunogenic and c) when administered to an individual serves as a target for an immune response;

4) subunit vaccines which are vaccines that include protein molecules that include at least an epitope from a CRCA-1 translation product that is not present on ST receptor protein; and 5) haptenized subunit vaccines which are vaccines that a) include protein molecules that include at least an epitope from a CRCA-1 translation product that is not present on ST receptor protein and b) are haptenized to be more immunogenic.

The present invention relates to administering to an individual a protein or nucleic acid molecule that comprises or encodes, respectively, an immunogenic epitope against which an therapeutic and prophylactic immune response can be induced. Such epitopes are generally at least 6–8 amino acids in length. The vaccines of the invention therefore comprise proteins which are at least, or nucleic acids which encode at least, 6-8 amino acids in length from one or more CRCA-1 translation products that is not present on ST receptor protein. The vaccines of the invention may comprise proteins which are at least, or nucleic acids which encode at least 10 to about 1000 amino acids in length. The vaccines of the invention may comprise proteins which are at least, or nucleic acids which encode at least, about 25 to about 500 amino acids in length. The vaccines of the invention may comprise proteins which are at least, or nucleic acids which encode at least, about 50 to about 400 amino acids in length. The vaccines of the invention may comprise proteins which are at least, or nucleic acids which encode at least, about 100 to about 300 amino acids in length.

The present invention relates to compositions for and methods of treating individuals who are known to have metastasized colorectal cancer. Metastasized colorectal cancer may be diagnosed by those having ordinary skill in the art using art accepted clinical and laboratory pathology protocols and/or those described in U.S. Ser. No. 08/141,892 filed on Oct. 26, 1993, U.S. Ser. No. 08/305,056 filed on Sep. 13, 1994, and PCT Application Ser. No. PCT/US94/12232 filed Oct. 26, 1994. The present invention provides an immunotherapeutic vaccine useful to treat individuals who have been diagnosed as suffering from metastasized colorectal cancer. The immunotherapeutic vaccines of the present invention may be administered in combination with other therapies including, but not limited to those described in U.S. Ser. No 08/141,892 filed on Oct. 26, 1993, U.S. Ser. No. 08/305,056 filed on Sep. 13, 1994, and PCT Application Ser. No. PCT/US94/12232 filed Oct. 26, 1994.

The present invention relates to compositions for and methods of preventing metastatic colorectal cancer in individual is suspected of being susceptible to metastasized colorectal cancer. Such individuals include those whose family medical history indicates above average incidence of colorectal cancer among family members and/or those who have already developed colorectal cancer and have been effectively treated who therefore face a risk of relapse and recurrence.

Such individuals include those which have been diagnosed as having colorectal cancer including localized only or localized and metastasized colorectal cancer which has been resected or otherwise treated. Such individuals also include those with an elevated risk as ascertained by genetic evaluation. For example, individuals with APC mutations can be identified following the U.S. Pat. No. 5,352,775 issued Oct. 4, 1992 to Albertsen et al., which is incorporated herein by reference. Furthermore, such individuals include: those suffering from inflammatory bowel disease, particularly those with ulcerative colitis; those with colonic polyps; those with familial adenomatous polyposis, a heritable mutation predisposing patients to develop large numbers of intestinal polyps; those with Peutz-Jeghers syndrome; those with hereditary nonpolyposis coli, a heritable mutation which predisposes people to develop colon carcinoma; those with Turcot syndrome-colon carcinoma in conjunction with independent tumors of the central nervous system; and individuals engaging in rectal intercourse. The vaccines of the present invention may be to susceptible individuals prophylactically to prevent and combat colorectal cancer metastasis.

The invention relates to compositions which are the active components of such vaccines or required to make the active components, to methods of making such compositions including the active components, and to methods of making and using vaccines.

The nucleotide sequence of the CRCA-1 transcript is set forth as SEQ ID NO:1 and the amino acid sequences of the various translation products are set forth in SEQ ID NOS:2–81. The present invention relates to isolated fragments of the CRCA-1 transcript that encode specific CRCA-1 translation products.

The present invention relates to recombinant vectors, including expression vectors, that comprise the CRCA-1 transcript or a fragment thereof. The present invention relates to recombinant vectors, inlcuding expression vectors that comprise nucleotide sequences that encode a CRCA-1 translation product or a functional fragment thereof.

The present invention relates to host cells which comprise such vectors and to methods of making CRCA-1 translation products using such recombinant cells.

The present invention relates to the isolated CRCA-1 transcript and to the isolated CRCA-1 translation products and to isolated antibodies specific for such products and to hybridomas which produce such antibodies.

The present invention relates to the isolated CRCA-1 translation products and functional fragments thereof. Accordingly, some aspects of the invention relate to isolated proteins that comprise at least one epitope of a CRCA-1 translation product.

Some aspects of the invention relate to the above described isolated proteins which are haptenized to render them more immunogenic. That is, some aspects of the invention relate to haptenized proteins that comprise at least one CRCA-1 translation product epitope.

Accordingly, some aspects of the invention relate to isolated nucleic acid molecules that encode proteins that comprise at least one CRCA-1 translation product epitope.

Naked DNA vaccines are described in PCT/US90/01515, which is incorporated herein by reference. Others teach the use of liposome mediated DNA transfer, DNA delivery using microprojectiles (U.S. Pat. No. 4,945,050 issued Jul. 31, 1990 to Sanford et al., which is incorporated herein by reference), and DNA delivery using electroporation. In each case, the DNA may be plasmid DNA that is produced in bacteria, isolated and administered to the animal to be treated. The plasmid DNA molecules are taken up by the cells of the animal where the sequences that encode the protein of interest are expressed. The protein thus produced provides a therapeutic or prophylactic effect on the animal.

The use of vectors including viral vectors and other means of delivering nucleic acid molecules to cells of an individual in order to produce a therapeutic and/or prophylactic immunological effect on the individual are similarly well known. Recombinant vaccines that employ vaccinia vectors are, for example, disclosed in U.S. Pat. No. 5,017,487 issued May 21, 1991 to Stunnenberg et al. which is incorporated herein by reference.

In some cases, tumor cells from the patient are killed or inactivated and administered as a vaccine product. Berd et al. May 1986 *Cancer Research* 46:2572–2577 and Berd et al. May 1991 *Cancer Research* 51:2731–2734, which are incorporated herein by reference, describes the preparation and use of tumor cell based vaccine products. According to some aspects of the present invention, the methods and techniques described in Berd et al. are adapted by using colorectal cancer cells instead of melanoma cells.

The manufacture and use of isolated translation products and fragments thereof useful for example as laboratory reagents or components of subunit vaccines are well known. One having ordinary skill in the art can isolate the CRCA-1 transcript or the specific portion thereof that encodes a CRCA-1 translation product or a fragment thereof. Once isolated, the nucleic acid molecule can be inserted it into an expression vector using standard techniques and readily available starting materials.

The recombinant expression vector that comprises a nucleotide sequence that encodes the nucleic acid molecule that encodes a CRCA-1 translation product or a fragment thereof or a protein that comprises the CRCA-1 translation product or a fragment thereof. The recombinant expression vectors of the invention are useful for transforming hosts to prepare recombinant expression systems for preparing the isolated proteins of the invention.

The present invention relates to a host cell that comprises the recombinant expression vector that includes a nucleotide sequence that encodes one or more CRCA-1 translation products or a fragment thereof or a protein that comprises one or more CRCA-1 translation products or a fragment thereof. Host cells for use in well known recombinant expression systems for production of proteins are well known and readily available. Examples of host cells include bacteria cells such as *E. coli*, yeast cells such as *S. cerevisia*, insect cells such as *S. frugiperda*, non-human mammalian tissue culture cells chinese hamster ovary (CHO) cells and human tissue culture cells such as HeLa cells.

The present invention relates to a transgenic non-human mammal that comprises the recombinant expression vector that comprises a nucleic acid sequence that encodes the proteins of the invention. Transgenic non-human mammals useful to produce recombinant proteins are well known as are the expression vectors necessary and the techniques for generating transgenic animals. Generally, the transgenic animal comprises a recombinant expression vector in which the nucleotide sequence that encodes one or more CRCA-1 translation products or a fragment thereof or a protein that comprises the one or more CRCA-1 translation products or a fragment thereof operably linked to a mammary cell specific promoter whereby the coding sequence is only expressed in mammary cells and the recombinant rotein so expressed is recovered from the animal's milk.

In some embodiments, for example, one having ordinary skill in the art can, using well known techniques, insert such DNA molecules into a commercially available expression vector for use in well known expression systems such as those described herein.

The expression vector including the DNA that encodes a CRCA-1 translation product or a fnctional fragment thereof or a protein that comprises a CRCA-1 translation product or a functional fragment thereof is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. The methods of purifying the CRCA-1 translation products or a fragment thereof or a protein that comprises the same using antibodies which specifically bind to the protein are well known. Antibodies which specifically bind to a particular protein may be used to purify the protein from natural sources using well known techniques and readily available starting materials. Such antibodies may also be used to purify the protein from material present when producing the protein by recombinant DNA methodology. The present invention relates to antibodies that bind to an epitope which is present on one or more CRCA-1 translation products or a fragment thereof or a protein that comprises the same. Antibodies that bind to an epitope which is present on the CRCA-1 translation product are useful to isolate and purify the protein from both natural sources or recombinant expression systems using well known techniques such as affinity chromatography. Immunoaffinity techniques generally are described in Waldman et al. 1991 *Methods of Enzymol.* 195:391–396, which is incorporated herein by reference. Antibodies are useful to detect the presence of such protein in a sample and to determine if cells are expressing the protein. The production of antibodies and the protein structures of complete, intact antibodies, Fab fragments and F(ab)$_2$ fragments and the organization of the genetic sequences that encode such molecules are well known and are described, for example, in Harlow, E. and D. Lane (1988) *ANTIBODIES. A Laboratory Manual*, Cold Spring Harbor Laboratory, Cold Spring Harbor, N.Y. which is incorporated herein by reference.

In some embodiments of the invention, transgenic non-human animals are generated. The transgenic animals according to the invention contain nculeotides that encode one or more CRCA-1 translation products or a fragment thereof or a protein that comprises the same under the regulatory control of a mammary specific promoter. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which produce one or more CRCA-1 translation products or a fragment thereof or a protein that comprises the same. Preferred animals are goats and rodents, particularly rats and mice.

In addition to producing these proteins by recombinant techniques, automated peptide synthesizers may also be employed to produce one or more CRCA-1 translation products or a fragment thereof or a fragment thereof or a protein that comprises the same. Such techniques are well known to those having ordinary skill in the art and are useful if derivatives which have substitutions not provided for in DNA-encoded protein production.

In some embodiments, the protein that makes up a subunit vaccine or the cells or particles of a killed or inactivated vaccine may be haptenized to increase immunogenicity. In some cases, the haptenization is the conjugation of a larger molecular structure to one or more CRCA-1 translation products or a fragment thereof or a protein that comprises the same. In some cases, tumor cells from the patient are killed and haptenized as a means to make an effective vaccine product. In cases in which other cells, such as bacteria or eukaryotic cells which are provided with the genetic information to make and display a CRCA-1 translation product or a fragment thereof or a protein that comprises the same, are killed and used as the active vaccine component, such cells are haptenized to increase immunogenicity. Haptenization is well known and can be readily performed.

Methods of haptenizing cells generally and tumor cells in particular are described in Berd et al. May 1986 *Cancer Research* 46:2572–2577 and Berd et al. May 1991 *Cancer Research* 51:2731–2734, which are incorporated herein by reference. Additional haptenization protocols are disclosed in Miller et al. 1976 *J. Immunol.* 117(5:1) :1591–1526.

Haptenization compositions and methods which may be adapted to be used to prepare haptenized CRCA-1 immunogens according to the present invention include those described in the following U.S. Patents which are each incorporated herein by reference: U.S. Pat. No. 5,037,645 issued Aug. 6, 1991 to Strahilevitz; U.S. Pat. No. 5,112,606 issued May 12, 1992 to Shiosaka et al.; U.S. Pat. No. 4,526,716 issued Jul. 2, 1985 to Stevens; U.S. Pat. No. 4,329,281 issued May 11, 1982 to Christenson et al.; and U.S. Pat. No. 4,022,878 issued May 10, 1977 to Gross. Peptide vaccines and methods of enhancing immunogenicity of peptides which may be adapted to modify CRCA-1 immunogens of the invention are also described in Francis et al. 1989 *Methods of Enzymol.* 178:659–676, which is incorporated herein by reference. Sad et al. 1992 *Immunolology* 76:599–603, which is incorporated herein by reference, teaches methods of making immunotherapeutic vaccines by conjugating gonadotropin releasing hormone to diphtheria toxoid. CRCA-1 immunogens may be similarly conjugated to produce an immunotherapeutic vaccine of the present invention. MacLean et al. 1993 *Cancer Immunol. Immunother.* 36:215–222, which is incorporated herein by reference, describes conjugation methodologies for producing immunotherapeutic vaccines which may be adaptable to produce an immunotherapeutic vaccine of the present invention. The hapten is keyhole limpet hemocyanin which may be conjugated to a CRCA-1 immunogen.

Vaccines according to some aspects of the invention comprise a pharmaceutically acceptable carrier in combination with a CRCA-1 immunogen. Pharmaceutical formulations are well known and pharmaceutical compositions comprising such proteins may be routinely formulated by one having ordinary skill in the art. Suitable pharmaceutical carriers are described in Remington's Pharmaceutical Sciences, A. Osol, a standard reference text in this field, which is incorporated herein by reference. The present invention relates to an injectable pharmaceutical composition that comprises a pharmaceutically acceptable carrier and a CRCA-1 immunogen. The CRCA-1 immunogen is preferably sterile and combined with a sterile pharmaceutical carrier.

In some embodiments, for example, one or more CRCA-1 translation products or a fragment thereof or a fragment thereof or a protein that comprises the same can be formulated as a solution, suspension, emulsion or lyophilized powder in association with a pharmaceutically acceptable vehicle. Examples of such vehicles are water, saline, Ringer's solution, dextrose solution, and 5 human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

An injectable composition may comprise the CRCA-1 immunogen in a diluting agent such as, for example, sterile water, electrolytes/dextrose, fatty oils of vegetable origin, fatty esters, or polyols, such as propylene glycol and polyethylene glycol. The injectable must be sterile and free of pyrogens.

The vaccines of the present invention may be administered by any means that enables the immunogenic agent to be presented to the body's immune system for recognition and induction of an immunogenic response. Pharmaceutical compositions may be administered parenterally, i.e., intravenous, subcutaneous, intramuscular.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired. An amount of immunogen is delivered to induce a protective or therapeutically effective immune response. Those having ordinary skill in the art can readily determine the range and optimal dosage by routine methods.

The following examples are illustrative but are not meant to be limiting of the present invention.

EXAMPLES

Example 1

As stated above, a CRCA-1 translation product binding moiety is a CRCA-1 translation product ligand that may be an antibody, a protein, a polypeptide, a peptide or a non-peptide. Peptides and non-peptide CCK A receptor specific ligands may be identified using well known technology.

Over the past 10 years, it has become recognized that the specific high-affinity interaction of a receptor and a ligand, for example a CRCA-1 translation product and an anti-CRCA-1 translation product antibody, has its basis in the 3-dimensional conformational space of the ligand and the complimentary 3-dimensional configuration of the region of the molecule involved in ligand binding. In addition, it has become recognized that various arrays of naturally-occurring amino acids, non-natural amino acids, and organic molecules can be organized in configurations that are unrelated to the natural ligands in their linear structure, but resemble the 3-dimensional structure of the natural ligands in conformational space and, thus, are recognized by receptors with high affinity and specificity. Furthermore, techniques have been described in the literature that permit one of ordinary skill in the art to generate large libraries of these arrays of natural amino acids, non-natural amino acids and organic compounds to prospectively identify individual compounds that interact with receptors with high affinity and specificity which are unrelated to the native ligand of that receptor. Thus, it is a relatively straightforward task for one of ordinary skill in the art to identify arrays of naturally occurring amino acids, non-natural amino acids, or organic compounds which can bind specifically and tightly to the CRCA-1 translation product, which bear no structural relationship to an anti-CRCA-1 translation product antibody.

To identify CRCA-1 translation product ligands that are peptides, those having ordinary skill in the art can use any of the well known methodologies for screening random peptide libraries in order to identify peptides which bind to the CRCA-1 translation product. In the most basic of methodologies, the peptides which bind to the target are isolated and sequenced. In some methodologies, each random peptide is linked to a nucleic acid molecule which includes the coding sequence for that particular random peptide. The random peptides, each with an attached coding sequence, are contacted with a CRCA-1 translation product and the peptides which are unbound to the CRCA-1 translation product are removed. The nucleic acid molecule which includes the coding sequence of the peptide that binds to the CRCA-1 translation product can then be used to determine the amino acid sequence of the peptide as well as produce large quantities of the peptide. It is also possible to produce peptide libraries on solid supports where the spatial location on the support corresponds to a specific synthesis and therefore specific peptide. Such methods often use photolithography-like steps to create diverse peptide libraries on solid supports in which the spatial address on the support allows for the determination of the sequence.

The production of organic compound libraries on solid supports may also be used to produce combinatorial libraries of non-peptide compounds such as oligonucleotides and sugars, for example. As in the case of peptide libraries on solid supports, the spatial location on the support corresponds to a specific synthesis and therefore specific compound. Such methods often use photolithography-like steps to create diverse compound libraries on solid supports in which the spatial address on the support allows for the determination of the synthesis scheme which produced the compound. Once the synthesis scheme is identified, the structure of the compound can become known.

Gallop et al. 1994 *J. Medicinal Chemistry* 37:1233, which is incorporated herein by reference, provides a review of several of the various methodologies of screening random peptide libraries and identifying peptides from such libraries which bind to target proteins. Following these teachings, CRCA-1 translation product specific ligands that are peptides and that are useful as CRCA-1 translation product specific binding moieties may be identified by those having ordinary skill in the art.

Peptides and proteins displayed on phage particles are described in Gallop et al. Supra. Random arrays of nucleic acids can be inserted into genes encoding surface proteins of bacteriophage which are employed to infect bacteria, yielding phage expressing the peptides encoded by the random array of nucleotides on their surface. These phage displaying the peptide can be employed to determine whether those peptides can bind to specific proteins, receptors, antibodies, etc. The identity of the peptide can be determined by sequencing the recombinant DNA from the phage expressing the peptide. This approach has the potential to yield vast arrays of peptides in a library (up to $10^9$ unique peptides). This technique has been employed to identify novel binding peptides to the fibrinogen receptor on platelets, which bear no sequence homology to the natural occurring ligands of this receptor (Smith et al., 1993 *Gene* 128:37, which is incorporated herein by reference). Similarly, this technique has been applied to identify peptides which bind to the MHC class II receptor (Hammer et al., 1993 *Cell* 74:197, which is incorporated herein by reference) and the chaperonin receptor (Blond-Elguindi et al., 1993 *Cell* 75:717, which is incorporated herein by reference).

Peptides displayed on plasmids are described in Gallop et al. Supra. In this approach, the random oligonucleotides which encode the library of peptides can be expressed on a specific plasmid whose expression is under the control of a specific promoter, such as the lac operon. The peptides are expressed as fusion proteins coupled to the Lac I protein, under the control of the lac operon. The fusion protein specifically binds to the lac operator on the plasmid and so the random peptide is associated with the specific DNA element that encodes it. In this way, the sequence of the peptide can be deduced, by PCR of the DNA associated with the fusion protein. These proteins can be screened in solution phase to determine whether they bind to specific receptors. Employing this approach, novel substrates have been identified for specific enzymes (Schatz 1993).

A variation of the above technique, also described in Gallop et al. Supra, can be employed in which random oligonucleotides encoding peptide libraries on plasmids can be expressed in cell-free systems. In this approach, a molecular DNA library can be constructed containing the random array of oligonucleotides, which are then expressed in a bacterial in vitro transcription/translation system. The identity of the ligand is determined by purifying the complex of nascent chain peptide/polysome containing the mRNA of interest on affinity resins composed of the receptor and then sequencing following amplification with RT-PCR. Employing this technique permits generation of large libraries (up to 1011 recombinants). Peptides which recognize antibodies specifically directed to dynorphin have been identified employing this technique (Cull et al., 1992 Proc. Natl. Acad. Sci. USA 89:1865, which is incorporated herein by reference).

Libraries of peptides can be generated for screening against a receptor by chemical synthesis. For example, simultaneous preparation of large numbers of diverse peptides have been generated employing the approach of multiple peptide synthesis as described in Gallop et al. Supra. In one application, random peptides are generated by standard solid-phase Merrifield synthesis on polyacrylamide microtiter plates (multipin synthesis) which are subsequently screened for their ability to compete with receptor binding in a standard competitive binding assay (Wang et al., 1993 Bioorg. Med. Chem. Lett. 3:447, which is incorporated herein by reference). Indeed, this approach has been employed to identify novel binding peptides to the substance P receptor (Wang et al. Supra). Similarly, peptide libraries can be constructed by multiple peptide synthesis employing the "tea bag" method in which bags of solid support resin are sequentially incubated with various amino acids to generate arrays of different peptides (Gallop et al. Supra). Employing this approach, peptides which bind to the integrin receptor (Ruggeri et al., 1986 Proc. Natl. Acad. Sci. USA 83:5708, which is incorporated herein by reference) and the neuropeptide Y receptor (Beck-Sickinger et al., 1990 Int. J. Peptide Protein Res. 36:522, which is incorporated herein by reference) have been identified.

In general, the generation and utility of combinatorial libraries depend on (1) a method to generate diverse arrays of building blocks, (2) a method for identifying members of the array that yield the desired function, and (3) a method for deconvoluting the structure of that member. Several approaches to these constraints have been defined.

The following is a description of methods of library generation which can be used in procedures for identifying CRCA-1 translation product specific ligands according to the invention.

Modifications of the above approaches can be employed to generate libraries of vast molecular diversity by connecting together members of a set of chemical building blocks, such as amino acids, in all possible combinations (Gallop et al. Supra) In one approach, mixtures of activated monomers are coupled to a growing chain of amino acids on a solid support at each cycle. This is a multivalent synthetic system.

Also, split synthesis involves incubating the growing chain in individual reactions containing only a single building block (Gallop et al. Supra). Following attachment, resin from all the reactions are mixed and apportioned into individual reactions for the next step of coupling. These approaches yield a stochastic collection of $n^x$ different peptides for screening, where n is the number of building blocks and x is the number of cycles of reaction.

Alternatively, arrays of molecules can be generated in which one or more positions contain known amino acids, while the remainder are random (Gallop et al. Supra). These yield a limited library which is screened for members with the desired activity. These members are identified, their structure determined, and the structure regenerated with another position containing defined amino acids and screened. This iterative approach ultimately yields peptides which are optimal for recognizing the conformational binding pocket of a receptor.

In addition, arrays are not limited to amino acids forming peptides, but can be extended to linear and nonlinear arrays of organic molecules (Gordon et al., 1994 J. Medicinal Chemistry 37:1385, which is incorporated herein by reference). Indeed, employing this approach of generating libraries of randomly arrayed inorganic building blocks, ligands which bound to 7-transmembrane receptors were identified (Zuckermann et al., 1994 J. Med. Chem. 37:2678, which is incorporated herein by reference).

Libraries are currently being constructed which can be modified after synthesis to alter the chemical side groups and bonds, to give "designer" arrays to test for their interaction with receptors (Osteresh et al., 1994 Proc. Natl. Acad. Sci. USA 91:11138, which is incorporated herein by reference). This technique, generating "libraries from libraries", was applied to the permethylation of a peptide library which yielded compounds with selective antimicrobial activity against gram positive bacteria.

Libraries are also being constructed to express arrays of pharmacological motifs, rather than specific structural arrays of amino acids (Sepetov et al., 1995 Proc. Natl. Acad. Sci. USA 92:5426, which is incorporated herein by reference). This technique seeks to identify structural motifs that have specific affinities for receptors, which can be modified in further refinements employing libraries to define structure-activity relationships. Employing this approach of searching motif libraries, generating "libraries of libraries", reduces the number of component members required for screening in the early phase of library examination.

The following is a description of methods of identifying CRCA-1 translation product specific ligands according to the invention from libraries of randomly generated molecules.

Components in the library which interact with receptors may be identified by their binding to receptors immobilized on solid support (Gordon et al. Supra).

They may also be identified by their ability to compete with native ligand for binding to cognate receptors in solution phase (Gordon et al. Supra).

Components may be identified by their binding to soluble receptors when those components are immobilized on solid supports (Gordon et al. Supra).

Once a member of a library which binds receptors has been identified, the structure of that member must be deconvoluted (deduced) in order to identify the structure and generate large quantities to work with, or develop further analogs to study structure-activity relationships. The following is a description of methods of deconvolution for deducing the structure of molecules identified as potential CRCA-1 translation product specific ligands according to the invention.

Peptide libraries may be expressed on the surface of bacteriophage particles (Gallop et al. Supra). Once the peptide interacting with the receptor has been identified, its structure can be deduced by isolating the DNA from the phage and determining its sequence by PCR.

Libraries expressed on plasmids, under the control of the Lac operon can be deconvoluted since these peptides are fused with the lac I protein which specifically interacts with the lac operon on the plasmid encoding the peptide (Gallop et al. Supra) The structure can be deduced by isolating that plasmid attached to the lac I protein and deducing the nucleotide and peptide sequence by PCR.

Libraries expressed on plasmids can also be expressed in cell-free systems employing transcription/translation systems (Gallop et al. Supra). In this paradigm, the protein interacting with receptors is isolated with its attached ribosome and mRNA. The sequence of the peptide is deduced by RT-PCR of the associated mRNA.

Library construction can be coupled with photolithography, so that the structure of any member of the library can be deduced by determining its position within the substrate array (Gallop et al. Supra). This technique is termed positional addressability, since the structural information can be deduced by the precise position of the member.

Members of a library can also be identified by tagging the library with identifiable arrays of other molecules (Ohlmeyer et al., 1993 Proc. Natl. Acad. Sci. USA 90:10922, which is incorporated herein by reference, and Gallop et al. Supra) . This technique is a modification of associating the peptide with the plasmid of phage encoding the sequence, described above. Some methods employ arrays of nucleotides to encode the sequential synthetic history of the peptide. Thus, nucleotides are attached to the growing peptide sequentially, and can be decoded by PCR to yield the structure of the associated peptide. Alternatively, arrays of small organic molecules can be employed as sequencable tags which encode the sequential synthetic history of the peptide. Thus, nucleotides are attached to the growing peptide sequentially, and can be decoded by PCR to yield the structure of the associated peptide. Alternatively, arrays of small organic molecules can be employed as sequencable tags which encode the sequential synthetic history of the library member.

Finally, the structure of a member of the library can be directly determined by amino acid sequence analysis.

The following patents, which are each incorporated herein by reference, describe methods of making random peptide or non-peptide libraries and screening such libraries to identify compounds that bind to target proteins. As used in the present invention, CRCA-1 translation product can be the targets used to identify the peptide and non-peptide ligands generated and screened as disclosed in the patents.

U.S. Pat. No. 5,270,170 issued to Schatz et al. on Dec. 14, 1993, and U.S. Pat. No. 5,338,665 issued to Schatz et al. on Aug. 16, 1994, which are both incorporated herein by reference, refer to peptide libraries and screening methods which can be used to identify CRCA-1 translation product ligands.

U.S. Pat. No. 5,395,750 issued to Dillon et al. on Mar. 7, 1995, which is incorporated herein by reference, refers to methods of producing proteins which bind to predetermined antigens. Such methods can be used to produce CRCA-1 translation product ligands.

U.S. Pat. No. 5,223,409 issued to Ladner et al. on Jun. 29, 1993, which is incorporated herein by reference, refers to the directed evolution to novel binding proteins. Such proteins may be produced and screened as disclosed therein to identify CRCA-1 translation product ligands.

U.S. Pat. No. 5,366,862 issued to Venton et al. on Nov. 22, 1994, which is incorporated herein by reference, refers to methods for generating and screening useful peptides. The methods herein described can be used to identify CRCA-1 translation product ligands.

U.S. Pat. No. 5,340,474 issued to Kauvar on Aug. 23, 1994 as well as U.S. Pat. No. 5,133,866, U.S. Pat. No. 4,963,263 and U.S. Pat. No. 5,217,869, which are each incorporated herein by reference, can be used to identify CRCA-1 translation product ligands.

U.S. Pat. No. 5,405,783 issued to Pirrung et al. on Apr. 11, 1995, which is incorporated herein by reference, refers to large scale photolithographic solid phase synthesis of an array of polymers. The teachings therein can be used to identify CRCA-1 translation product ligands.

U.S. Pat. No. 5,143,854 issued to Pirrung et al. on Sep. 1, 1992, which is incorporated herein by reference, refers to a large scale photolithographic solid phase synthesis of polypeptides and receptor binding screening thereof.

U.S. Pat. No. 5,384,261 issued to Winkler et al. on Jan. 24, 1995, which is incorporated herein by reference, refers to very large scale immobilized polymer synthesis using mechanically directed flow patterns. Such methods are useful to identify CRCA-1 translation product ligands.

U.S. Pat. No. 5,221,736 issued to Coolidge et al. on Jun. 22, 1993, which is incorporated herein by reference, refers to sequential peptide and oligonucleotide synthesis using immunoaffinity techniques. Such techniques may be used to identify CRCA-1 translation product ligands.

U.S. Pat. No. 5,412,087 issued to McGall et al. on May 2, 1995, which is incorporated herein by reference, refers to spatially addressable immobilization of oligonucleotides and other biological polymers on surfaces. Such methods may be used to identify CRCA-1 translation product ligands.

U.S. Pat. No. 5,324,483 issued to Cody et al. on Jun. 28, 1994, which is incorporated herein by reference, refers to apparatus for multiple simultaneous synthesis. The apparatus and method disclosed therein may be used to produce multiple compounds which can be screened to identify CRCA-1 translation product ligands.

U.S. Pat. No. 5,252,743 issued to Barrett et al. on Oct. 12, 1993, which is incorporated herein by reference, refers to spatially addressable immobilization of anti-ligands on surfaces. The methods and compositions described therein may be used to identify CRCA-1 translation product ligands.

U.S. Pat. No. 5,424,186 issued to Foder et al. on Jun. 13, 1995, which is incorporated herein by reference, refers to a very large scale immobilized polymer synthesis. The method of synthesizing oligonucleotides described therein may be used to identify CRCA-1 translation product ligands.

U.S. Pat. No. 5,420,328 issued to Campbell on May 30, 1995, which is incorporated herein by reference, refers to methods of synthesis of phosphonate esters. The phosphonate esters so produced may be screened to identify compounds which are CRCA-1 translation product ligands.

U.S. Pat. No. 5,288,514 issued to Ellman on Feb. 22, 1994, which is incorporated herein by reference, refers to solid phase and combinatorial synthesis of benzodiazepine compounds on a solid support. Such methods and compounds may be used to identify CRCA-1 translation product ligands.

As noted above, CRCA-1 translation product ligands may also be antibodies and fragments thereof. Indeed, antibodies raised to unique determinants of these receptors will recognize that protein, and only that protein and, consequently, can serve as a specific targeting molecule which can be used to direct novel diagnostics and therapeutics to this unique marker. In addition, these antibodies can be used to identify the presence of CRCA-1 translation product or fragments there of in biological samples, to diagnose the presence of colorectal cancer cells in vitro.

We claim:

1. An in vitro method of determining whether or not an individual has metastasized colorectal cancer cells comprising the steps of examining a sample of extraintestinal tissue and/or body fluids from an individual to determine whether CRCA-1 transcript is being expressed by cells in said sample wherein expression of said CRCA-1 transcript is indicative of the presence of metastasized colorectal cancer cells in said sample, wherein said CRCA-1 transcript has the nucleotide sequence of SEQ ID NO:83 or SEQ ID NO:85.

2. The method of claim 1 wherein expression of said CRCA-1 transcript by said cells is determined by polymerase chain reaction wherein said sample is contacted with primers that selectively amplify said CRCA-1 transcript or cDNA generated therefrom.

3. The method of claim 1 wherein said sample is body fluid.

4. The method of claim 3 wherein said sample is blood.

5. The method of claim 2 wherein said sample is body fluid.

6. The method of claim 5 wherein said sample is blood.

7. An in vitro method of determining whether or not a tumor cell is a colorectal tumor cell comprising the steps of determining whether said tumor cell expresses CRCA-1 transcript wherein expression of CRCA-1 transcript indicates that the tumor cell is a colorectal tumor cell; wherein said CRCA-1 transcript has the nucleotide sequence of SEQ ID NO:83 or SEQ ID NO:85.

8. The method of claim 7 wherein expression of said CRCA-1 transcript by said tumor cells is determined by polymerase chain reaction wherein MRNA from said cell or cDNA generated from said RNA is contacted with primers that selectively amplify said CRCA-1 transcript or cDNA generated therefrom.

9. An in vitro method of determining whether or not an individual has metastasized colorectal cancer comprising the steps of examining a sample of extraintestinal tissue from an individual to determine whether a CRCA-1 transcript is present in said sample, wherein the presence of a CRCA-1 transcript in said sample indicates that said individual has metastasized colorectal cancer; wherein said CRCA-1 transcript has the nucleotide sequence of SEQ ID NO:83 or SEQ ID NO:85.

10. The method of claim 9 wherein said CRCA-1 transcript is detected by polymerase chain reaction assay using primers which specifically amplify CRCA-1 transcript sequences.

11. An in vitro PCR assay kit for determining whether or not an individual has colorectal cancer by detecting the presence of CRCA-1 transcript in a sample of extraintestinal tissue and/or body fluids from an individual, wherein the presence of said CRCA-1 transcript in said sample indicates that individual has colorectal cancer, wherein said CRCA-1 transcript has the nucleotide sequence of SEQ ID NO:83 or SEQ ID NO:85, said kit comprising:

a first container comprising PCR primers that are unique to and specifically amplify said CRCA-1 transcript or cDNA generated therefrom;

a second container comprising a size marker, said size marker being the expected size of amplified DNA if said CRCA-1 transcript is present in said sample; and instructions for using said kit.

* * * * *